United States Patent
Inkpen et al.

(10) Patent No.: US 9,554,812 B2
(45) Date of Patent: Jan. 31, 2017

(54) TOOL WITH INTEGRATED NAVIGATION AND GUIDANCE SYSTEM AND RELATED APPARATUS AND METHODS

(75) Inventors: Kevin Bryant Inkpen, Vancouver (CA); Antony John Hodgson, Vancouver (CA); Pierre Guy, Vancouver (CA); Willem J. Atsma, Vancouver (CA); Stephane Lavallee, St Martin D'Uriage (FR); James B. Stiehl, Salem, IL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 512 days.

(21) Appl. No.: 13/982,320

(22) PCT Filed: Feb. 17, 2012

(86) PCT No.: PCT/CA2012/050098
§ 371 (c)(1),
(2), (4) Date: Nov. 8, 2013

(87) PCT Pub. No.: WO2012/109760
PCT Pub. Date: Aug. 23, 2012

(65) Prior Publication Data
US 2014/0148808 A1    May 29, 2014

Related U.S. Application Data

(60) Provisional application No. 61/444,535, filed on Feb. 18, 2011, provisional application No. 61/444,558, (Continued)

(51) Int. Cl.
*A61B 17/17* (2006.01)
*G01B 7/00* (2006.01)
(Continued)

(52) U.S. Cl.
CPC ........... *A61B 17/1707* (2013.01); *A61B 17/15* (2013.01); *A61B 17/162* (2013.01); (Continued)

(58) Field of Classification Search
CPC ................................................... A61B 17/1707
See application file for complete search history.

(56) References Cited

U.S. PATENT DOCUMENTS

| 6,074,394 A | 6/2000 | Krause |
|---|---|---|
| 6,503,249 B1 | 1/2003 | Krause |

(Continued)

FOREIGN PATENT DOCUMENTS

| CN | 1633948 A | 7/2005 |
|---|---|---|
| CN | 101507657 B | 1/2011 |

(Continued)

OTHER PUBLICATIONS

International Search Report, Application No. PCT/CA2012/050098, mailed Jun. 14, 2012, 5 pages.

(Continued)

*Primary Examiner* — Andrew Yang
(74) *Attorney, Agent, or Firm* — Wayne C. Jaeschke, Jr.

(57) ABSTRACT

Methods and apparatus for integrating an electromagnetic navigation system and a tool and aligning the tool with a target are presented, including a sensor tool, a tool, a field generator, a display, and a computer. The sensor tool attaches to a target component in a unique position relative to target features. The field generator is fixed relative to the tool except in rotation about a tool axis. The display is adjustably mounted to the tool and automatically adjusts image parameters. Target registration and error compensation methods are provided. The system detects magnetic field and signal disturbances that may lead to inaccurate navigation, filters navigation data, and adjusts filtering (Continued)

parameters based on detected conditions. Apparatus for proximally locking an IM nail such that a clear passage through the cannulation of the nail is maintained are provided.

19 Claims, 50 Drawing Sheets

Related U.S. Application Data filed on Feb. 18, 2011, provisional application No. 61/444,600, filed on Feb. 18, 2011, provisional application No. 61/476,709, filed on Apr. 18, 2011, provisional application No. 61/553,499, filed on Oct. 31, 2011.

(51) Int. Cl.

| | | |
|---|---|---|
| *A61B 17/15* | (2006.01) | |
| *A61B 17/16* | (2006.01) | |
| *A61B 17/72* | (2006.01) | |
| *A61B 17/74* | (2006.01) | |
| A61B 17/14 | (2006.01) | |
| A61B 5/06 | (2006.01) | |
| A61B 17/88 | (2006.01) | |
| A61B 17/92 | (2006.01) | |

(52) U.S. Cl.
CPC ...... *A61B 17/1703* (2013.01); *A61B 17/1725* (2013.01); *A61B 17/72* (2013.01); *A61B 17/744* (2013.01); *A61B 34/20* (2016.02); *A61B 90/06* (2016.02); *G01B 7/003* (2013.01); *A61B 5/062* (2013.01); *A61B 17/148* (2013.01); *A61B 17/1626* (2013.01); *A61B 17/1742* (2013.01); *A61B 17/725* (2013.01); *A61B 17/8875* (2013.01); *A61B 17/921* (2013.01); *A61B 2034/2051* (2016.02)

(56) References Cited

U.S. PATENT DOCUMENTS

| | | |
|---|---|---|
| 7,060,075 B2 | 6/2006 | Govari et al. |
| 2003/0184285 A1 | 10/2003 | Anderson et al. |
| 2010/0274121 A1* | 10/2010 | Ritchey .................. A61B 5/05 600/424 |

FOREIGN PATENT DOCUMENTS

| | | |
|---|---|---|
| CN | 103002819 A | 3/2013 |
| JP | 2002/513305 A | 5/2002 |
| JP | 2004/130094 A | 4/2004 |
| WO | WO 2006/133573 A1 | 12/2006 |
| WO | WO 2010/027109 A1 | 3/2010 |
| WO | WO 2010/129141 A2 | 11/2010 |
| WO | WO 2010/129308 A2 | 11/2010 |

OTHER PUBLICATIONS

State Intellectual Property Office of People's Republic Search Report, Application No. 201280009371.5, dated Jun. 15, 2015, 3 pages.

* cited by examiner

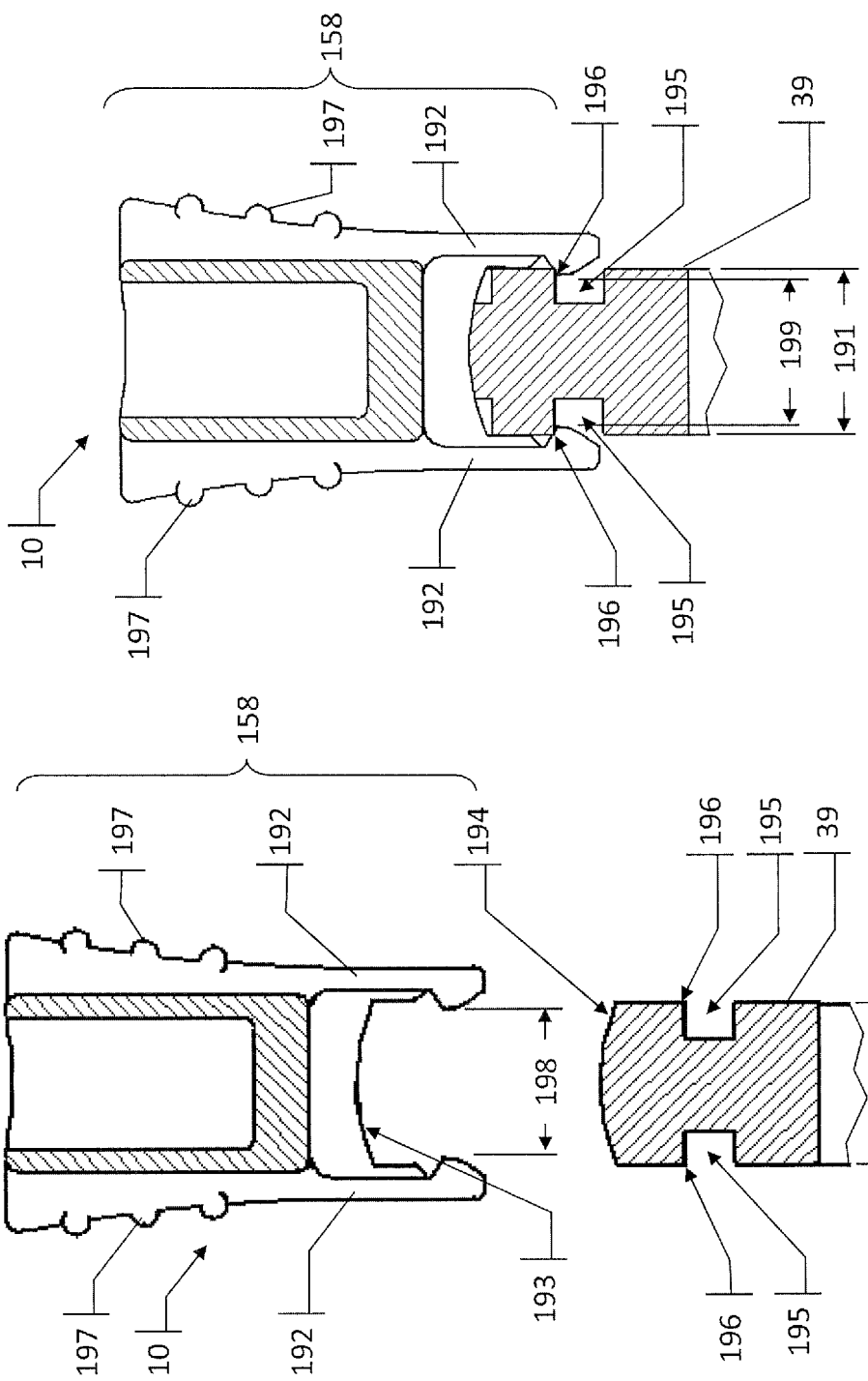

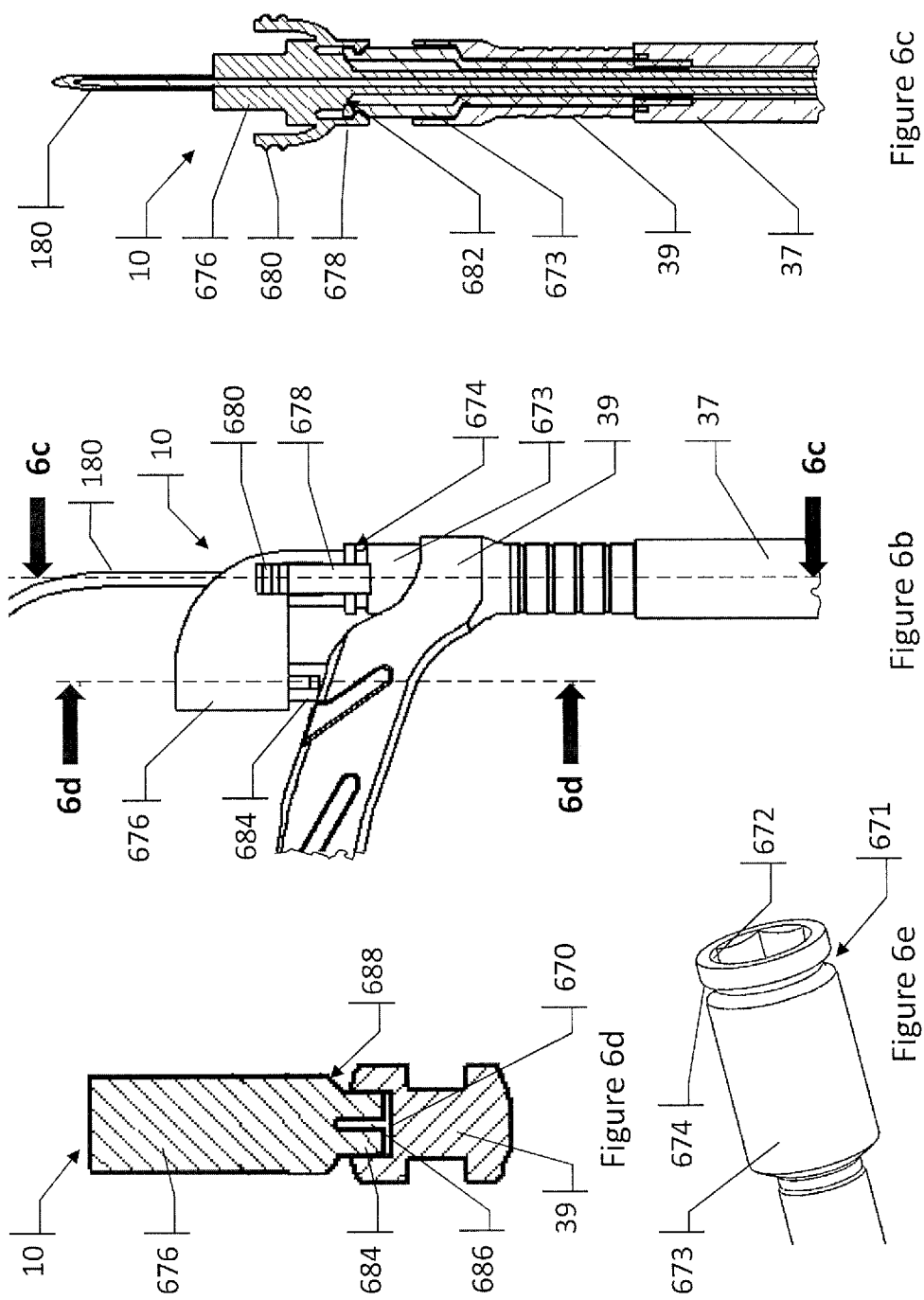

TOOL WITH INTEGRATED NAVIGATION AND GUIDANCE SYSTEM AND RELATED APPARATUS AND METHODS

REFERENCE TO RELATED APPLICATION

This application claims priority from U.S. patent application Nos. 61/444,535 filed Feb. 18, 2011, 61/444,558 filed Feb. 18, 2011, 61/444,600 filed Feb. 18, 2011, 61/476,709 filed Apr. 18, 2011, and 61/553,499 filed Oct. 31, 2011. For purposes of the United States of America, this application claims the benefit under 35 U.S.C. §119 of from U.S. patent application Nos. 61/444,535 filed Feb. 18, 2011, 61/444,558 filed Feb. 18, 2011, 61/444,600 filed Feb. 18, 2011, 61/476,709 filed Apr. 18, 2011, and 61/553,499 filed Oct. 31, 2011 all of which are hereby incorporated herein by reference.

TECHNICAL FIELD

This invention relates to guidance and navigation of tools. Drills and saws are non-limiting examples of tools. The invention has application to positioning tools relative to features that may be hidden from view. The invention may be applied in positioning surgical tools but also has non-surgical applications.

BACKGROUND

There are procedures in many fields including manufacturing, assembly, repair, and surgery in which it is useful to align a tool with a target path, feature, or other target location that may be hidden from view or not sufficiently visible to the user. For example in airframe assembly and repair it may be necessary to drill a hole through a layer of material in line with an existing hole in an inaccessible component positioned behind the material. For another example many surgical procedures require a surgeon to align a tool, such as a drill, a guide wire driver, a bone saw, or an ultrasound probe with a target path that cannot be sufficiently marked or seen. The target path may be an ideal plane or trajectory through tissue as determined in preoperative planning or determined using intraoperative techniques, for example an estimated centerline of an anatomical feature such as a femoral neck as described by Hodgson in international patent publication WO/2006/133573. The target path may also be related to features of an implant, such as a fixation screw hole in a bone plate or IM ("IM") nail, wherein the objective is to align a drill, guide wire driver, or other tool relative to the hole when the hole or the direction of the hole is hidden from view.

Some examples of surgical procedures which can be facilitated by guidance to establish a desired tool alignment are:

- femoral head resurfacing. This procedure involves inserting a guide wire through the femoral neck along a target path at a planned angle and location.
- pedicle screw fixation in spine surgery where a drill, drill-guide, guide wire or screw must be inserted along a target path, within a known structure (a pedicle) and for a limited depth to avoid injury to surrounding structures outside the bone.
- placement of ilio-sacral screws in pelvic bone surgery, where a drill, drill-guide, guide wire or screw must be inserted along a target path (thru the iliac bone, within the sacral ala and vertebral body) and for a limited depth to avoid injury to surrounding structures outside the bone.
- osteotomy (cutting of a bone), where orientation of a surgical saw to be used to cut a bone in a specific planned orientation would be critical to the next steps of the procedure: realignment of bones, placement of implants (e.g. knee arthroplasty)
- placement of hip or knee arthroplasty implants in a planned orientation (e.g placement of an acetabular component in hip arthroplasty)
- locating fixed solid organs (e.g. liver, pancreas, kidney, or other) or mobile hollow organs (e.g. bowel, bladder) for percutaneous placement of a stent or device or for establishing access to a planned location which is hidden from view. (e.g. nephrostomy tube, percutaneous endoscopic gastrostomy tube, hepatic, biliary or pancreatic diverting stent) or for sampling a mass or tissue at a location hidden from view but known relative to a probe, for the purpose of biopsy.

Furthermore in many procedures such as drilling or cutting with a tool, the user may find it useful to know how far a tool has progressed along a target path from a starting point, for example to know how deep a hole has been drilled or in order to select the correct length of screw, pin, or the like to install. For example in various surgical procedures, surgeons may want an estimate of the correct length of a screw to be installed in a drilled hole such that the screw spans the bone at the hole location but does not protrude excessively from the bone into the surrounding tissue.

Also in many tool alignment procedures, the user may need to use the tool in various orientations relative to the user's point of view. The user may also prefer to hold the tool in their right or left hand, which may affect the orientation of the tool and the visibility of the tool and the alignment target area. For example in many surgical procedures the surgeon may need to use a tool in various orientations to gain access to working space and a clear tool path, for example to have the tool pass by the non-involved limb of the patient, the operating table, and the various limb holders, bolsters and the like that are used in surgery.

Generally, tool guidance and navigation procedures require some form of user interface and feedback, such as a visual display, to provide targeting information to the user.

Intramedullary nailing ("IM nailing") is one example of a surgical application in which it is necessary to align a tool with hidden features. In the following detailed description IM nailing is provided as a non-limiting example to illustrate application of various aspects of the invention.

To stabilize a fractured long bone, surgeons usually insert an IM nail ("IM nail") along the medullary canal of the bone. To hold the distal section of the fractured bone, distal locking screws are installed transverse to the axis of the bone and passing through holes in the distal end of the IM nail. Installing the distal locking screws creates a challenge for the surgeon because the locking screw holes are inside the bone and cannot be seen. An IM nail may also distort unpredictably as it is pushed distally down through the bone and as the bone fragments are aligned, therefore the position of the distal locking holes may be difficult to determine using guides attached to the proximal end of the nail.

Surgeons commonly locate the distal locking holes by trial and error using hand-held guide wires or a drill and a series of x-ray images taken during the operation. The main tool for acquiring these images is a C-arm fluoroscope, which is typically moved incrementally until the holes appear as circles in the image, thus indicating that the fluoroscope is aligned with the distal locking holes. Then the drill bit or drill guide is typically positioned on the skin surface over the area of the hole and adjusted, using more images, until it is centered and aligned with the hole. This method is time-consuming and exposes the surgical team and patient to radiation.

Although the radiation dose a surgeon receives from a C-arm fluoroscope has generally been considered safe, there is some disagreement about this. Hafez (2005) estimates that radiation doses recorded at the fingertips are as much as seventy five times higher than doses recorded at the base of the fingers. Cumulative exposure to radiation may be a concern particularly for trauma surgery teams.

Computer assisted techniques, making use of electromagnetic position tracking technology to assist with IM nailing surgery, are described in Krause, U.S. Pat. Nos. 6,074,394 and 6,503,249; Govari, U.S. Pat. No. 7,060,075; and Ritchey, US published application 20100274121. A navigation system (Trigen Sureshot™ Distal Targeting System, Smith & Nephew, Memphis Tenn. USA) is commercially available. These systems use electromagnetic navigation systems (comprising a field generator that emits a controlled magnetic field, at least one sensor that responds to the magnetic field by generating a signal indicative of the sensor's position relative to the field generator, a computer, and associated software), a drill guide, and a targeting display to show the user the relative locations of the drill guide and the sensor such that the user can align the drill guide to a predetermined position relative to the sensor. Some systems described in the prior art include an electromagnetic sensor located in the implant at a known location relative to the features to be targeted (in the case of IM nailing, the distal locking holes) throughout the targeting procedure. Ritchey, WO2010/129141 describes various methods and apparatus for estimating the travel of a drill bit through a drill guide.

Most modern, widely used, IM nails are cannulated along their length, the cannulation having a circular cross-section and a diameter related to the overall size of the nail. Typical IM nails have various holes and slots, in addition to the locking holes, located along the length of the nail. Typically the nail is implanted by attaching an insertion tool to the proximal end of the nail and passing the nail cannulation over a guide wire. The guide wire is then withdrawn and the nail may be hammered in further, rotated, withdrawn, or otherwise positioned as required using a variety of fittings attached to the insertion tool. In some systems an electromagnetic sensor tool is inserted into the cannulation at a position that is known relative to the locking screw holes.

The systems described by Krause and Govari, and the Sureshot™ system, include a separate drill guide which would typically be held by the surgeon with one hand, while he or she holds a drill in their other hand.

In such systems using a separate drill guide, the drill bit slides through the guide in a direction along the drill bit axis. In prior art systems having a field generator separate from the drill and the drill guide, the drill, drill guide, and drill bit all may move in and out of, and move about within, the measurement range of the field generator. When the field generator is integrated with or attached to the drill guide in a fixed position, as shown in some prior art systems, the drill bit slides in and out of the measurement range of the field generator during drilling.

In many surgical procedures, including IM nailing, it is desirable to position tools with sub-millimetic and sub-degree accuracy (Beadon 2007). Electromagnetic navigation systems can be affected by the presence of certain metals (particularly ferromagnetic and electrically conductive materials) and magnetic fields located in and nearby the measurement range of the field generator (Kirsch 2005; Beadon 2007). Many drills, including commonly used surgical drills, contain ferromagnetic and conductive parts, and may also contain electric motors which may contain magnets and which may generate magnetic fields during operation. Drill bits commonly used in surgery are made of ferromagnetic materials such as hardened stainless steel, which, when moved within the range of the electromagnetic tracking equipment, may cause distortion of the electromagnetic fields and may cause inaccurate tracking measurements. There may also be variations in the particular field generator and environment that affect the accuracy of tracking.

In typical electromagnetic position tracking systems, the sensor coordinate system in which the system reports the position and orientation of a sensor is defined by the relative location and the characteristics of components inside the sensor tool. These are variable in manufacture. For example in a cylindrical sensor tool, the sensor coordinate system as manufactured may have an axis only approximately coaxial with the cylindrical axis. To achieve an accurate known relationship of the coordinate system to the physical shape of the sensor tool, a set of correction factors may be determined by calibrating each individual sensor tool in a calibration fixture at manufacture, and writing the correction factor to a memory device built in to the sensor (Aurora™ Tool Design Guide Rev. 3 Dec. 2005 Northern Digital Inc. Waterloo, Ontario, Canada). This individual calibration and programming process, along with a suitable memory device, generally increases the manufacturing cost of the sensor tool.

When attaching a sensor tool to an implant in order to target features in the implant, the accuracy to which the relative position of the sensor coordinate system and the features is known directly affects the accuracy of targeting. This relative position may be included in a database stored in memory, and recalled if the user correctly indicates the type of sensor and implant being used, provided the database of implant dimensions includes that particular implant. In this case, the manufacturing tolerances of the implant, the sensor tool, and any other component used to position the sensor tool all become direct factors in targeting accuracy. For example with an IM nail, if the sensor tool attaches to the insertion tool which is in turn attached to the proximal end of the nail, as shown in certain embodiments described by Ritchey in patent application WO2010/129141, the manufacturing tolerances of the handle, the distance from the proximal end of the nail to the locking holes, and the sensor tool length may all contribute to targeting variance.

With electromagnetic position tracking systems, measurement errors may occur if external magnetic fields are present or objects made of certain metals are brought into the range of the field generator (Kirsch 2005). Such distortions can be unpredictable and may not be apparent to the user during navigation. For example measurements may appear steady, but be biased several millimeters in a particular direction by the presence of a ferromagnetic tool, such as a surgical hammer, located close to the field generator.

Outputs of typical electromagnetic position tracking systems can include low frequency, high amplitude measurement noise. Such noise can cause measurement values to vary. It is also typical for these systems to occasionally fail to return a valid reading for a sensor which can cause the user display to freeze momentarily until good data is received again. Small, lightweight field generators and small sensors are especially prone to produce orientation data having occasional outlying values.

Finally, in certain cases and with certain types of IM nailing procedures, the preferred practice is to drill through the proximal holes and lock the proximal bone fragment to the nail prior to drilling and locking the distal holes (e.g. see TFN™ Titanium Trochanteric Fixation Nail System; Technique Guide. Synthes GmbH, Oberdorf, Switzerland). In these cases the proximal locking screws block the nail cannulation and make it impossible to install a sensor tool that passes through the cannulation past the proximal locking screws, for example for the purpose of targeting distal locking holes.

The foregoing examples of the related art and limitations related thereto are intended to be illustrative and not exclusive. Other limitations of the related art will become apparent to those of skill in the art upon a reading of the specification and a study of the drawings.

SUMMARY

The invention has several aspects. These aspects may be applied in combination but also have application individually and in sub-combinations. These aspects include without limitation:
- sensor tools;
- tools having integrated field generators;
- methods for measuring distances traversed by tools having integrated field generators;
- tools configured to measure distances traversed and other parameters of position and motion of the tools;
- tools having integrated user interfaces and visual display devices;
- methods for displaying alignment of tools to targets;
- tools configured to display alignment of the tools to targets;
- attachments for calibrating tools having integrated field generators;
- attachments for registering tools having integrated field generators to targets;
- methods for calibrating tools having integrated field generators;
- tools configured with calibration functions;
- methods for registering tools having integrated field generators to targets;
- tools configured with functions for registering the tools to targets;
- methods and apparatus for monitoring the measurement conditions affecting field generators integrated with tools;
- methods and apparatus for filtering measurement data from field generators integrated with tools and interacting with sensors;
- methods and apparatus for determining and optimizing filtering parameters used to filter measurement data from field generators integrated with tools and interacting with sensors;
- tangible media storing computer software which, when executed, causes a processor to perform any of the methods listed above, and;
- methods and apparatus for fixing surgical implants, the apparatus having provisions for installation of electromagnetic sensor tools.

The invention includes, without limitation, the aspects claimed in the appended claims. The invention also includes all other aspects that may be made the subject of additional claims that may be properly presented in future as supported by the present specifications, drawings and claims.

In an example application, the tool is a drill, the feature is a hole in a component which is positioned behind an opaque material, and the objective may be to align the drill with the hole so that the user can drill a hole through the material in line with the hole. For another example the tool may be a driver and the objective may be to align the driver with the feature in order to install a pin or screw through the feature. For another example the tool may be a tool and the feature may be an anatomical feature of a patient. For another example the tool may be a drill and the feature may be a hole in an implant. Some embodiments of the invention are particularly adapted for computer-assisted locking of IM nails, including location of the locking holes in the nail, computer-assisted drill positioning, and real-time intra-operative positioning feedback to the user.

Some embodiments of the invention provide a sensor tool adapted for attachment to a target component having a target feature. Sensor tools according to some embodiments have one or more of the following features:
- fits a range of existing components of a variety of sizes and shapes,
- as required, fits a variety of existing tools or fixtures that may be used with the component for positioning or holding the component;
- is able to be installed quickly and precisely to a unique position relative to the target feature;
- indicates to the user when the sensor is installed in the unique position, and;
- remains in the position throughout the entire drilling procedure, without blocking or otherwise interfering with the target feature.

One example aspect of the invention provides a sensor tool incorporating a tip portion at a distal end, a handle portion at a proximal end and a shaft portion connecting the tip portion and the handle portion. Electromagnetic sensor coils are provided at a fixed position inside the tool near the distal end. The shaft portion may be flexible. The tip portion is adapted to fit and center itself within a cannulation in a component such as an IM nail or other implant. A single sensor tool may have a tip that is self-centering within cannulations having various diameters within a range of diameters.

In some embodiments the handle portion is adapted to engage features of existing insertion tools that are normally used to insert IM nails or other implants. Such engagement may hold the sensor tool in a predetermined fixed position relative to the nail or other implant in all 6 degrees of freedom until it is removed. The handle portion may be further adapted to create an audible sound (such as a click) when the sensor tool is fully engaged to the insertion tool. The handle portion may further be adapted to create a different indication to the user that it is fully engaged, such as a vibration, or a change in shape or position of a part of the handle portion.

In some embodiments the shaft portion has selected flexibility sufficient to allow the sensor tool to be inserted into IM nails or other components that are not straight. The shaft portion has a selected length to match a predetermined range of IM nail lengths, such that the distal end of the tool does not block a distal locking hole of the shortest nail in the range, and such that the sensor element is within a predetermined distance (related to the range of the electromagnetic navigation system) of the locking holes when used in the longest nail in the range.

Another aspect of the invention provides a navigation unit incorporating a field generator. The navigation unit may be integrated with a tool or adapted for attachment to a tool.

Navigation units according to some embodiments have one or more of the following features:

- work with a variety of existing tools, including those having electric motors and containing parts made of ferromagnetic material,
- can be easily attached, removed from, and reattached to the tool such that an axis of the tool and a point on that axis have the same position and orientation relative to the field generator each time the unit is attached, and in the case of the tool being a drill, is able to hold the field generator static relative to the drill axis and the drill tip point, such that the only freely allowed relative motion between the field generator and the drill bit is rotation about the drill axis.
- can be attached in positions offset from the tool axis, to give the user a clear view of the working area and to provide space around the tool to allow the user to work with the tool without removing the field generator,
- is light and small enough so as not to interfere with handling and positioning of the tool, and;
- has the capability to record, store, and use a correction map to correct for tracking measurement distortions produced by the tool being mounted close to the field generator.

An example embodiment provides a drill-mounted electromagnetic field generator and mounting structure unit adapted to attach to a drill quickly, easily, temporarily, and precisely in a known position relative to a drill axis before or during use. The mounting structure is designed such that the field generator is temporarily fixed relative to a drill axis about which a drill bit rotates and a point on the axis at the drill tip. In an example embodiment the mounting structure comprises a drill chuck, a housing portion enclosing the drill chuck, a rigid extension arm extending away from the housing portion and having a distal end at a predetermined distance from the axis, and a field generator mounting portion attached to the distal end of the extension arm. The drill chuck is adapted to attach to a drill in at least one rotational position about the drill axis, and to hold a drill bit.

In accordance with another aspect of the invention, the mounting structure is adapted such that the field generator component may be removed and replaced precisely to the same location in the structure as described above. In some embodiments the structure also encloses and isolates the field generator, for example to isolate a non-sterile field generator in a sterile surgical field.

In accordance with another aspect of the invention, the mounting structure includes a drill bushing rigidly connected to the field generator mounting portion and having a close running fit to the shank of the drill bit, thereby limiting the possible relative movement between the field generator and the drill axis.

In accordance with another aspect of the invention, there is provided a method of determining the position of a tool axis and a point on the tool axis relative to a field generator, the method comprises:

- connecting the field generator unit to an electromagnetic navigation system, such that the position of the field generator may be recorded relative to a fixed reference frame,
- holding the tool axis in a fixed position relative to the fixed reference frame,
- rotating the field generator about the tool axis and recording the field generator position at a number of rotational positions;
- calculating the position of the tool axis relative to the field generator by determining the least variant axis of rotation of the field generator, and;
- defining a point on the axis at a predetermined position relative to the field generator, or if the tip of the tool lies on the axis, by using a pivot calibration method to define the point coincident with the tip of the tool.

In accordance with another aspect of the invention, selected motions and parameters of motion of a point on the tool axis relative to a target component are recorded and analysed and used advantageously, optionally in conjunction with other recorded parameters, to advise the user and trigger selected actions related to the movement and state of the tool.

In accordance with another aspect of the invention, there is provided a method of calibrating the navigation system to correct for measurement errors caused by the presence of portions of a tool within the measurement volume of the navigation system, and portions of a tool positioned close to the field generator, the method comprising the steps of:

- attaching the tool to the field generator and recording the position of a sensor as it is moved through a series of known positions,
- calculating the difference between the known position and the recorded position for each known position in the series, thereby creating a lookup table of measurement correction values,
- interpolating between correction values in the lookup table to create a continuous function of correction value versus sensor position, and
- reading the current position of the sensor during navigation, finding the closest corresponding measurement correction factors from the lookup table, or alternately calculating the correction values from the continuous function, and applying the correction values to the current position of the sensor to create a corrected current position of the sensor for use in navigation.

In an embodiment of the invention the lookup table is generated by mounting a drill, drill chuck, drill bit, and field generator assembly in a fixture on a coordinate measuring machine, moving a sensor through the series of known positions programmed into the coordinate measuring machine, and storing the lookup table in a memory device integrated with the field generator.

In another embodiment of the invention, the lookup table is generated during use with the specific sensor and target component being used by installing a registration tool onto a drill, drill chuck, drill bit, and field generator assembly, inserting a sensor into an IM nail, inserting the registration tool into a distal locking hole in the nail such that the drill bit axis and the hole axis are coincident, rotating the assembly about the coincident axes, recording a hole axis definition for each location recorded around the drill axis, interpolating between the locations to increase the resolution of the lookup table or to create a continuous function of hole axis definition versus position about the drill axis, and storing the lookup table or function in the navigation system memory for use during navigation. Alternately any device that can be calibrated from measurement data and produce corrected sensor readings can replace the function of a lookup table used in the exemplary embodiment. The correction can with equal effect be applied to the calibrated position of the drill hole or the sensor readings.

To allow a user to navigate and align a tool with one hand, and not have to look away from the work area to view navigation and alignment information and feedback or reach away from the work area to send operational commands to the navigation system, a visual display and user interface unit may be advantageously mounted on or near the tool and generally move with the tool.

For use in the sterile field, surgical drills are typically designed to be steam sterilized (autoclaved). However electronic display and touchscreen devices most suitable for the exemplary surgical application and available at reasonable cost generally cannot withstand steam sterilization. It is possible to use lower temperature sterilization processes such as ethylene oxide sterilization for items containing sensitive electronic components, but this still generally increases the cost of the electronic components, and in the case of ethylene oxide sterilization the process takes longer and may present occupational health and safety concerns due to residual chemicals. For these reasons steam sterilization is the preferred method in most hospitals, and accordingly a display and user interface unit containing electronic components and located on or near a tool in the sterile field is advantageously detachable from the tool so that it can be sterilized separately by an alternate method, or isolated in a sterile drape or bag, and then reattached to the tool in the sterile field.

When the user interface unit is integrated with the tool as described above, the different orientations of the tool that may be used may require adjustability of the user interface unit relative to the tool to allow adjustment to a position where the display screen is easily visible to the user. As the display is moved relative to the drill, and the drill is used in various orientations relative to the target, it is an advantage if the image shown on the display can automatically change field of view, magnification, and/or orientation to best represent the target area.

To align a tool with a selected target, the user typically needs to first find the target within the general target area and possibly locate the desired target from among a group of possible targets, in which case a large field of view is advantageous. Then when close to the desired target the user typically makes fine adjustments of the tool position to within a suitable tolerance, in which case a smaller field of view that is aligned with, magnified and centered on the chosen target is advantageous.

Accordingly, some embodiments of the invention provide a user interface unit attached to a tool and having one or more of the following features:

mounted on or near the tool, such that it is generally within the user's field of view while looking towards the working area of the tool;

adapted to fit and work with a variety of existing tools;

attachable and detachable by hand without the use of tools;

visible, or may be adjusted to be visible, to the user in various tool orientations;

can receive input from the user and relay information and commands to and from the navigation system;

automatically adjusts the image orientation, field of view, and/or magnification using information on the display orientation, patient position, and/or tool movement relative to the target, and;

displays to the user the current position and orientation of the tool relative to the target, and indicates to the user when alignment to the target is within selected limits based on selected parameters, where the limit of any parameter may be a function of other parameters.

Another aspect of the invention provides an electronic display and user interface unit with mounting apparatus adapted for installation on a tool, wherein the user interface unit may be removed for separate sterilization or draping, and reinstalled easily in the sterile surgical field.

Another aspect of the invention provides an electronic display and user interface unit with an adjustable mounting mechanism allowing the unit to be moved relative to the tool to be visible in various tool positions relative to the user's point of view.

In one embodiment the mounting mechanism comprises a swivel joint with an axis about which the user interface unit can rotate, a second swivel joint having a second axis about which the user interface unit can rotate, and a releasable joint between the user interface unit and the mounting mechanism designed to accommodate a flexible film material or drape material between joining surfaces of the releasable joint.

Some embodiments comprise at least one sensor that generates a signal indicative of the position of the user interface unit relative to the direction of gravity.

Some embodiments comprise sensing apparatus that generates a signal indicative of the position of the user interface unit relative to a field generator.

Another aspect of the invention provides a method of comparing and indicating to the user the current relative position of a tool axis and a target axis having a fixed position relative to a sensor, comprising the steps of:

Monitoring the current position and orientation of the tool axis and a point on the tool axis relative to the sensor;

Calculating the normal distance from the target axis to the point and determining if the distance is within a selected limit, and if so displaying a first indicator, and;

Calculating the intersection point of the tool axis and a plane normal to the target axis and passing through a selected point along the target axis, Calculating the normal distance from the target axis to the intersection point and determining if the distance is within a selected limit and if so, and the first indicator is displayed, displaying a second indicator.

The distance measure between the point and the target axis may be any that consistently reflects tip-axis distance. In some embodiments the point is coincident with the tool axis and the tip of the tool.

Another aspect of the invention provides an alternate method of comparing the current relative position of a tool axis and a target axis having a fixed position relative to a sensor, comprising the steps of:

Monitoring the current position and orientation of the tool axis relative to the sensor, Calculating a first intersection point of the drill axis and a first plane normal to the target axis and passing through a first selected point along the target axis, Determining if the first intersection point is within a selected first tolerance zone around the target axis, and if so displaying a first indicator, Calculating a second intersection point between the tool axis and a second plane normal to the target axis and passing through a second selected point along the target axis, and Determining if the second intersection point is within a selected second tolerance zone around the target axis and if so, and the first indicator is displayed, displaying a second indicator.

In order to minimize cost, risk of error, reliance on accurate manufacturing tolerances, accurate stored dimensions, individual sensor tool calibration, and consistent sensor, field generator, and environment characteristics, it is advantageous to directly register a target feature to a sensor using the particular tool and field generator assembly, sensor, target component, and any component insertion or holding tool being used. Some embodiments of the invention provide a registration tool having one or more of the following features:

fits target features within a range of sizes;
fits the tool and navigation unit as assembled for use, and;
holds the navigation unit accurately at a known relative position to the target feature in selected degrees of freedom during the registration measurement.

Another aspect of the invention provides a registration tool comprising a body portion adapted to slide over a portion of a tool, for example a sae or drill, and a tip portion adapted to fit within a target feature in a target component, thereby fixing the position of the registration tool relative to the feature in selected degrees of freedom.

In one embodiment, the registration tool has a sliding fit over a drill bit such that when installed on the drill bit the tip portion has an axis coincident with the longitudinal axis of the drill bit, the target feature is a cylindrical hole having a diameter within a predetermined range and a centerline of the cylinder, and the tip portion is adapted to closely fit the hole such that when the tip portion is installed in the hole the tip portion axis and target hole axis are coincident, thereby fixing the relative position between the hole and the registration tool in all six degrees of freedom except rotation about and translation along the coincident axes. The tip portion may include at least one resilient element adapted to provide a tight fit in different holes having diameters within a predetermined range of diameters. In some embodiments the fit is an interference fit and the interference is selected in conjunction with the stiffness of the resilient element and the friction between the resilient element and the hole or other feature to allow the registration tool to be installed in and removed from the feature by hand.

In another embodiment, the registration tool has a sliding fit over a drill bit and engages a target hole having a revolved surface about a hole axis within predetermined size and shape limits, such that drill bit axis and the hole axis are coincident, thereby fixing the relative position between the hole and the registration tool in all six degrees of freedom except rotation about and translation along the coincident axes.

In another embodiment, the registration tool has a sliding fit over a drill bit and engages a target hole having a revolved surface about a hole axis within predetermined size and shape limits, such that drill bit axis and the hole axis are coincident and the registration tool further engages a second feature fixed relative to the target hole such that the relative position between the hole, the second feature, and the registration tool is fixed in all six degrees of freedom.

Another aspect of the invention provides a method of registering the navigation system to at least one target feature of a target component by measuring the target feature position relative to a sensor. In one embodiment, the method comprises the steps of:

attaching a sensor component of a navigation system to a target component such that the sensor is fixed in all six degrees of freedom at a position relative to a target feature of the target component, but wherein the relative position is not previously known to a sufficient degree of accuracy,
attaching a registration tool to a tool and field generator assembly such that an axis of the registration tool is at a known location relative to the field generator,
temporarily fixing the registration tool and assembly to the target feature of the target component such that the registration tool axis is at a known spatial relationship to the target feature,
recording the position of the sensor relative to the field generator,
calculating the relative position of the feature to the sensor, and
storing the relative position of the feature to the sensor into the memory of the navigation system.

In one embodiment of the invention the relative position of the feature to the sensor is defined as a line expressed in the coordinate system of the sensor and representing a target axis, and is recorded by averaging a selected number of position measurements.

Some embodiments of the invention provide controlling and signal processing methods, apparatus, and software having one or more of the following features. The controlling and signal processing methods, apparatus, and software may advantageously:

Detect measurement distortions during navigation;
Detect externally generated magnetic fields during navigation;
Monitor overall measurement noise and detect outlying data;
Filter the measurement data to minimize signal noise to create a smooth display;
Filter the data to exclude low frequency high amplitude outlying data;
Present the remaining valid measurement data to the user;
Warn the user of potentially inaccurate data and high rates of outlying data, and;
Use detected information about the measurement data, measurement distortions, and externally generated magnetic fields to optimize filtering parameters.

Another aspect of the invention provides a method of detecting tracking measurement distortions and externally generated magnetic fields during navigation, the method comprising the steps of:

Tracking the position of a first sensor and simultaneously monitoring the position of a reference sensor, wherein the first sensor may move relative to the field generator and the reference sensor is mounted in a fixed position in selected degrees of freedom with respect to a field generator,
Comparing selected parameters of the deviation in position and/or orientation of the reference sensor (which may include position, orientation, and their time derivatives, or any function thereof) to predetermined threshold values,
Activating warning functions, modifying selected characteristics of the navigation system and the filtering and processing of navigation data, including the display of navigation information to the user, when the selected parameters or combinations of the parameters fall within a range of predetermined values or exceed threshold values.

In an embodiment data from the reference sensor is compared to its known, calibrated position and orientation. The sum of the absolute values of the difference between the reference sensor position reading and the calibrated position is compared to a threshold. The same procedure is applied to the orientation expressed as a vector of quaternions with a separate threshold. An interference condition is recognized if either the position or orientation derived quantity exceeds its associated threshold value. The reference sensor may additionally self-calibrate automatically upon startup of the navigation system and/or upon a user-issued command. Data from the reference sensor may additionally be used to help determine certain states of a tool, such as motor on or off, and certain conditions of use of the tool, such as motor speed range and engaged or not engaged with the target.

Another aspect of the invention provides a method of filtering measurement data generated by the navigation system to detect and exclude or correct data that is altered by interference or measurement errors, the method comprising the steps of:

Monitoring the current position and orientation of a first sensor which may move relative to the field generator, calculating their time derivatives, and calculating selected characteristics of the position and orientation data from the first sensor over a selected time period, Comparing selected characteristics to predetermined threshold values, Deleting the current position and orientation reading if certain selected characteristics or combinations of characteristics exceed predetermined threshold values, Monitoring the frequency of deleted position and orientation readings over a selected time period preceding the current reading, and if this frequency exceeds a selected threshold, displaying to the user an indication that current data is unreliable, and, optionally, displaying to the user an estimate of current position and orientation that is calculated from position and orientation data gathered over a selected time period.

In an embodiment of the invention, outlying sensor readings are determined from the sum of the absolute values of the time derivative of the position vector and the time derivative of the orientation vector expressed as quaternions. Each value is compared with an associated threshold and when either threshold is exceeded the sensor reading is identified as an outlier. Once a certain number of consecutive outliers or missing readings have been identified an appropriate indicator is shown on the user interface.

In another embodiment of the method, the reference sensor is used to provide a correlated measure of interference noise and used to remove interference noise in the first sensor. Noise cancellation may be performed with a linear adaptive noise cancellation technique, or any other cancellation method that uses a noise reference source as input.

In yet another embodiment of the method, a Kalman filter is applied to the sensor readings. Any other adaptive method that uses the statistics of the input signal to adjust its filter behavior, such as recursive Bayesian estimation methods, may also be applied.

In certain variations of the exemplary surgical procedure, there may be a need to proximally lock an IM nail before distal locking is complete. In these cases it is an advantage if a sensor tool may pass through the length of the nail cannulation when a proximal locking apparatus is in place. Accordingly in another aspect of the invention, there is provided an apparatus and method to lock a bone fragment to an IM nail in such a way as to maintain, temporarily or permanently, an open passage through the cannulation along the longitudinal centerline of the nail. In an embodiment of the invention the locking apparatus is a fenestrated drill bit also adapted to drill through the bone. In another embodiment the locking element is a fenestrated stud inserted temporarily after drilling, engaging the bone and passing through the nail, before installation of the permanent locking element. In another embodiment the permanent locking element is fenestrated. In another embodiment of the invention the locking element is a stud with an expanding element at one end adapted to engage one cortex of a bone and the inner bore of a locking hole in an IM nail implanted in the bone.

One example embodiment is particularly adapted for computer assisted IM nailing, with particular focus on the step of drilling through the bone in line with selected cross holes in the nail (known as locking holes) to allow installation of locking screws. In this exemplary embodiment the apparatus comprises:

a surgical drill with a ferromagnetic drill bit;

a small, lightweight field generator mounted to the drill, and with a portion of the drill bit lying within the measurement range of the field generator; and;

a sensor tool that generates a response indicative of its position relative to the field generator and adapted for precise insertion into an implant during surgery to a predetermined location fixed in all 6 degrees of freedom relative to selected features of the implant.

A display screen is provided to display alignment information to a user. In some embodiments the display screen is mounted to or in close proximity to the drill. In some embodiments the display screen is mounted on the drill in a position relative to the drill that is fixed in 4 degrees of freedom and adjustable to various positions in two degrees of freedom relative to the drill.

The embodiments shown are particularly adapted for use, along with an electromagnetic navigation system, in computer assisted IM nailing, in particular the step of drilling through the bone and selected cross holes in the nail (known as locking holes) to allow installation of the locking screws.

In addition to the exemplary aspects and embodiments described above, further aspects and embodiments will become apparent by reference to the drawings and by study of the following detailed descriptions.

BRIEF DESCRIPTION OF THE DRAWINGS

The included drawings illustrate non-limiting example embodiments of the invention.

FIG. 6 is a section view through the exploded view of FIG. 3, looking at the approach of the sensor tool to the insertion tool during installation according to the exemplary embodiment.

FIG. 6a is a section view through the assembly of FIG. 4, looking at the engagement of the exemplary sensor tool to the insertion tool according to the exemplary embodiment.

FIG. 6b shows another example of a snap-fit arrangement for a sensor tool.

FIG. 6c is a section view taken from FIG. 6b showing a snap-fit sensor handle engaged with a cannulated bolt having a groove.

FIG. 6d is a section view taken from FIG. 6b showing a rotational constraint arrangement for a sensor tool to an implant and insertion handle assembly.

FIG. 6e is a detail view showing the proximal portion of a cannulated bolt with an extended cap, a groove, and a countersink.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Different aspects of the invention and their presently preferred embodiments will be better understood by reference to the detailed disclosure below and/or the accompanying drawings. Where the same reference numbers are used in different drawings, the reference numbers refer to the same or similar parts.

As used herein "distal", when referring to a drill and attached components, refers to the direction leading further away from the user and towards the drill bit tip, and proximal as used herein is the opposite direction to distal. As used herein "distal", when referring to an IM nail and components attached to it, refers to the direction leading further away from the insertion tool, and proximal as used herein is the opposite direction to distal.

As used herein, 'navigation system' is a combination of an electromagnetic field generator, at least one electromagnetic sensor, and a controller, which may comprise a computer, connected to the field generator and sensor. The controller is configured to determine the position and orientation of the sensor element relative to the field generator. An example of a suitable navigation system is an Aurora™ system made by Northern Digital Inc. (Waterloo, Ontario, Canada), which can be suitably modified and controlled by customized software for use in applications as described herein. Other suitable navigation systems are available from Ascension Technology Corporation, 107 Catamount Drive, Milton, Vt. 05468 USA.

Figure 1:
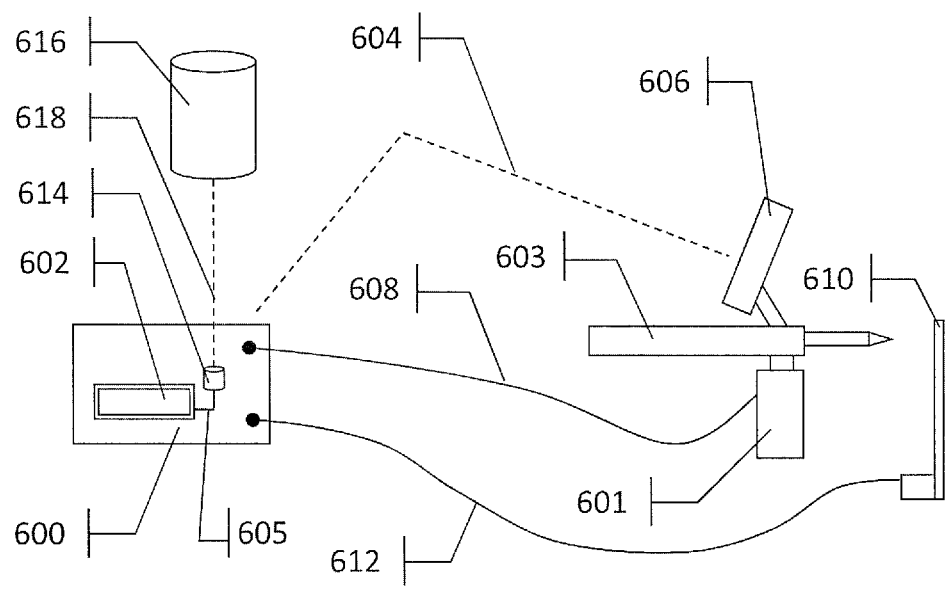
FIG. 1 is a block diagram illustrating a system according to an example embodiment of the invention.

FIG. 1 is a block diagram illustrating a system according to an example embodiment of the invention. Console 600 includes processor and power supply components of an electromagnetic navigation system. Console 600 may provide additional processing and communication components particular to an application, such as IM nailing. Charging dock 602 receives and charges user interface unit 606 when not in use. When in use, user interface unit 606 and navigation unit 601 are attached to tool 603. Unit 601 includes a field generator and at least one reference sensor that communicates with console 600 via cable 608. User interface unit 606 communicates with console 600 via wireless communication link 604. Sensor tool 610 communicates with console 600 via sensor cable 612. Memory 614 accessible to console 600 includes dimensions, features and graphic data models of components, and also measurement correction maps, lookup tables, parameters sets, software, firmware, and the like.

Database 616 contains dimensions, features and graphic data models of components, and also measurement correction maps, lookup tables, parameters sets, software, firmware, and the like and is stored in an external memory device. Database 616 may be linked via communication link 618 to memory 614 to update the contents of memory 614. Communication link 618 may comprise, for example, a wired, internet or wireless link or some combination thereof.

Software, firmware, and data stored in user interface unit 606 may be updated via communication link 604 and via connection 605 from charging dock 602 to memory 614. Software, firmware, and data stored in unit 601 may be updated via cable 608. In various other embodiments in which tool 603 includes an electrical power source, such as a battery, cable 608 may be replaced with a wireless communication link for control signals between console 600 and unit 601, and a wire supplying power from tool 603 to unit 601. In various other embodiments sensor cable 612 may be replaced with a power source, signal amplifier, and wireless communication unit included in sensor tool 610, and a wireless communication link from sensor tool 610 to console 600. Non-limiting examples of suitable wireless links are Bluetooth™ and WiFi local area wireless communication systems.

One aspect of the invention provides a sensor tool for use with a navigation system. The sensor tool comprises an elongated member having a self-centering tip portion containing a sensor element. A snap fit mechanism is provided to hold the sensor tool in place in a component (e.g. an IM nail) so that the sensor element has a known geometrical relationship to a feature on the component (e.g. a locking hole).

FIGS. 1a through 6, show an example sensor tool 10. The illustrated sensor tool 10 may be used in IM nailing procedures, for example. Example sensor tool 10 includes several desirable features as described below. Each feature may be advantageous individually or in combination with some or all of the other features described. Other embodiments within the scope of the invention may include a subset of the advantageous features described in the example embodiment.

One desirable feature of sensor tool 10 is that the distal tip portion is self-centering in a range of different cannulation diameters. The self-centering characteristic may be provided by resiliently flexible members incorporated in the tip portion that are biased radially outwards to a maximum diameter, but may be resiliently compressed radially inwards to a range of smaller diameters all concentric with the maximum diameter. For example the self-centering characteristic may be provided by flexible members 186 (shown in FIGS. 2 and 2a) that are arch-shaped when viewed in a plane passing through the longitudinal centerline of sensor tool 10 and that are spaced angularly about a centerline of the tip portion.

Another desirable feature of sensor tool 10 is that sensory feedback is provided to the user when sensor tool 10 is properly installed in a component, such as an implant. The sensory feedback may be provided by a snap-fit mechanism. The snap-fit mechanism may provide tactile and/or audible feedback to the user upon engagement exclusively in the properly installed position. A snap-fit mechanism may be provided between the sensor tool 10 and a component, such as an implant, or between the sensor tool 10 and an insertion tool affixed to the component. A snap fit mechanism may be provided by way of a suitable detent mechanism. For example a snap-fit mechanism may be provided by flexible tabs 192 shown in FIGS. 6 and 6a engaging grooves 195.

Another desirable feature of sensor tool 10 is its fixed length and single-piece finished construction which allows the user to install sensor tool 10 with precision to a unique, predetermined position relative to a component in a single motion without adjustment or reference to graduation markings or the like to select the correct installation position. For example sensor tool length 176 shown in FIG. 1a determines the position of tip portion 154 relative to the assembly of nail 37 and insertion tool 39 (depicted in FIG. 3) along the centerline of nail 37.

Figure 1A:
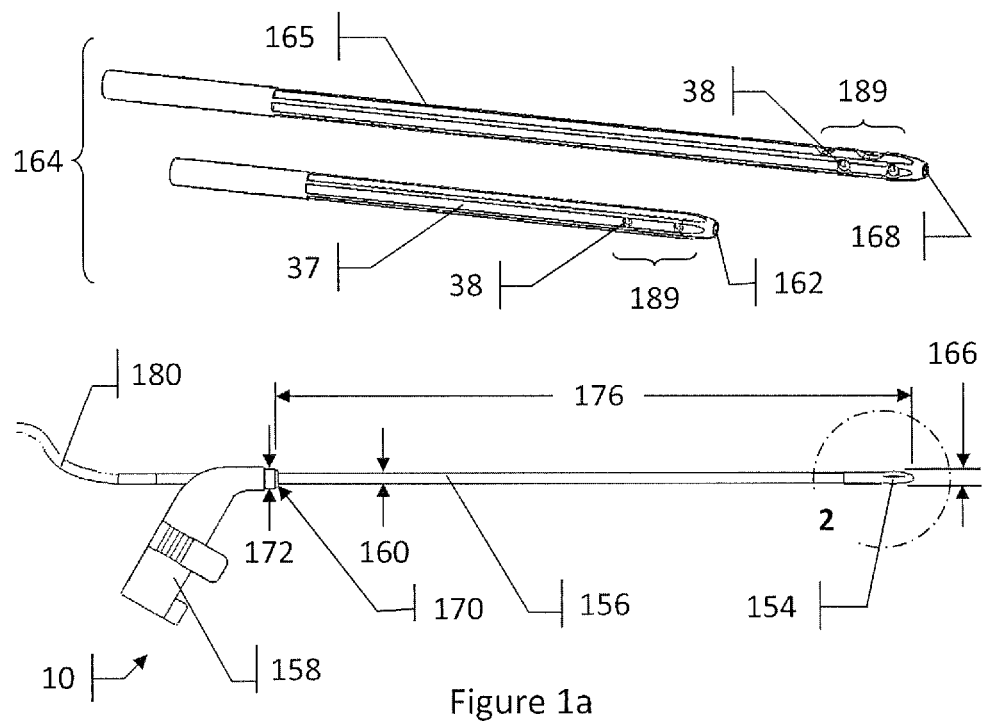
FIG. 1a shows an example sensor tool according to one embodiment of the invention and a set of IM nails with which the sensor tool may be used.

FIG. 1a, shows a sensor tool 10 and a set of IM nails 37 and 165 (collectively or generally set 164 or IM nails 164) with which the sensor tool may be used. One nail in set 164 may have different characteristics from another, for example a different length, cannulation diameter, or a different arrangement of features such as slots and holes. Each IM nail in set 164 has at least one distal locking hole 38 which may vary in size and location from one nail to another in set 164, and may be the only distal feature of interest, or may be part of a group of distal locking holes 189 as shown. For the purposes of this description, if group 189 includes more than one hole or feature that will be drilled through, hole 38 is defined as the most proximal hole of group 189.

Sensor tool 10 has tip portion 154 at its distal end, shaft portion 156, and handle portion 158 at its proximal end. The shaft diameter 160 of shaft portion 156 is less than or equal to the minimum cannulation diameter 162 (visible in FIG. 5) present in set 164. For example, shaft diameter 160 in some cases is in the range of three to four millimeters. Tip diameter 166 is selected to be equal to or slightly greater than the maximum cannulation diameter 168 present in set 164. Shoulder 170 has shoulder diameter 172 which is greater than bolt cannulation diameter 174 of cannulated bolt 173 (both shown in FIG. 5). Length 176 from shoulder 170 to the distal end of sensor tool 10 is selected to be less than the minimum locking hole distance 178 (shown in FIG. 4) present among the nails in set 164, so that hole 38 remains clear for drilling through.

Figure 2:
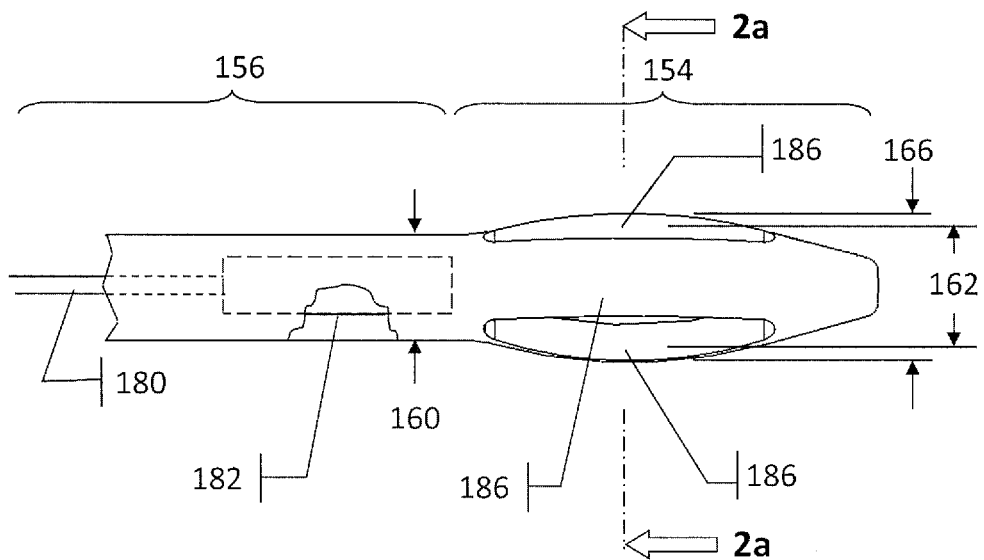
FIG. 2 and FIG. 2a show detail of the tip portion of the exemplary sensor tool.
Figure 3:
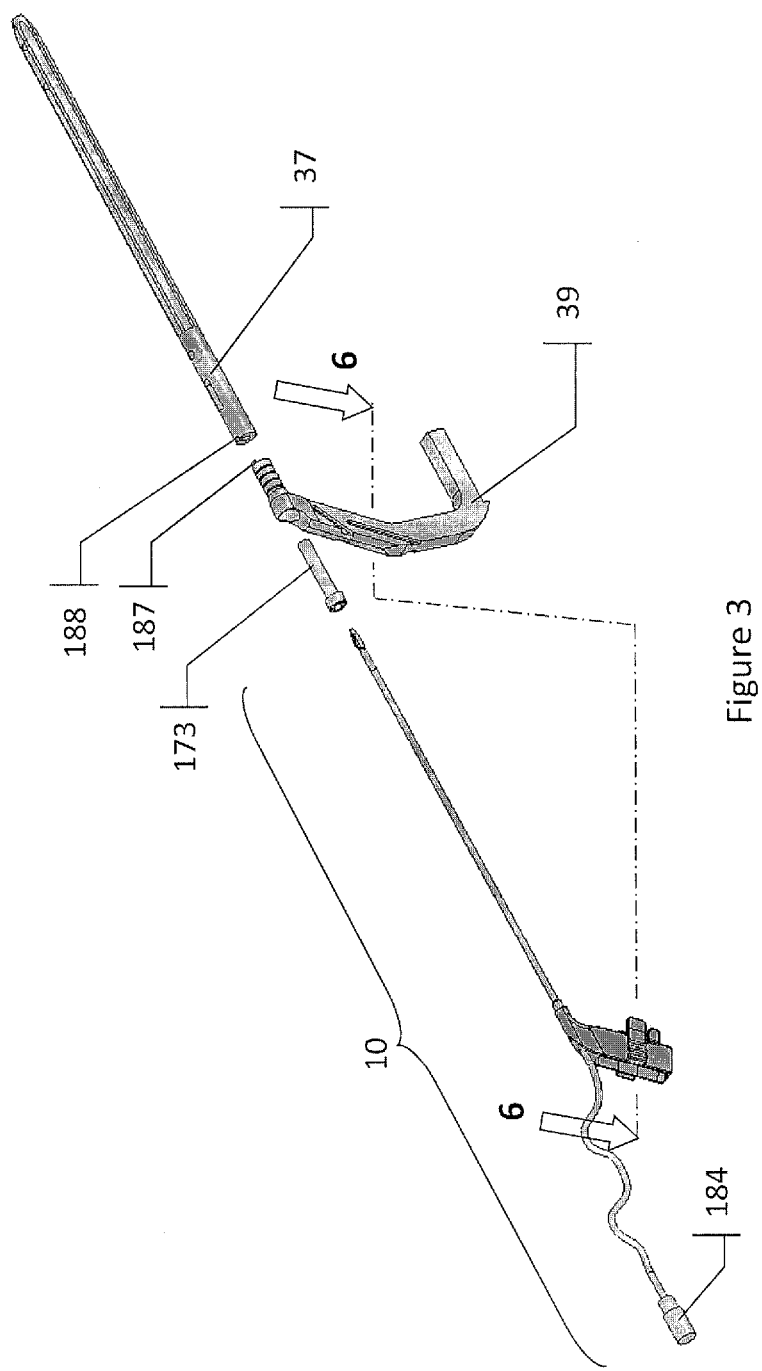
FIG. 3 is an exploded view showing an insertion tool, cannulated bolt, IM nail, and the exemplary sensor tool.

Referring to FIG. 1 and FIG. 2 together, sensor wire 180 extends from sensor element 182 embedded inside sensor tool 10 and connects to the navigation system (not shown) via connector 184 (visible in FIG. 3). Sensor tool 10 may be injection moulded from medical grade plastic, for example ABS or PEEK, and may be assembled and bonded together from two or more parts to form a solid unit in which sensor element 182 is embedded and held in a fixed position within sensor tool 10 with the longitudinal axis of sensor element 182 lying approximately collinear with the common longitudinal axis of tip portion 154 and shaft portion 156.

An example of a suitable sensor element 182 is a Mini 6 DOF sensor from Northern Digital Inc., Waterloo, Ontario, Canada, part number 610029. This sensor is approximately 1.8 millimeters in diameter by nine millimeters long. In an alternate embodiment sensor 10 may incorporate a battery, amplifier, analog to digital converter, and wireless transmitter to send signals wirelessly to the navigation system. Some or all of these components may be housed in handle portion 158.

Figure 2A:
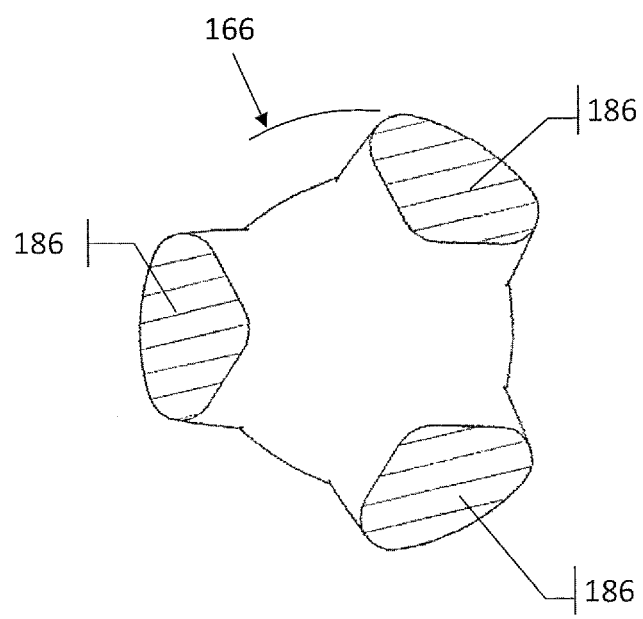

FIGS. 2 and 2a show tip portion 154 of sensor tool 10 in detail. As best seen in FIG. 2a, flexible segments 186 all have the same cross section and shape and are evenly spaced about the common longitudinal axis of tip portion 154 and shaft portion 156. Flexible segments 186 are designed to flex within the elastic range of their material such that tip diameter 166 may be compressed down to minimum cannulation diameter 162 without breaking or permanently deforming, so that sensor tool 10 may be removed, cleaned and re-sterilized, and reused if desired. Sensor element 182 is embedded in sensor tool 10 near tip portion 154. Since flexible segments 186 compress radially inwards evenly when tip portion 154 is in a cylindrical bore having a diameter less than tip diameter 166, sensor element 182 is centered within the cannulation of any nail in set 164 when tip portion 154 is inserted into the nail. Shaft diameter 160 is also shown.

One of ordinary skill in the art will recognize that a variety of other constructions may be chosen to provide the self-centering characteristic of tip portion 154, for example flexible segments 186 may be replaced with a series of flexible vanes or tip portion 154 may be a cylinder having at least one relief slot allowing the cylinder to be compressed down to a smaller diameter.

With reference to FIG. 3, in accordance with an embodiment of the invention, nail 37 which is selected from set 164 (See FIG. 1a) is shown in an exploded view with insertion tool 39 and cannulated bolt 173, which may be used with all nails in set 164 to insert and position the nail in a patient's bone. Selected nail 37 is attached to insertion tool 39 using cannulated bolt 173 which threads into nail 37. Tang 187 of insertion tool 39 engages slot 188 at the proximal end of nail 37, thereby fixing nail 37 in all six degrees of freedom relative to insertion tool 39, and sensor tool 10 may be inserted through cannulated bolt 173 and into the cannulation of nail 37. Connector 184 is also shown.

Figure 4:
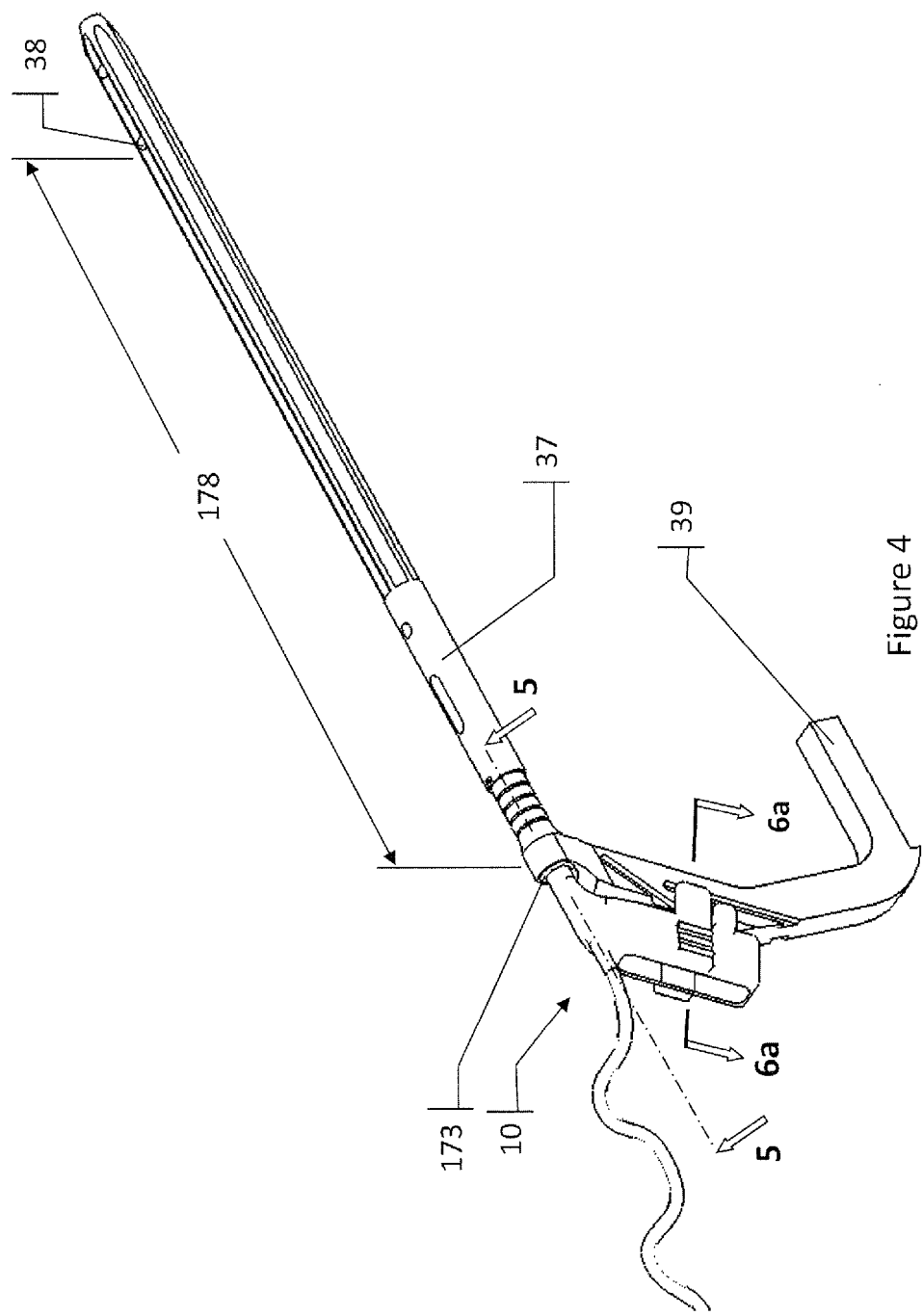
FIG. 4 shows the components of FIG. 3, assembled for use in the exemplary embodiment of the invention.

With reference to FIG. 4, the exploded view of FIG. 3 is shown assembled with sensor tool 10 installed and showing nail 37, insertion tool 39, and cannulated bolt 173. Minimum locking hole distance 178 extends from the contact point of shoulder 170 and cannulated bolt 173 (as seen in FIG. 5) to the proximal edge of distal locking hole 38, which is the most proximal feature that will be drilled through.

Figure 5:
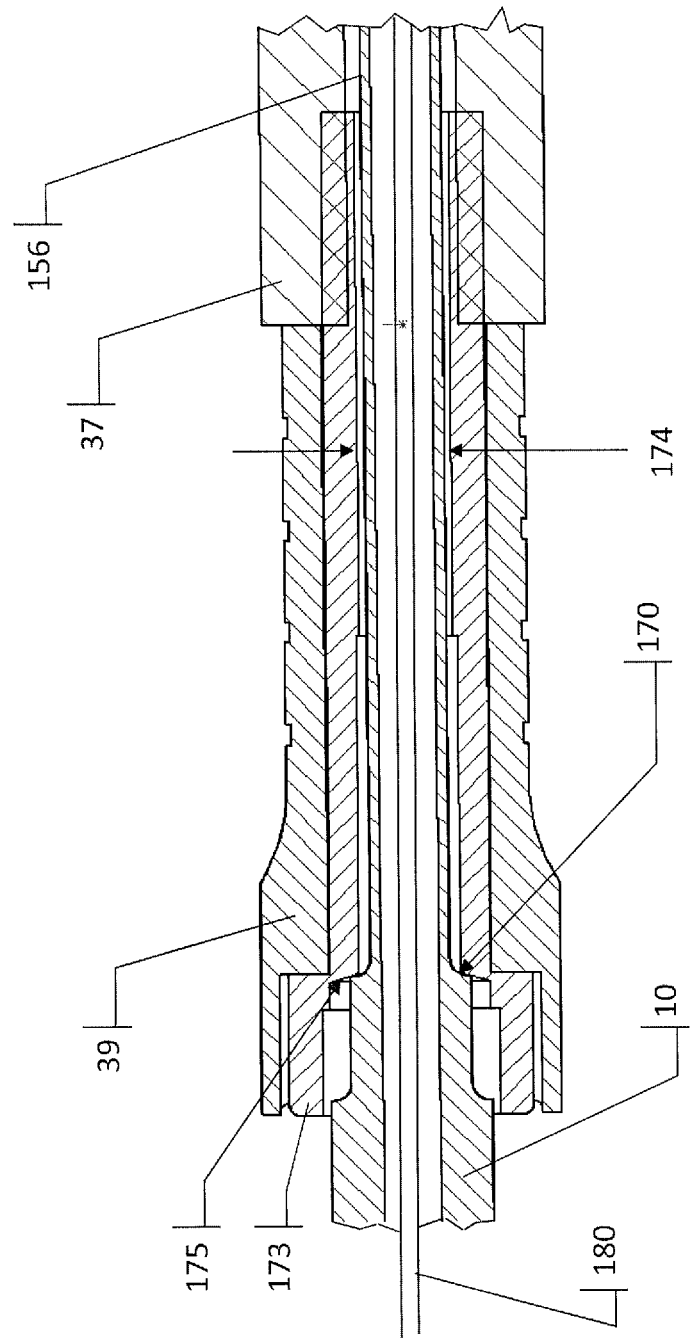
FIG. 5 is a section view through the assembly of FIG. 4 showing the engagement of the sensor tool to the cannulated bolt according to the exemplary embodiment.

FIG. 5 is a partial section view taken from FIG. 4 on a plane through the longitudinal centerline of cannulated bolt 173. When sensor tool 10 is fully inserted into the assembly of nail 37, insertion tool 39, and cannulated bolt 173, shoulder 170 contacts countersunk surface 175 of cannulated bolt 173. When full contact is maintained between the circular edge of shoulder 170 and the conical surface of countersunk surface 175, sensor tool 10 is fixed in translation along the axis of nail 37. Bolt cannulation diameter 174, shaft portion 156 and sensor wire 180 are also shown.

Shaft portion 156 may be flexible with a flexibility sufficient to allow the sensor tool to be inserted into IM nails or other components that are not straight.

FIGS. 6 and 6a illustrate engagement of sensor tool 10 to insertion tool 39. FIG. 6 is a section view through handle portion 158 of sensor tool 10 and also through insertion tool 39, taken from FIG. 3 in the area of grips 197, with sensor tool 10 approaching but not yet engaged with insertion tool 39. FIG. 6a is a section view taken from FIG. 4, similar to FIG. 6 but with sensor tool 10 in its installed position, engaged with insertion tool 39. Referring to FIG. 6, gap 198 is less than tool width 191 so that as sensor tool 10 is pushed distally into position, flexible tabs 192 are forced to spread outward to pass over insertion tool 39. When surface 193 of sensor tool 10 contacts top surface 194 of insertion tool 39, flexible tabs 192 snap into groove 195 as shown in FIG. 6a, creating an audible snap sound and a vibration that can be felt by the user through grips 197 when sensor tool 10 reaches its fully installed position.

Referring to FIG. 6a, flexible tabs 192 are designed to have an interference fit with edge 196 of groove 195 so that in the installed position, deflected gap 199 is greater than gap 198 and flexible tabs 192 are flexed outwards a predetermined amount within the elastic range of the material, and thereby create a distally directed seating force on sensor tool 10 against insertion tool 39 which is reacted at top surface 194 and at the contact of shoulder 170 to countersink surface 175 of cannulated bolt 173 (seen in FIG. 5). The interference fit of flexible tabs 192 against edge 196 also creates a centering force preventing rotation of sensor tool 10 about the longitudinal axis of cannulated bolt 173 (see FIG. 5). Sensor tool 10 is thereby held fixed in all six degrees of freedom relative to insertion tool 39, which in turn is fixed in all six degrees of freedom relative to nail 37. Referring also to FIG. 1a and FIG. 2, since sensor element 182 is fixed within sensor tool 10 at a known location relative to shoulder 170 and is centered within the nail cannulation having a diameter within the range of diameter 162 to diameter 168, sensor element 182 is thereby held in a known fixed position and orientation relative to nail 37, and by referring to registration measurements (described elsewhere in this description) and/or predetermined geometry of nail 37, selected features of nail 37 such as the distal locking hole 38 or group of holes 189 can be located by the navigation system to which sensor element 182 is connected without specifying the cannulation diameter.

To remove sensor tool 10, the user squeezes the handle portion 158 of sensor tool 10 at grips 197 towards the midplane of sensor tool 10, causing flexible tabs 192 to spread apart and clear edge 196, allowing the user to withdraw sensor tool 10 in a proximal direction.

One of ordinary skill in the art will recognize that there are a variety of constructions of sensor tool 10 that may also be used to provide the characteristic of sensor tool 10 engaging and indicating engagement at a unique position relative to nail 37. For example various connection methods may be used to attach sensor tool 10 to one or any combination of insertion tool 39, cannulated bolt 173, or nail 37 for example by clamping, bolting, or friction fit.

FIGS. 6b through 6e show another example of a snap-fit arrangement for a sensor tool adapted to engage a feature (such as a cannulated bolt 178). Such an arrangement is adaptable to a wide variety of insertion tools. FIG. 6b shows sensor tool 10 with sensor wire 180 and an alternate handle portion 676. Sensor tool 10 is shown installed in insertion tool 39 which is assembled to nail 37 with cannulated bolt 673. FIG. 6c is a section view taken from FIG. 6b showing a snap-fit sensor handle engaged with groove 671 in bolt 673. FIG. 6d is a section view taken from FIG. 6b showing boss 684 engaged in bore 670 of insertion tool 39. FIG. 6e is a detail view showing the proximal portion of a cannulated bolt 673 having a proximally extended cap portion with a groove 671 and countersink surface 672.

In this example embodiment sensor tool 10 includes handle portion 676 having conical surface 682. Groove 671 has a constant rotated section of a complete rotation about the bolt centerline forming edge 674. Countersunk surface 672 may be a complete rotated section but may also be evenly spaced segments of a rotated section about the bolt centerline. Handle portion 676 also includes flexible tabs 678 that engage edge 674 and create a seating force holding conical surface 682 against countersunk surface 672 of bolt 673 in a similar manner to flexible tab 192 and groove 195 shown in FIG. 6 and FIG. 6a, and thereby constraining sensor tool 10 relative to bolt 673 in all degrees of freedom except rotation about the centerline of bolt 673.

A wide variety of features in the insertion tool may be engaged by a portion of the sensor tool to fix The rotational position of sensor tool 10 may be fixed by providing a portion of the sensor tool adapted to engage any of a wide variety of features in the insertion tool. In the example embodiment shown, insertion handle 39 has bore 670 parallel to the bolt centerline. Cylindrical boss 684 is a push fit with bore 670. Boss 684 has slit 686 to enable a push fit to eliminate rotational play between sensor tool 10 and nail 37 under expected torque loads that may be applied to sensor tool 10 during use. Handle portion 676 also includes angled surfaces 688 which engage a countersink in a different type of insertion tool (not shown).

To remove sensor tool 10 the user squeezes grips 680 towards the bolt centerline to flex tabs 678 outwards to clear groove 671 and then pulls sensor tool 10 out proximally.

Because the engagement features in bolt 673 are revolved sections about the bolt centerline, which is coaxial with the nail centerline, sensor tool 10 can be installed at the same position regardless of the rotational position of the bolt about the centerline. Thus bolt 673 may be tightened and retightened to different rotational positions without substantially affecting the installed location of sensor tool 10 relative to nail 37 when sensor tool 10 is reinstalled. Conical surface 682 may alternately be a shoulder similar to shoulder 170 shown in FIG. 5. Conical surface 682 and countersunk surface 672 may alternately be any mating surfaces or features that fix the location of handle portion 676 in translation along the centerline of bolt 673 regardless of the rotational position of bolt 673 about its centerline.

Various other mechanical arrangements could be used in place of boss 684 or surfaces 688 depending on common features of a group of different style insertion tools intended for use with sensor tool 10, for example referring also to FIGS. 6 and 6*a*, in a set of tools with a common width 191 but not sharing a common geometry of grooves 195 or bore 670 relative to the cannulated bolt, a set of flexible tabs similar to tabs 192 having an interference fit to the outer surfaces of tool 39 may be used to constrain rotation and, in combination with the attachment arrangement of bolt 673 and tabs 678, fix the location of sensor tool 10 relative to nail 37.

Figure 6G:
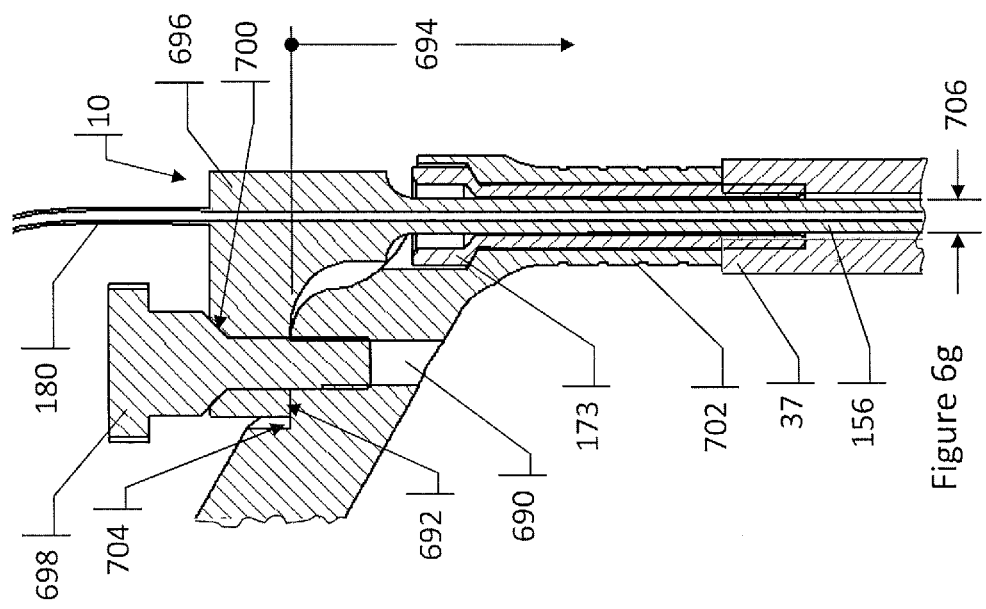
FIG. 6g is a section view taken from FIG. 6f.
Figure 6F:
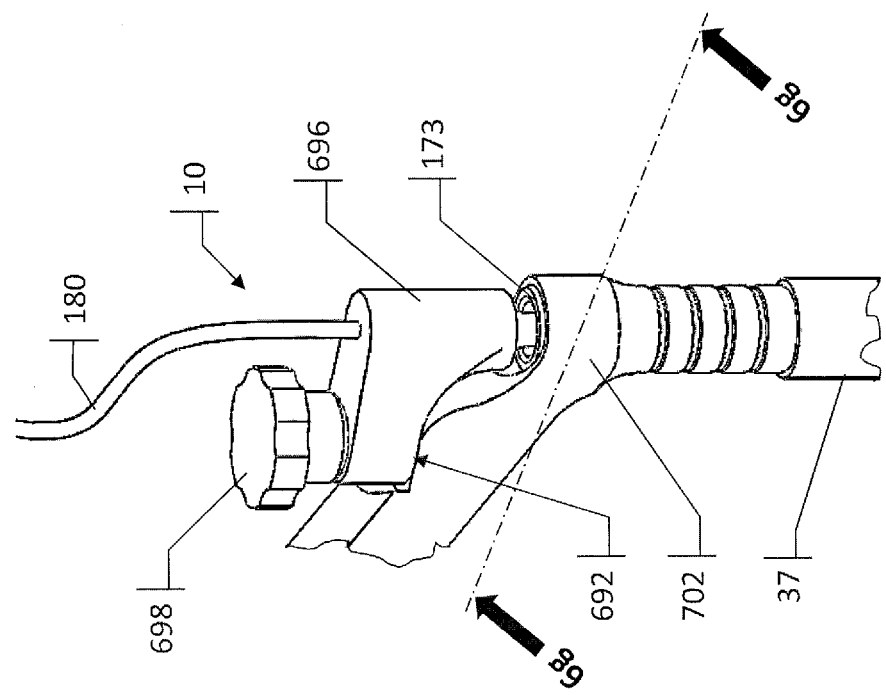
FIG. 6f shows another example of an attachment of a sensor tool to an implant using a hand-tightened fastener.

FIG. 6*f* shows an example of an attachment of a sensor tool to an implant using a hand-tightened fastener rather than a snap-fit attachment of sensor tool 10 to an insertion handle, cannulated bolt, and intramedullary nail assembly. FIG. 6*g* is a section through the sensor tool, insertion handle, and nail showing the threaded hand-tightened fastener attachment arrangement. In certain embodiments, a set of insertion tools including tool 702 may have a common threaded hole 690 relative to the centerline of cannulated bolt 173, and a surface 704 to which a surface 692 of the handle portion 696 sensor tool 10 may mate when hand-tightened fastener 698 is tightened. In this embodiment sensor tool 10 has fixed length 694 from mating surface 692 to the sensor tip (not shown, see FIG. 1*a*) and the translational position along the centerline of nail 37 of sensor tool 10 is determined by surface 704 and surface 692. Sensor handle portion 696 and fastener 698 have countersink 700. Fastener 698 is threaded to match hole 690.

In this embodiment sensor tool 10 has shaft diameter 706 at least over the proximal region where the sensor shaft lies inside bolt 173 when sensor tool 10 is installed. Diameter 706 of shaft portion 156 of sensor tool 10 is a sliding fit to cannulation diameter 174 of bolt 173 (visible in FIG. 5). When fastener 698 is tightened sensor tool 10 may rotate about the centerline of hole 690 only to the extent of the difference of diameters 706 and 174, and shaft portion 156 and will bear against the inner surface of cannulated bolt 173 as fastener 698 is tightened. Thus when fastener 698 is tight sensor tool 10 is fixed in all six degrees of freedom relative to nail 37 in a precise position. Fastener 698 may be made of sterilizable plastic material similar to that of sensor tool 10 and supplied with sensor tool 10, for example, or may be made of metal or another reusable and sterilizable material. One ordinarily skilled in the art will recognize that to be compatible with various insertion handles, handle portion 698 may have an array of holes at different locations and may have several different mating surfaces similar to surface 692 to match the selected insertion handles.

Another aspect of the invention provides a tool comprising a field generator that is configured to remain fixed relative to an axis of the tool and a point along the axis during use of the tool, where the portion of the tool may move relative to the axis and/or the point. For example the tool may comprise a drill and the moving portion may be a drill bit that rotates about the axis with the tip of the drill bit at the point on the axis. For another example the tool may comprise a saw and the moving portion may be a saw blade that rotates about the axis in a plane passing through the point. For another example the tool may be an oscillating saw and the moving portion may be a saw blade that rotates back and forth through a small range of rotation, in a plane passing through the point. This arrangement is an advantage because, particularly when the moving portion of the tool is made of ferromagnetic and/or electrically conductive materials, the tool may affect the performance of the field generator and cause measurement errors. Therefore limiting the position, pattern of motion, and range of motion of the tool and any movable portion of the tool to known and predictable values may allow various measurement correction and error compensation to be used to improve the performance of the field generator.

In some embodiments the axis may be offset from field generator, which may improve access to portions of the tool located on the axis and improve the user's view of the tool and the work area. For example a drill bit located along the axis and passing outside, rather than through, the field generator may be easier to change and easier to aim as the user can see along the drill bit length.

The field generator may be mounted or mountable directly to the tool. In other embodiments the field generator is mounted or mountable and detachable to an attachment for the tool. In other embodiments the field generator and/or attachment unit may be attachable to a variety of tools. In other embodiments the field generator and/or attachment unit may be attachable at various rotational positions about the axis without changing the relationship of the field generator to the axis or the point on the axis. For example the tool may be a drill and the field generator may be mounted to a unit comprising a drill chuck that may fit several different types of drill, and may attach to a drill at various angles about the drill bit axis relative to a drill handle, allowing the user to select a position of the field generator that does not block the view of the work area or interfere with obstacles in the work area.

In other embodiments the field generator is mountable and detachable to an attachment for the tool, wherein the attachment is adapted to hold the field generator at a selected location relative to an axis and a point on the axis. Some embodiments may additionally comprise a housing that encloses and isolates the field generator. For example in embodiments adapted for surgery the attachment may comprise an autoclavable housing and the field generator may be non-autoclavable, and in use in a sterile field a non-sterile user drops the field generator into the sterile attachment held by a sterile user, who then closes the housing thereby fixing the field generator in position and isolating it from the sterile field. This arrangement has the advantage of reducing the cost and increasing the service life of the field generator.

Each feature of a tool comprising a field generator described above may be advantageous individually or in combination with some or all of the other features described. Other embodiments within the scope of the invention may include a subset of the advantageous features described above and in example embodiments.

Figure 7:
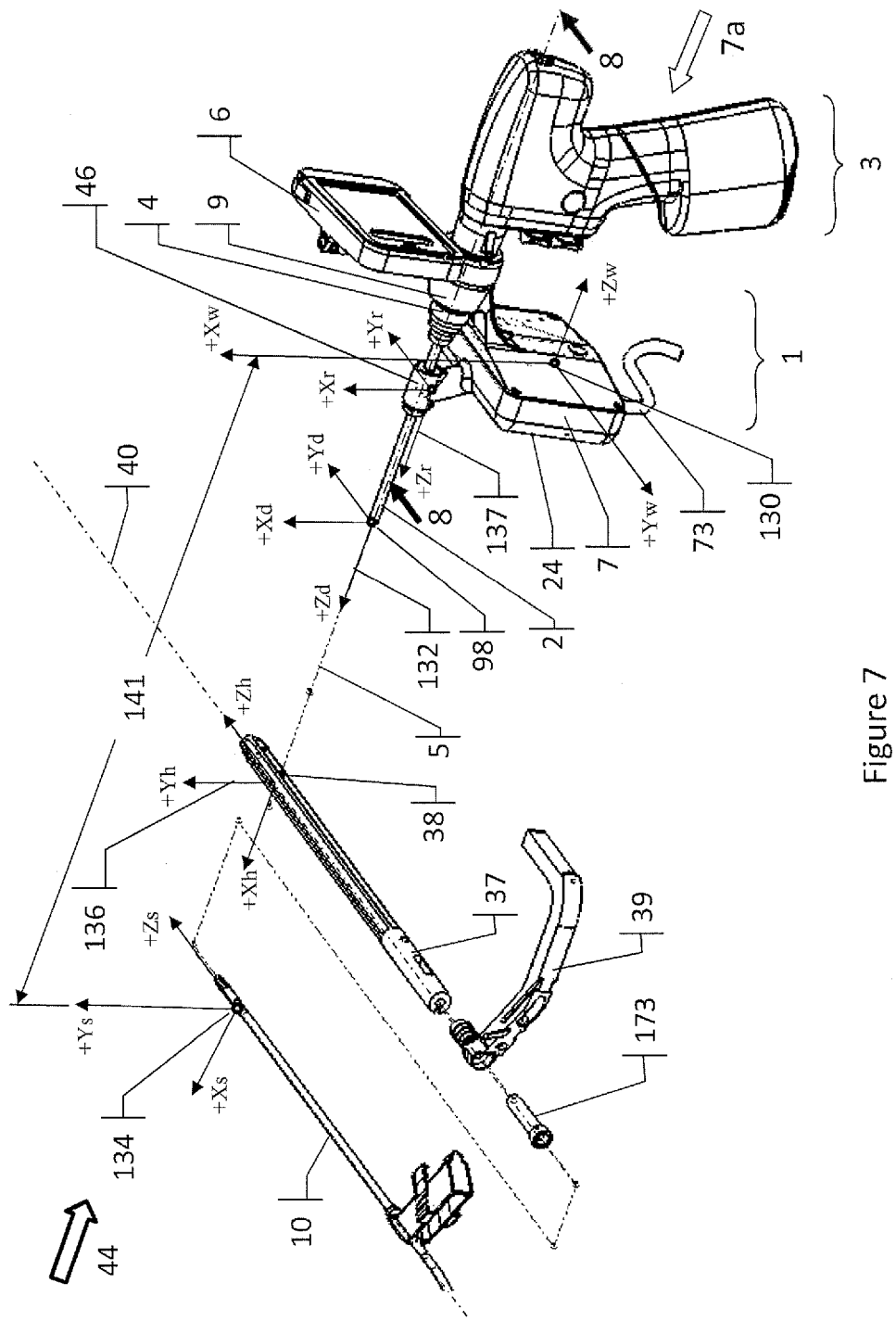
FIG. 7 shows an example navigation unit integrated with a drill, according to one embodiment of the invention, along with an IM nail having a locking hole, and a sensor tool, and also showing an exemplary set of coordinate systems.

FIG. 7 shows an example navigation unit 1 with drill bit 2 installed. The navigation unit is mounted to drill 3. Sensor tool 10, and IM nail 37 having locking hole 38 are also shown. Unit 1 includes electromagnetic field generator 7.

We have observed that when a commonly used type of drill bit 2 (Part #03.010.104 Synthes™, Monument, Colo. 80132) is moved in front of a typical field generator, measurement distortions are:

Much greater than one millimeter when drill bit 2 is moved about in front of the field generator, Greater that one millimeter when drill bit 2 is moved in and out of the area in front of the field generator along a fixed axis, and Less than one millimeter when drill bit 2 is spinning about a fixed axis relative to a field generator.

Advantageously, in the embodiment of the invention depicted in FIG. 7 drill bit 2 rotates about drill axis 5 and unit 1 holds drill bit 2 in a fixed location relative to field generator 7 via housing 9. Point 98 is coincident with axis 5 and with the tip of drill bit 2, and along with axis 5 is fixed relative to housing 9 and field generator 7 while unit 1 is in use. This arrangement limits electromagnetic distortion effects on the navigation system due to the presence of drill bit 2 in the measurement range of field generator 7 to a predictable and manageable level, thereby allowing drill bit 2 to be made of typical ferromagnetic materials. In various embodiments of the invention drill bit 2 may replaced with various items such as reamers, milling cutters, burrs, guide wires, and the like.

Advantageously, drill 3 and unit 1 including field generator 7 may be assembled into a single unit that can be operated with one hand. In such an integrated unit, it may be a further advantage to minimize the size and weight of field generator 7, and to position field generator 7 relative to drill 3 in such a way as to minimize interference with handling of drill 3, the patient and operating table, and the user's view of the work area. In particular it may be an advantage if the user has a clear view of the drill bit 2. Accordingly in certain embodiments unit 1 may be attached to drill 3 at a variety of rotational positions about drill axis 5 and may be removed and reattached at a different rotational position during use without requiring recalibration.

A further advantage of unit 1 having field generator 7 and chuck 4 integrated may be that the distal tip of drill bit 2 is at a fixed position relative field generator 7, and with sensor tool 10 in a fixed position relative to the region being drilled, the distance traveled by drill bit 2 along drill axis 5 through the region can be tracked directly by the navigation system as described below in FIG. 9. By identifying an entry or starting point, the drilling progress along the drill axis can be reported to the user. By identifying an entry point and an exit point through a bone, for example, the length of the drilled hole through the bone can be reported to the user and used to help select the correct screw length to install.

In general, electromagnetic measurement distortions may be limited to manageable levels by limiting and predicting the introduction, removal, and movement of ferromagnetic and conductive material mass within the range of field generator 7 and to a lesser extent near field generator 7. Accordingly in another example embodiment, unit 1 is adapted to attach to a tool such as an oscillating saw, and is further adapted to hold a cutting tool, such that the cutting tool moves in a limited range and in a predetermined pattern, the pattern being in a fixed location relative to field generator 7. For example an example embodiment is like the drill shown in FIG. 7 except that drill bit 2 is replaced with an oscillating saw blade, drill 3 is replaced with an oscillating saw, and chuck 4 is replaced with an oscillating saw blade chuck having an axis about which the blade oscillates within a predetermined limit of angular travel, such that the blade oscillates about the axis in a plane normal to the axis, both the plane and the axis being in fixed positions relative field generator 7.

Looking now in detail at the exemplary embodiment depicted in FIG. 7, unit 1 includes chuck 4 as an integral component of housing 9, reference sensor 8 (visible in FIG. 8), and drill bushing 46, all of which are mounted in fixed locations relative to field generator 7. Axis 5 is defined by chuck 4 and bushing 46, and is therefore also in a fixed location relative to field generator 7 during use. User interface unit 6 is also mounted to unit 1 and may be adjusted to different positions relative to unit 1 as described in more detail later in the description. One of ordinary skill in the art will recognize embodiments that do not include user interface unit 6 on unit 1, for example a display screen may alternately be located outside the surgical field.

Figure 8:
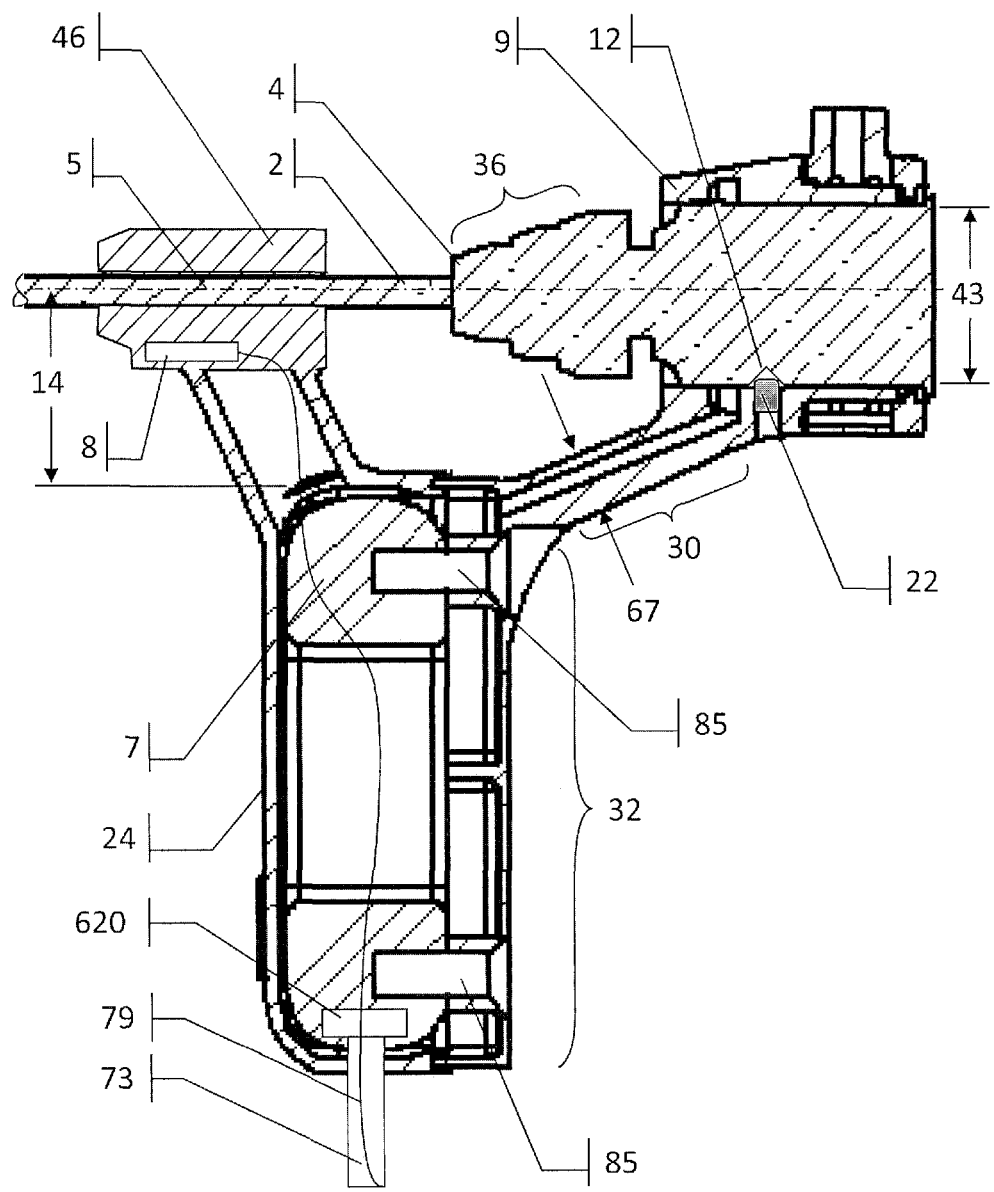
FIG. 8 is a section taken from FIG. 7, through the drill axis, showing the exemplary navigation unit attached to the drill.
Figure 8A:
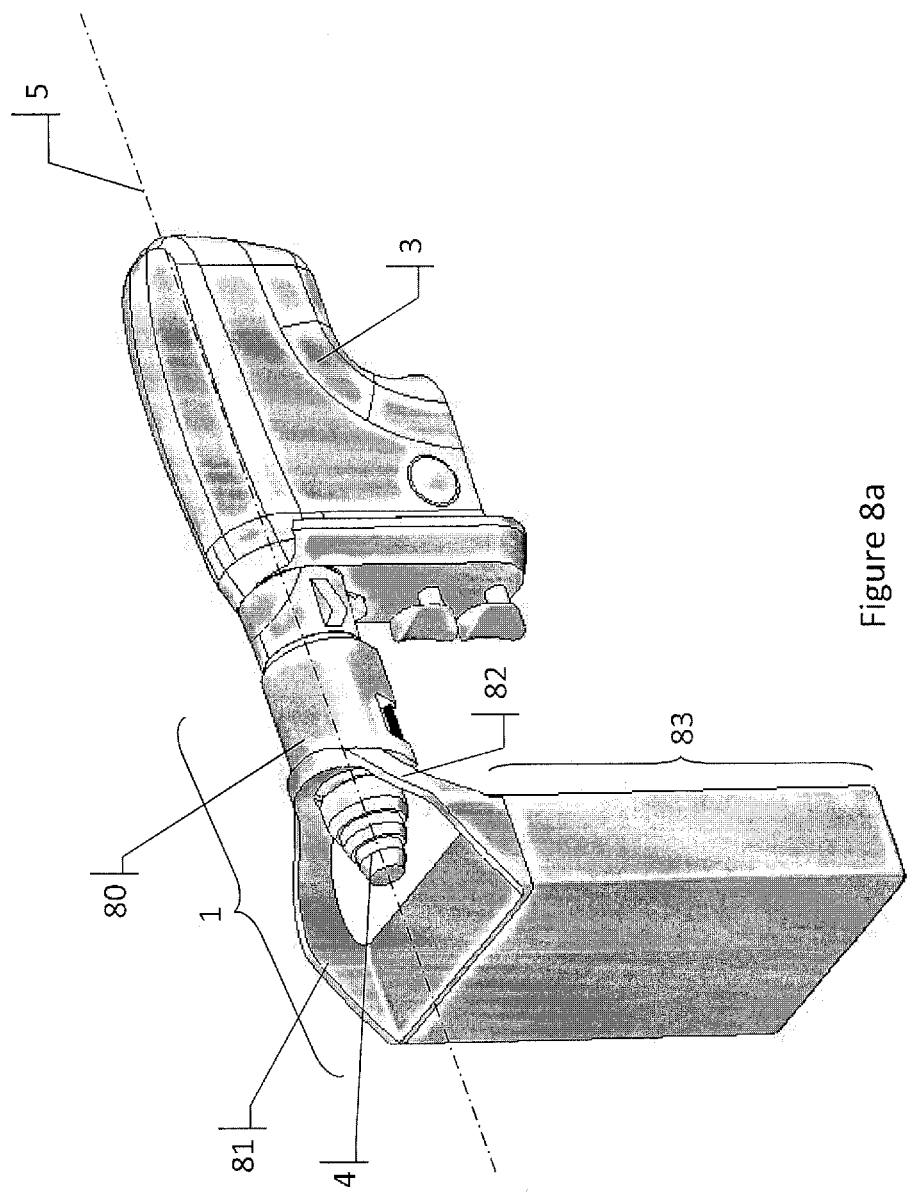
FIG. 8a shows an alternate embodiment of the invention, in which a navigation unit is integrated with a drill via structure above rather than below the drill chuck.
Figure 8B:
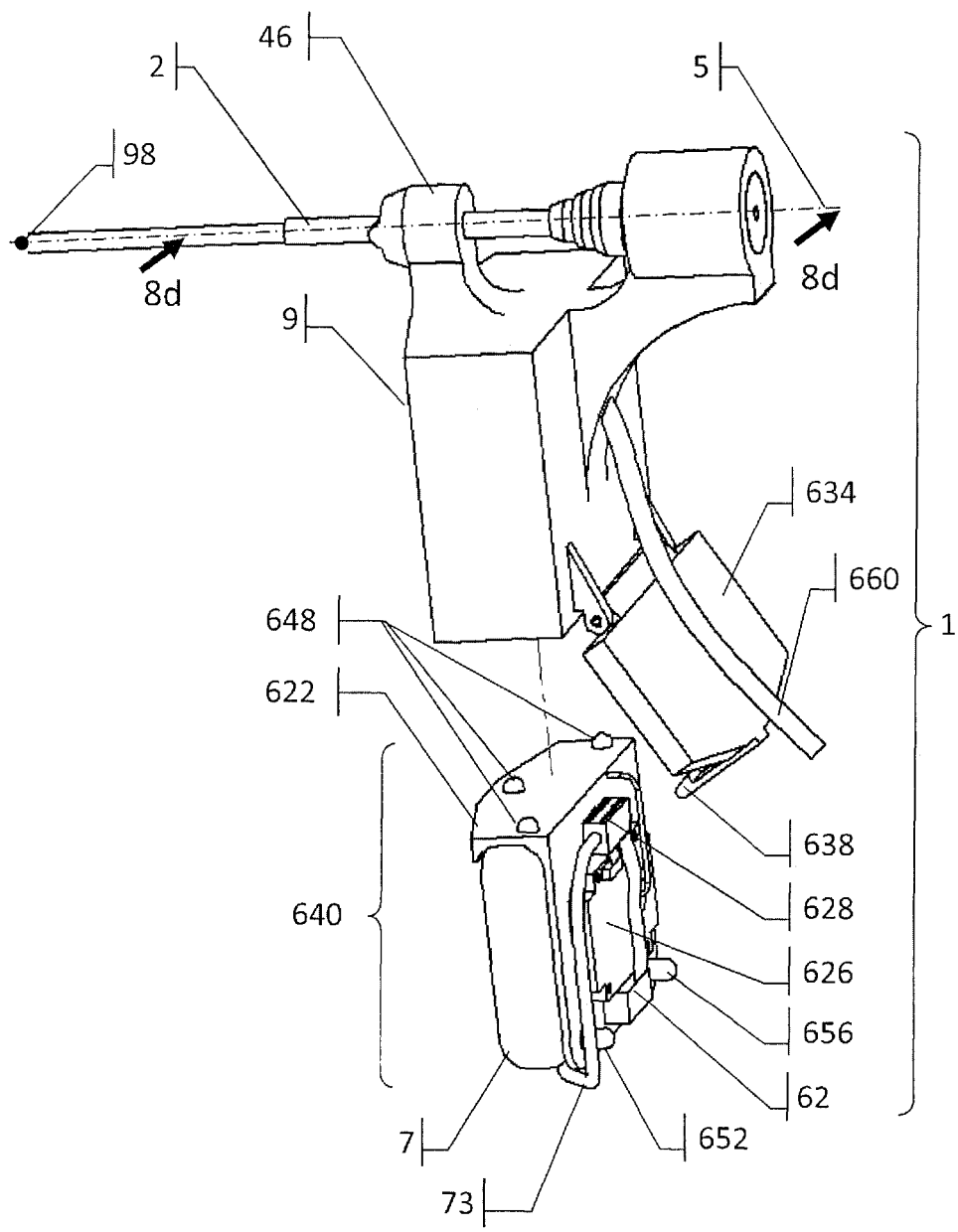
FIG. 8b shows another embodiment of the invention in which the field generator may be removed and replaced repeatably to the same location within the navigation unit.
Figure 8C:
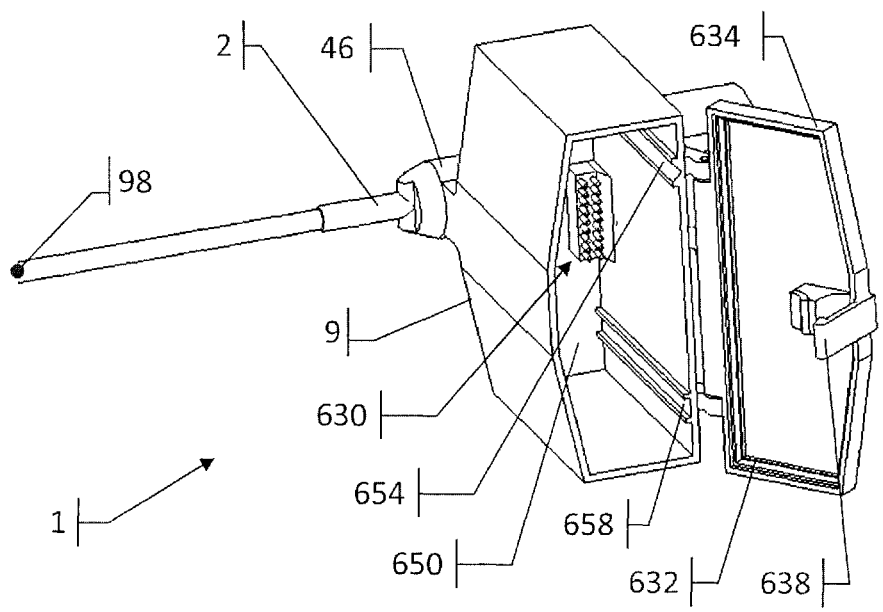
FIG. 8c shows another perspective view of the embodiment of FIG. 8b.

Referring also to FIG. 8, in which field generator 7 emits an electromagnetic field which causes reference sensor 8 and sensor tool 10 to emit signals indicative of their positions relative to field generator 7. Field generator 7, sensor 8, and sensor 10 are part of, and are connected to, a navigation system (not shown). Reference sensor 8 returns a constant predetermined location relative to field generator 7 to the navigation system and if this location varies beyond predetermined limits an error warning may be issued to the user. Reference sensor 8 is shown in the embodiment embedded in the structure connecting field generator 7 and bushing 46, however one skilled in the art will recognize that reference sensor 8 may alternately be integrated into field generator 7 (as shown in FIG. 8a, FIG. 8b, and FIG. 8c) for example mounted rigidly or moulded in to the front face of field generator 7, or otherwise mounted in a fixed position relative to field generator 7 and within the measurement range of field generator 7. For increased reliability and redundancy a group of several reference sensors 8 may be used. When installed (see FIGS. 1 through 6b), sensor tool 10 is located in IM nail 37 at a fixed, predetermined location relative to locking hole 38, but does not block or protrude into hole 38. Nail 37 is shown as a straight nail having a straight longitudinal centerline 40, however nail 37 may also be curved over selected regions of its length. In the embodiments shown, unless otherwise noted, nail 37 is straight from a point proximal to the most proximal locking hole 38 to the distal end of nail 37, and centerline 40 refers to the longitudinal centerline of this straight portion.

In typical use, nail 37 is implanted inside a bone (not shown). The navigation system uses the position data from sensor 10 and the predetermined location to generate guidance information displayed to the user on display 6 to help the user align axis 5 with locking hole 38. A suitable navigation system, including field generator 7 and suitable sensors 8 and 10 is an Aurora™ system made by Northern Digital Inc., Waterloo, Ontario, Canada. A suitable model of field generator for this application is the Compact Field Generator™, being of a small enough size and low enough weight so as to not hamper operation of drill 3, yet having enough measurement range to encompass sensor tool 10 during aiming of drill 3 with drill bit 2 attached. Field generator 7 has an integrated erasable and rewritable memory 620, visible in FIG. 8, which can be used to store information such as calibration factors and serial numbers. Memory 620 may be, for example, a flash-type memory device.

Drill 3 may be a typical electric or air powered surgical drill that optionally contains ferromagnetic parts and may generate and emit magnetic fields. In the exemplary embodiment drill 3 is a Synthes Small Battery Drive (Synthes USA, West Chester, Pa.) with a brush-type DC electric motor powered by a battery mounted in the drill handle area. Drill bit 2 may be made of ferromagnetic material, such as hardened stainless steel. Chuck 4 is adapted to couple to drill 3 at several rotational positions about axis 5. The interface between chuck 4 and drill 3 may be adapted as desired to fit selected types of drill 3, for example drills from various different manufacturers, air-powered drills, or other types of tool. Chuck 4 is mounted so that its axis of rotation is fixed relative to field generator 7. For example, chuck 4 may be mounted to rotate suing suitable bushings, bearings or the like.

Although unit 1 is depicted as being separate from drill 3, in other embodiments, features of unit 1 such as field generator 7 and/or a display and/or chuck 4 may be integrated directly with a tool such as drill 3.

Chuck 4 may be replaced or adapted for tools other than drills and drill bits, for example K-wire drivers, screwdrivers, pin inserters, or for other procedures requiring alignment of a tool having an axis that can be defined relative to field generator 7. Chuck 4 may also contain or be made of hardened stainless steel or other ferromagnetic materials.

Referring also to FIG. 8, field generator 7 is both connected to a navigation system console (not shown, typically located outside the sterile surgical field) via cable 73. Reference sensor wire 79 also joins cable 73 and is also connected to the navigation system. The navigation console communicates wirelessly to display screen 6. Cover 24 is also shown. One of ordinary skill in the art will recognize that various combinations of wired and wireless communication may be used in alternate embodiments of the invention, for example field generator 7 may be powered from an electrical power source also powering drill 3, such as a battery, and field generator 7 control communication and reference sensor 8 signals may be transmitted wirelessly to and from the navigation system console, thereby eliminating cable 73. In the embodiment shown in FIG. 8, field generator 7 is adapted to be sterilized with unit 1 and is rigidly connected to housing 9 by countersunk screws 85.

Also shown in FIG. 7 are the coordinate frames are defined for calibration and navigation. Various arrangements of coordinate frames may be used to relate a target axis such as the axis of hole 38 to sensor 10 and drill axis 5. All coordinate frames described below for the embodiment shown are not necessarily required in other embodiments of the invention. The configuration shown in is a lateral approach, and arrow 44 shows the direction of a medial approach. Field generator coordinate system 130 (subscripted 'w' for 'world'), drill coordinate system 132 (subscripted 'd'), sensor coordinate system 134 (subscripted 's'), and locking hole coordinate system 136 (subscripted 'h') are all three dimensional right hand Cartesian coordinate systems with orthogonal X, Y, and Z axes. Field generator coordinate system 130 is predetermined at field generator manufacture, is fixed in all six degrees of freedom relative to the structure of field generator 7, and is the coordinate system in which the navigation system reports the position of sensors such as sensor 8 and sensor 10 within the measurement range of field generator 7 (hence the subscript 'w' for 'world' since this is the how the navigation system sees the world). Describing the relative positions in the components in terms of homogeneous transforms, a constant transform Twd is defined from field generator coordinate system 130 of the field generator 7 to drill coordinate system 132 aligned with drill axis 5. Drill coordinate system 132 has its origin at a selected point on drill axis 5, a suitable point being the tip of drill bit 2 which may be preprogrammed into the system, determined by the user entering the drill bit length, or by a typical pivot calibration method as described in the spatial tracking literature (also available as software routines from navigation system manufacturers such as Northern Digital Inc., Waterloo Ontario Canada). The Zd axis of drill coordinate system 132 is defined as collinear with drill axis 5 and having the positive Zd direction extending distally from the drill user. The Xd axis of drill coordinate system 132 is defined as normal to the Zd axis of drill coordinate system 132 and lying in the plane passing through drill axis 5 and the origin of field generator coordinate system 130, with the positive Xd direction of drill coordinate system 132 extending away from field generator 7. The Yd axis of drill coordinate system 132 is then defined by the cross product of the Xd and Zd axes to form a right hand three dimensional Cartesian coordinate system. Sensor coordinate system 134 is predetermined at sensor manufacture and is fixed in all six degrees of freedom relative to the structure of sensor 10, with the Zs axis of sensor coordinate system 134 being approximately collinear with the longitudinal centerline 40 of nail 37 when sensor 10 is installed in nail 37. During operation the navigation system reports the transform Tws from field generator coordinate system 130 to sensor coordinate system 134 at a rate of twenty to forty times per second. Locking hole coordinate system 136 may be defined by the predetermined dimensions of sensor tool 10, nail 37, and insertion tool 39. Alternately locking hole coordinate system 136 may be defined by aligning drill axis 5 with the centerline of hole 38 (for example by using a registration tool as shown below in FIG. 22) and making a direct measurement as follows:

The Zh axis of locking hole coordinate system 136 lies on the line normal to drill axis 5 and passing through the origin of sensor coordinate system 134, with the positive Zh direction towards the distal end of nail 37

The origin of locking hole coordinate system 136 is at the intersection of the Zh axis and drill axis 5.

The Xh axis of locking hole coordinate system 136 is collinear with drill axis 5 with the positive Xh direction pointing away from the drill.

The Yh axis of locking hole coordinate system 136 is the cross product of the Zh axis and drill axis 5.

Also shown is reference sensor coordinate system 137 which is at a fixed location relative to field generator coordinate system 130. Reference sensor coordinate system 137 may be positioned at any fixed location and orientation within the measurement volume of the navigation system. Distance 141 is defined as the distance from the origin of field generator coordinate system 130 to the YsZs plane of sensor coordinate system 137 along the Zw axis of field generator coordinate system 130. The approach direction of navigation unit 1 with respect to the assembly of handle 39 (seen in FIG. 3), nail 37, and sensor 10 can be determined as lateral or medial as follows:

If the dot product of Zw and Xs is negative, it is a lateral approach, and

If the dot product of Zw and Xs is positive, it is a medial approach.

Figure 7A:
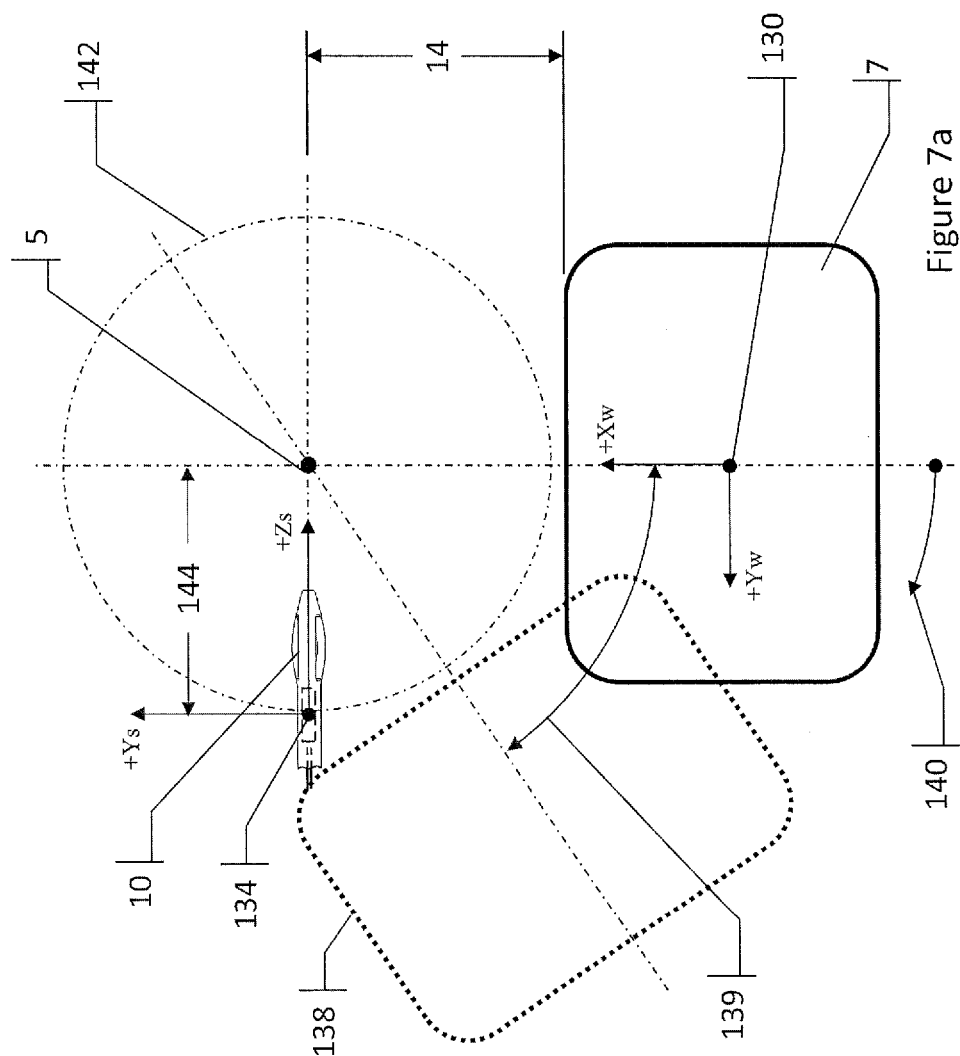
FIG. 7a shows the exemplary coordinate systems of the field generator and sensor looking along the drill axis from the drill user's point of view, and the parameters of the subset of sensor positions that are critical in the exemplary embodiment and application.

With reference to FIG. 7a, in accordance with an embodiment of the invention, a view is shown looking along drill axis 5 from the drill user's point of view and a set of parameters defining critical sensor positions for the exemplary embodiment are described. It is advantageous to define a subset of sensor positions and orientations that are critical to the targeting objective for a particular application and embodiment in order to simplify various calibration and error compensation methods described elsewhere in this specification. In other embodiments of the invention, different sets of parameters may be critical and may be defined differently. For clarity nail 37, drill 3, navigation unit 1 and the proximal portion of sensor 10 (seen in FIG. 7) are not shown in FIG. 7a, and only the outer perimeter of field generator 7 is shown. The outer perimeter of field generator 7 is located distance 14 from drill axis 5 to allow access to the distal portion chuck 4 for ease of installation and removal of a drill bit or other drill-mounted tool (see FIG. 8), and to give the user a clear view of the drill bit. For example distance 14 may be twenty-five millimeters. Rotated field generator position 138 is a dashed outline of field generator 7 shown rotated about drill axis 5 to heading 139. Heading 139 is defined as zero when the Yw axis of field generator coordinate system 130 is parallel with, and in the opposite direction to, the projection of the Zs axis of sensor coordinate system 134 into the XwYw plane of field generator coordinate system 130; the solid outline of field generator 7 shown is the position at which heading 139 equals zero. Heading 139 is defined as positive as the field generator is rotated about drill axis 5 in the direction of arrow 140. Heading 139 is expressed as an angle greater than or equal to zero degrees and less than three hundred and sixty degrees.

When drill axis 5 is held coaxial with the centerline of hole 38 (for example by using a registration tool as shown below in FIG. 22) and field generator 7 is rotated about drill axis 5 through various headings 139 from zero to three hundred and sixty degrees, the origin of sensor coordinate system 134 describes a nominal circle 142 having radius 144, and in the exemplary embodiment since drill axis 5 is nominally parallel to the Zw axis of field generator coordinate system 130, nominal circle 142 lies in a plane normal to the Zw axis of field generator coordinate system 130. Radius 144 is constant for a particular combination of nail 37 and sensor tool 10.

The exemplary embodiment shown is designed to be used with a predetermined range of different nails, having known lengths and locking hole positions along the length, and sensor tools are provided in a variety of lengths and one or two particular lengths are recommended for use with each type of nail, and the origin of sensor coordinate system 134 is always proximal to hole 38 due to the relationship (shown in FIG. 1a and FIG. 4) of length 176 to minimum distance 178, therefore radius 144 has a predetermined range. Similarly, referring also to FIG. 7, there is a known range of distances 141, which is a function of the length of drill bit 2 and the range of bone diameters expected to be encountered. Thus when drill axis 5 is aligned with locking hole 38 and in a position to begin drilling, with field generator 7 at any heading 139, it is critical to maximize measurement accuracy and there is a subset of possible positions of sensor 10 relative to field generator 7 defined by three parameters: radius 144, heading 139, and distance 141.

FIG. 8 is a section taken from FIG. 7 through drill axis 5 with drill 3 and user interface unit 6 deleted for clarity. In the exemplary embodiment it is advantageous to permanently fix chuck assembly 4 to housing 9 is such a way as to deter users from attempting to reposition or remove and reinstall chuck assembly 4 and thereby possibly alter the position or orientation of chuck assembly 4 relative to field generator 7 which would require recalibration of drill coordinate system 132 (shown in FIG. 7) and may also affect various error compensation methods described in subsequent parts of this specification. Housing 9 has inner bore 43. Chuck assembly 4 is permanently fixed within bore 43 at a selected rotational position relative to housing 9, with sufficient strength to withstand weight and inertial loads generated as the user moves drill 3 or picks up and holds unit 1 and drill 3 by grasping a part of unit 1 such as field generator 7. In the exemplary embodiment chuck assembly 4 is fixed to housing 9 by driving spring pin 22 against divot 12 in chuck assembly 4. One of ordinary skill in the art will recognize that a variety of attachment methods may be used that will sufficiently hold unit 1 in place on chuck assembly 4, for example chuck assembly 4 may be bonded into inner bore 43 using a suitable adhesive, interference fit, or the like.

An advantageous feature of unit 1 is that field generator 7 is located at an offset from drill axis 5, which allows for sufficient space around chuck 4 for the user to operate chuck 4 and to install and remove drill bits, and also provides the user with a better view of drill bit 2 and the target area. Distance 14 is selected to allow a typical user's index finger to grasp collar portion 36 and pull it back in a proximal direction to release the drill bit. Arm portion 30 of unit 1 connects the field generator mounting portion 32 of unit 1 to housing 9 of unit 1 and has thickness 67 and width (not shown) selected to allow arm portion to fit between the user's index and middle finger so the user can hold the drill while changing the drill bit. For arm portion 30 a suitable thickness 67 is ten millimeters and width (not shown) is twenty millimeters. Housing 9 also includes cover 24 and bushing 46 which are both rigidly attached to chuck 4 via housing 9 and field generator mounting portion 32. The material of housing 9, including arm portion 30, field generator mounting portion 32, bushing 46, and cover 24, is preferably non-ferrous and of low conductivity so as to minimize effects on the electromagnetic navigation system, lightweight so as not to hamper the user in operating drill 3, but of sufficient rigidity to maintain the position of field generator 7 relative to drill axis 5 within one millimeter and one degree under normal inertial and handling loads during use. For the exemplary embodiment the material preferably withstands autoclave or other high temperature sterilization processes without deforming. Some examples of suitable materials are titanium, PEEK, or Ultem™. A wide variety of other suitable materials may be used. Memory device 620 which is a part of field generator 7 and is connected to the navigation system via cable 73 is also shown.

FIG. 8a shows an alternate embodiment of the invention in which navigation unit 1 has an alternate structure that maintains open access to drill chuck 4 from below drill axis 5 thereby allowing use of drill chucks with attachments below the drill axis, such as a K-wire driver. In this alternate embodiment two rigid arm portions 81 and 82 connect housing portion 80 to field generator mounting portion 83.

Figure 8D:
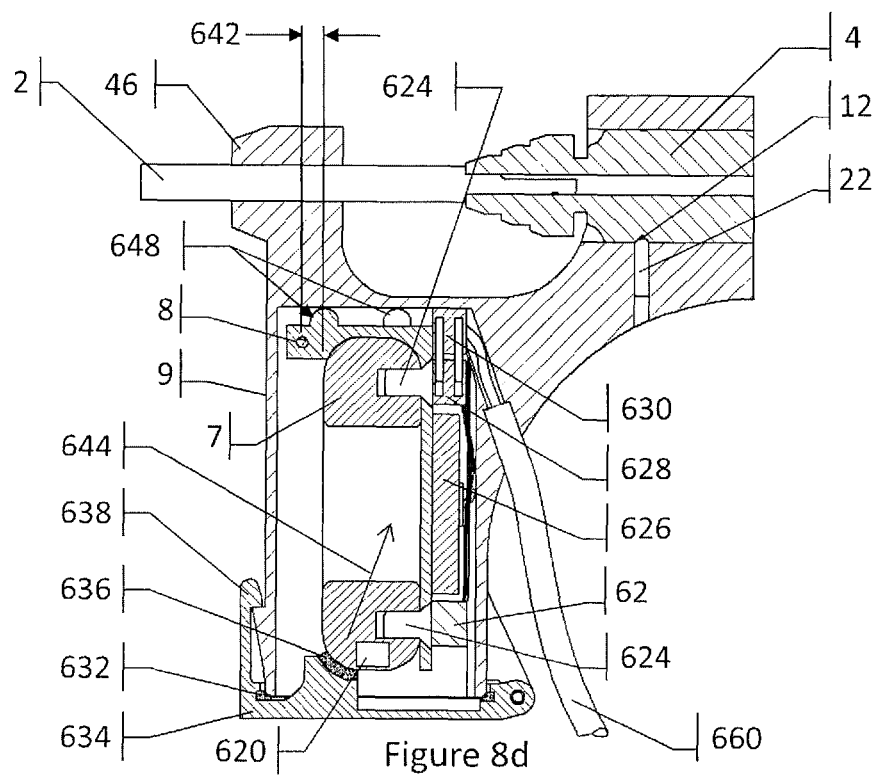
FIG. 8d shows a partial cross-sectional view of the embodiment of FIG. 8b.

FIG. 8b, FIG. 8c, and FIG. 8d show another embodiment of the invention in which the field generator may be removed and replaced to the same location within the navigation unit relative to drill axis 5 and tip point 98, and is housed and isolated within navigation unit 1. This arrangement allows field generator and reference sensor unit 640 to be separated from navigation unit 1 before cleaning and sterilizing unit 1. Unit 640 may then be cleaned (but not necessarily sterilized) using different methods which may be more compatible with the field generator, sensor and associated electronic components in unit 640. Unit 640 may then be reinstalled in a sterile environment with no contact between unit 640 and any surface of unit 1 that is exposed after installation of unit 640 is complete. Housing and isolation of unit 640 is designed to prevent direct contact by a user and direct communication of fluids with unit 640 when unit 640 is installed in housing 9. The embodiment shown may also be adapted to non-surgical applications in which it is an advantage to protect unit 640 from the environment, for example from fluids or dust, while unit 1 is in use.

FIG. 8b is an exploded view showing unit 640 outside housing 9. In this example embodiment field generator 7 is shown adapted for mounting in housing 9 via chassis 622 and is rigidly fixed to chassis 622 by countersunk screws 624. Sensor interface circuit board 626, accelerometer 62, docking connector jack 628, and reference sensor 8 are all mounted to chassis 622 to form one rigid field generator unit 640. Reference sensor 8 (visible in FIG. 8d) is rigidly mounted, for example by bonding, to chassis 622 at distance 642 in front of the front face of field generator 7 as shown, within the measurement range of field generator 7.

FIG. 8b is a view looking inside housing 9 with unit 640 removed. In this example embodiment housing 9 is adapted to receive field generator 7, and includes docking connector plug 630, seal 632, door 634, elastic bumper 636, and latch 638. Cable 73 is mounted to housing 9, wired to plug 630, and connects to the navigation system console 600 (visible in FIG. 1).

In the example embodiment shown, a minimum constraint design is used to position unit 640 at a precise position in housing 9. When installed, chassis 622 contacts housing 9 at six points as follows: Three convex contact surfaces 648 each make a point contact with planar surface 650, convex contact surface 652 makes two point contact with v-groove 654, and convex contact surface 656 makes point contact with planar surface 658. When seating force 644 is applied in a direction that creates a reaction force from housing 9 towards unit 640 at all six contact points, unit 240 is held in all six degrees of freedom relative to housing 9. Seating force 644 is directed approximately through the middle of the group of contact points in order to produce approximately equal reaction forces at each point. Seating force 644 is designed to be sufficient to maintain contact at all six points as unit 1 is used, for example force 644 must be sufficient to resist inertial loads on unit 640 created as unit 1 is moved about by the user. Seating force 644 is created by elastic bumper 636 which is compressed a selected amount against contact surface 646 of unit 240 when door 634 is closed and latch 638 is engaged.

Reference sensor 8 is wired to circuit board 626. Circuit board 626 converts signals from reference sensor 8 to digital signals which are then sent to the navigation system console via jack 628, plug 630 and cable 660. Sensor readings from reference sensor 8 may be more reliable when transmitted as digital signals, rather than the original sensor signals, along the length of cable 660 in conductors running alongside the power supply conductors for field generator 7 included in cable 660. However in some embodiments wiring from reference sensor 8 may connect to docking connector 628 and continue on to console 600 via jack 630 and shielded conductors in cable 660, thereby eliminating the need for board 626 in unit 640. Accelerometer 62 and field generator 7 are wired to docking connector jack 628 and in turn communicate with the navigation system via plug 630 and cable 660. Field generator cable 73 (visible in FIG. 8b) is wired to jack 628. Memory device 620 which is a part of field generator 7 is also shown and communicates with the navigation system via cable 73.

An example of a suitable field generator 7 is an Aurora Compact Field Generator™ and an example of a suitable sensor interface circuit board 626 is part number 7000420, both available from Northern Digital Inc, Waterloo, Ontario, Canada. An example of a suitable distance 642 is five millimeters. Chassis 622, screws 624, door 634, and latch 638 may all be made of a lightweight, rigid, non-ferromagnetic and low electrical conductivity material, for example PEEK or titanium. Seal 632 and elastic bumper 636 may be made of a high temperature tolerant elastomer, for example silicone. For another example elastic bumper 636 may be a spring. The remaining components comprising unit 640 may be selected and designed to minimize mass of included ferromagnetic and conductive materials.

In some embodiments a plurality of reference sensors may be used at various locations in front of field generator 7 and at various distances approximately equal to or greater than distance 642. In some embodiments accelerometer 62 may be integrated with circuit board 626. One ordinarily skilled in the art will recognize that many alternate mechanical arrangements may be used to enclose and seal unit 640 within housing 9 after installation and to apply seating force 644, and that many alternate mechanical arrangements may be used to hold unit 640 at a precise position within housing 9. For example a threaded clamp, over center clamp, or a cam mechanism may be used. For another example unit 644 may alternately be isolated in a sealable sterile isolation bag before installation into housing 9, in which case the contact pins of jack 628 pierce the isolation bag upon installation. In some embodiments, for example where operation in a sterile field is not required or when an isolation bag is used as described above, seal 632 and/or door 634 may not be required and a wide variety of alternate securing arrangement may be used to hold unit 640 in position. One ordinarily skilled in the art will recognize that unit 640 is shown as an example arrangement incorporating an existing and available field generator and that all or some of the components of unit 640 may be integrated into the structure of a custom field generator to form a single unit.

Figure 9:
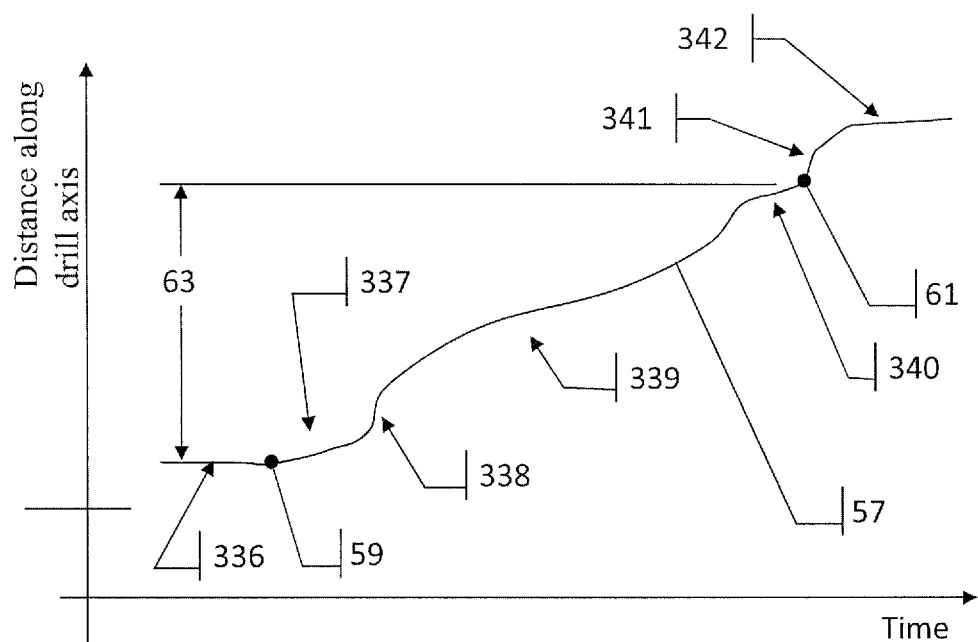
FIG. 9 shows an example of a trace of drill bit distance along a drilling path versus time for drilling through a bone.

FIG. 9 is sample trace 57 of drill travel along a drilling path versus time. Referring also to FIG. 7, a feature of unit 1 having drill axis 5 and a tool tip point 98 on axis 5 in a fixed position relative to field generator 7 is that the motion of tip point 98 relative to sensor 10 (and thereby any structure at a known position relative to sensor 10), may be recorded and analysed. In various embodiments the data may be processed and used advantageously to advise the user of tool travel, tool performance, to optimize parameters related to tool travel such as cutting speed and feed rate, to warn the user of possibly unsafe or damaging conditions such as rapid plunge-through of the tool, and to initiate or advise of corrective actions such as stopping a tool motor.

In some embodiments this data may be used in conjunction with other recorded parameters such as a state of the tool (for example if the tool motor is on or off), tool power draw, tool torque, vibration, tool motor speed, mode of tool operation (for example, forward, reverse, or oscillating drill rotation), and the like, some of which may be detectable using reference sensor 8 and sensor 10 and some of which may additionally require a data monitoring link from the tool to the navigation system. Certain states of the tool may be determined using the navigation system by processing data from sensor 10. In embodiments including a reference sensor such as reference sensor 8, certain states of the tool may be determined using the navigation system by processing data from the reference sensor as described in more detail in FIG. 28, either in conjunction with or instead of data from sensor 10.

In addition to being able to monitor the length of the drilled hole (as described below), knowledge of the distance versus time relationship may be used in conjunction with other sensed information to optimize the drilling process. For example, if it is desired to progress at a desired rate (for example to avoid bone necrosis due to excessive heating), the current cutting rate may be estimated by applying any of the many known filter designs for estimating the derivative of a position signal (for example, a simple finite difference differentiator, a differentiator in combination with a low-pass filter, or a state-estimator design). The current estimated cutting rate may then be compared with a desired cutting rate and a signal provided to the user (for example a visual indicator on the screen with arrows or numbers, an aural indicator using pitch or loudness variations, or a tactile indicator using vibration or pressure to indicate the magnitude of the difference). Similarly, since plunge-through can be detected by a sudden increase in the tool velocity in the direction of drilling, such an event can be used, in certain embodiments which may include a control communication link to the tool, to reduce or shut off power to the drill to prevent inadvertent damage to underlying structures or to generate some other indication (for example visual, auditory or tactile) to alert the user to this event. For example in particular, in an embodiment as described elsewhere in this description in which navigation unit 1 is powered from the drill battery, a control connection to the drill may be included.

Figure 28:
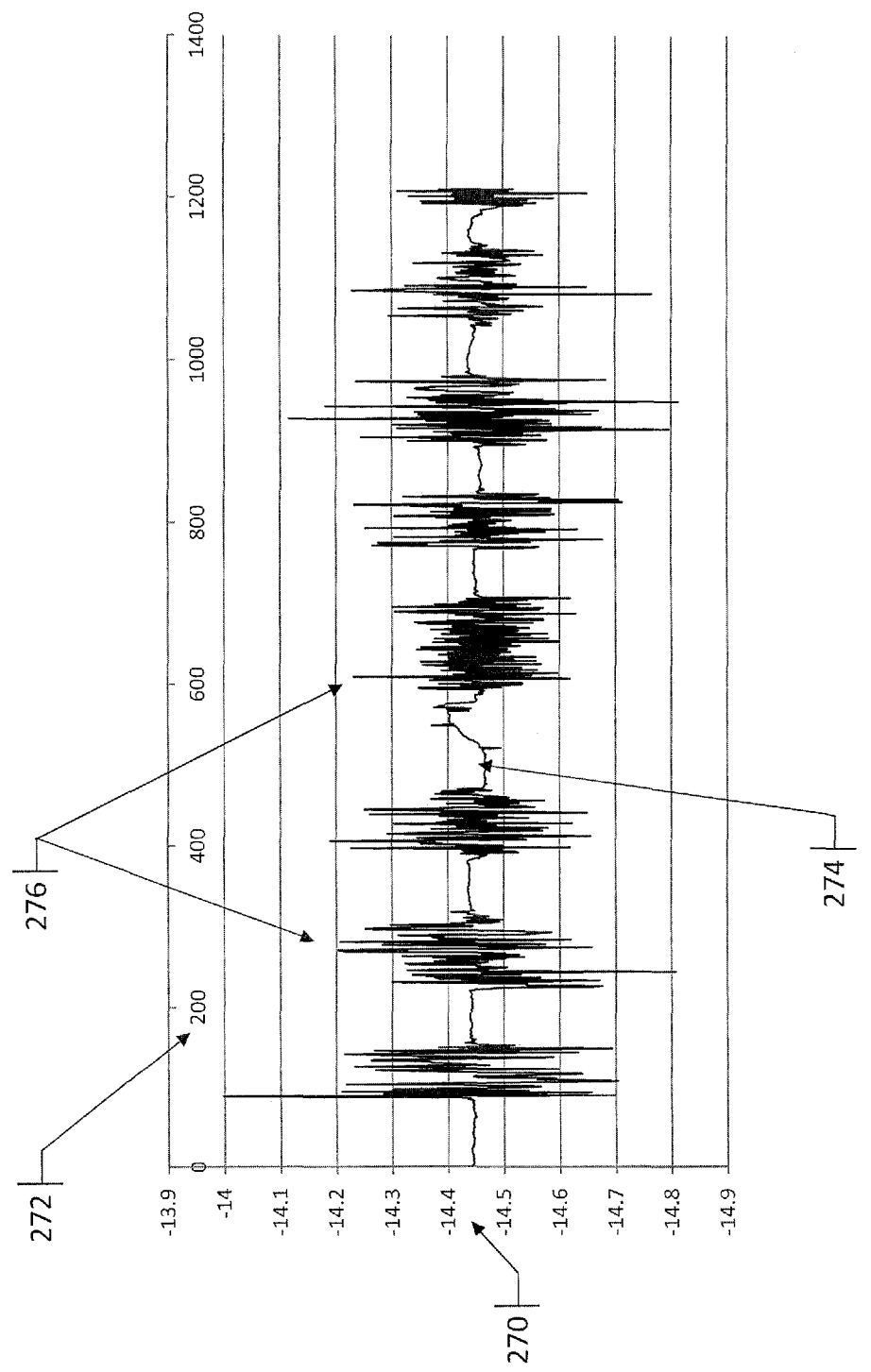
FIG. 28 shows an example plot of reference sensor readings when a drill motor of an attached drill is started and stopped, creating external magnetic fields that affect navigation system measurements.

In the exemplary embodiment, the data recorded is time versus the distance travelled by unit 1 relative to sensor 10 along drill axis 5 while the coaxiality of drill axis 5 and hole 38 is within predetermined limits and the drill motor is on, where the drill has an electric motor and the state of the drill motor may be determined using data from reference sensor 8 as described in FIG. 28. These conditions indicate that the user is likely drilling along the target drilling path. The time versus the distance data is used to estimate the length of a drilled hole traversing a bone so that the correct locking screw length may be quickly determined.

An example of such data is shown in time versus distance trace 57. When drilling through a femur or other long bone, for example, we have observed that there may be several characteristic points and regions in trace 57 that may be recognized by analysing location and time data of drill tip relative to the sensor, including entry point 59 which indicates where the drill tip enters the bone at the start of drilling and exit point 61 where the drill tip exits the bone between which is the estimated depth of drilling 63 which can be reported to the user. Both points have the characteristic of a period of slow advancement along the drilling path as the drill cuts through cortical bone before or after the point, followed by a sudden increase in advancement speed as the drill bit exits the cortex, and may therefore be detected automatically by searching trace 57 for areas falling within a range of predetermined motion parameters.

Going through trace 57 in more detail, during the pre-drilling phase of initial aiming (before active drilling begins), there will likely be a positioning phase where the drill tip may advance and retreat, as well as be adjusted parallel to the bone surface, before settling down. When this motion settles to the drill tip being static and close to the axis, with drill angle likely varying and the drill motor likely off, trace 57 is flat at region 336. Region 337 of relatively steady progress along the target axis, combined with drill angle being close to alignment (and optionally detecting a motor-on state), indicates the drilling rate through the near cortex. After plunging through the near cortex as indicated by a sudden increase in speed at region 338, there is a region of higher speed progress through the cancellous bone and nail hole at region 339. Progress slows again at region 340 of drill feed rate though cortical bone. Finally rate will likely increase again suddenly at region 341 after which the user should stop advancing the drill at flat region 342. The start of region 337 of steady slope within a range of expected drill feed rates indicates entry point 59, and similarly the end of region 340 indicates exit point 61. Entry point 59 may be recognized after a small amount of travel from region 336 as shown. One ordinarily skilled in the art will recognize that different applications will produce different characteristic traces 57, and that various thresholds, ranges, and estimation factors may need to be determined by experimentation for various materials, tools, cutting tool types, and the like in order to detect or estimate the desired regions and points of trace 57.

Figure 9A:
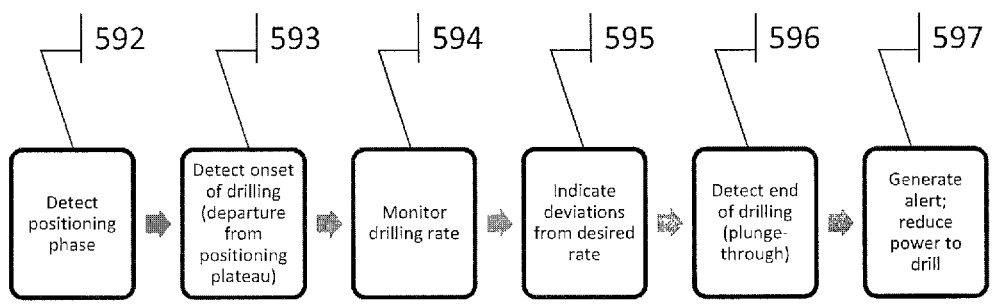
FIG. 9a shows a flowchart of the targeting and user interface method described in FIG. 9.

FIG. 9a shows a flowchart of a drill-travel-detection and drilling depth estimation method. At step 592, a positioning phase is detected by recognizing the drill point to be near the target axis but not progressing along it. In step 593 a drilling phase is detected by the start of progress along the target axis within an alignment tolerance zone, optionally coupled with a drill motor on state. In step 594 the rate of progress along the axis is monitored and compared to selected thresholds, and reported to the user in step 595. A rapid increase in rate exceeding selected thresholds is detected at step 596 and related warnings and actions may be applied at step 597.

Another aspect of the invention provides a tool comprising a user interface unit. For example the tool may comprise a drill and the interface unit may comprise a touchscreen display. The user interface unit may be mounted or mountable directly to the tool and may also be detachable from the tool. In other embodiments the user interface unit is mounted or mountable to an attachment for the tool and may also be detachable from the attachment. In other embodiments the user interface unit is adjustable relative to the tool such that the user may move the interface unit to a suitable position when the tool orientation is changed. For example the user interface unit may be a visual display screen attached via a swivel joint to a drill. For another example the user interface unit may be a visual display screen attached via a swivel joint to a drill chuck, which in turn attaches to a drill.

In other embodiments the user interface unit may detect the direction of gravity and adjust the orientation of an image displayed on the unit to a predetermined relationship to gravity. In other embodiments the user interface unit may detect the relative orientation of the unit to a reference direction defined by a navigation system and adjust the orientation of an image displayed on the unit to a predetermined relationship to the reference direction. For example the user interface unit may comprise a visual display screen and an accelerometer, which in some embodiments may communicate with a second accelerometer attached to a field generator or a sensor of a navigation system.

Each feature of a tool comprising a user interface and display described above may be advantageous individually or in combination with some or all of the other features described. Other embodiments within the scope of the invention may include a subset of the advantageous features described above, and described in more detail in example embodiments below.

Figure 10:
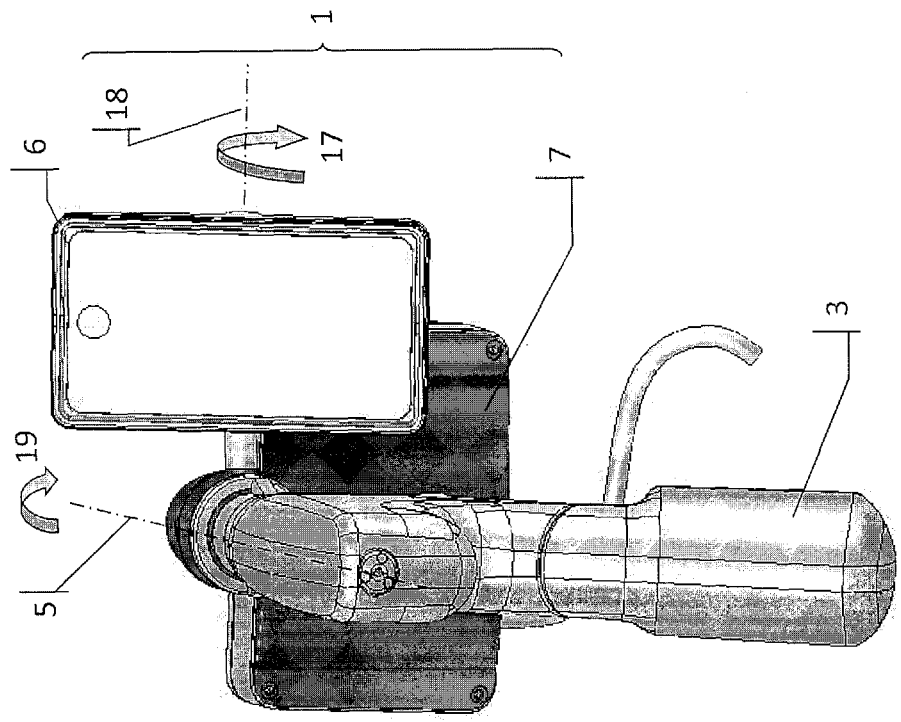
FIG. 10 shows an example of a user interface unit mounted to a drill according to one embodiment of the invention, with a display screen in position for drilling with the drill upright and pointing forward and away from the user's body, with the user holding the drill in their right hand.

FIG. 10 shows navigation unit 1 including user interface unit 6 is shown mounted to drill 3. A feature of user interface unit 6 is that it is integrated with unit 1, and in turn drill 3 when unit 1 is attached to drill 3, so that the display and user interface functions are easily accessible to the drill user during use and the user's attention may remain directed towards the working area of unit 1 and/or drill 3 during use. In various embodiments this integration may be provided by mechanical arrangements such as making unit 6 an integral part of unit 1 or by a bracket, fastener, snap-fit mechanism, or friction fit. In the exemplary embodiment shown unit 6 mounts to unit 1 via rotating ring 13, stud 49, and accompanying elements depicted in detail in FIG. 13 and FIG. 14.

Another feature of user interface unit 6 is that it may be attached and detached as required by the user during use manually and without the use of separate tools. In various embodiments unit 6 may be detachably integrated with unit 1 using various mechanical arrangements such as hand-operated fasteners, snap-fit mechanisms, threaded connections, detent mechanisms, quarter-turn style quick release joints or fasteners, and the like. In the exemplary embodiment shown unit 6 removably attaches to unit 1 via stud 49, clasp 69, and accompanying elements depicted in detail in FIG. 14.

Another feature of user interface unit 6 as integrated with navigation unit 1 is that user interface unit 6 may be adjustable to various positions and orientations relative to the rest of unit 1 and in turn drill 3, so that the user may select a suitable viewing and access position of user interface unit 6 as unit 1 and/or drill 3 are moved to different positions and orientations. In various embodiments the integration of unit 6 may be made adjustable by use of various mechanical arrangements such as adjustable arms or brackets, linkage mechanisms, sliding fit mechanisms, swivel joints, spherical joints, and the like. In the exemplary embodiment shown unit 6 is adjustable relative to unit 1 via two separate swivel joints incorporating rotating ring 13, stud 49, and accompanying elements as depicted in detail in FIG. 13 and FIG. 14.

Another feature of user interface unit 6 is that it remains at its current position during normal use until subsequent adjustment to a new position, without requiring the user to unlock, lock, remove, replace, tighten, loosen, use an additional tool, or take any other action other than moving user interface unit 6 to the desired position. In various embodiments this feature may be provided by linkage arrangements with friction joints and/or springs, detent mechanisms, and the like. In the exemplary embodiment shown unit 6 maintains the selected position relative to unit 1 via detent mechanisms including ball plungers 71 and 27 and accompanying elements depicted in detail in FIG. 14, FIG. 15, and FIG. 16.

Another feature of user interface unit 6 is that it may have predetermined ranges of adjustability relative to unit 1 that prevent the user from moving unit 6 to various disadvantageous positions, for example positions where unit 6 may interfere with the function and performance of field generator 7 or drill 3. In various embodiments this feature may be provided by various mechanical stop or link arrangements. In the exemplary embodiment shown the rotation of unit 6 about one axis of adjustment is limited by boss 31 and groove 33 depicted in detail in FIG. 15 and FIG. 16.

For embodiments in which unit 6 includes a visual display and unit 6 is integrated with a tool that may be used in various positions relative to a target, it is advantageous to determine the direction of gravity in real time so that the image displayed by unit 6 may be oriented in a selected way relative to gravity regardless of the orientation of the tool. Orientation data may be provided by incorporating an accelerometer into unit 6.

It is advantageous for embodiments in which the orientation of the field generator may change during use (for example when the field generator is integrated with a tool that may be used in various positions) to determine the orientation of unit 6 relative to the field generator so that the image displayed by unit 6 may be oriented in a selected way relative to the field generator or in turn relative to any sensor having a known location relative to the field generator. Relative orientation data may be provided by sensors that generate a signal indicative of the orientation of the user interface unit relative to the field generator, such as proximity sensors, electrical contacts, optical encoders, and the like. Alternately the relative orientation data may be provided by incorporating accelerometers in both unit 6 and at a fixed location relative to field generator 7, both producing signals indicative of the direction of gravity, and comparing the two gravity directions to determine the relative orientation.

Now looking at the exemplary embodiment in more detail, navigation unit 1 has axis 5. User interface unit 6 comprises an electronic touchscreen display in a housing, and may additionally include user interface devices such as buttons, switches, touchpads, and the like that may be operated through an isolation bag or surgical drape. Navigation unit 1 comprises housing 9, rotating ring 13 onto which user interface unit 6 mounts, and retainer 15. In the embodiment shown field generator 7 is included in surgical navigation unit 1. One ordinarily skilled in the art will recognize other possible embodiments that do not include field generator 7 or other navigation system components, wherein the targeting information displayed on user interface unit 6 is obtained by methods that do not require a field generator, such as optical tracking. User interface unit 6 is shown adjusted to a position suitable for a right-handed user drilling with drill 3 upright, pointing forward and away from the user's body.

Figure 10A:
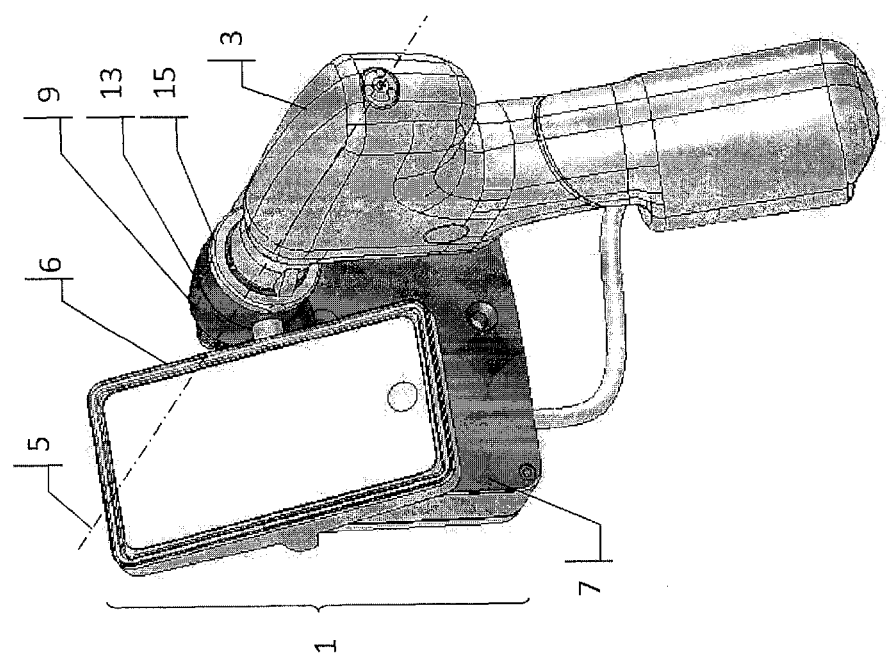
FIG. 10a is similar to FIG. 10, but with the screen adjusted to a position for a user holding the drill in their left hand.

With reference to FIG. 10a, user interface unit 6 is shown adjusted from the position shown in FIG. 10 by approximately one hundred and eighty degrees about drill axis 5 in direction 19 and tilted in direction 17 about axis 18, to obtain a viewable position of display 6 for a left-handed user drilling with drill 3 upright, pointing forward and away from the user's body.

Figure 11:
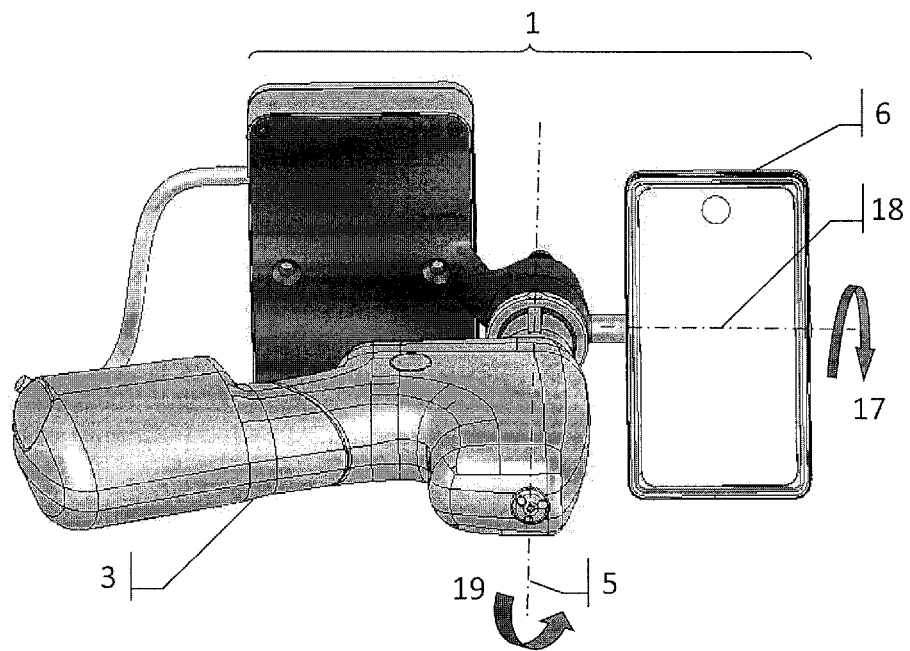
FIG. 11 shows the exemplary user interface unit mounted to a drill with the screen in position for drilling with the drill turned to a horizontal position and pointing forward and away from the user's body.

With reference to FIG. 11, in accordance with an embodiment of the invention, navigation unit 1 is mounted to drill 3 with screen surface positioned for drilling with drill 3 turned to a horizontal position and pointing forward from the user's body. From the position shown in FIG. 10a, user interface unit 6 has been rotated counterclockwise, in direction 19 about axis 5 approximately ninety degrees, and may be adjusted in direction 17 about axis 18 to a suitable viewing angle.

Figure 11A:
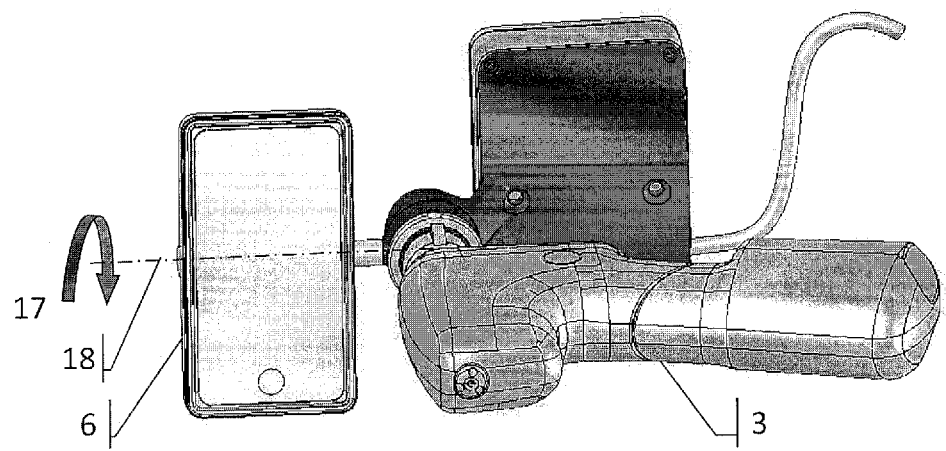
FIG. 11a is similar to FIG. 11, but with the screen adjusted to a position for a user holding the drill in the opposite horizontal orientation.

With reference to FIG. 11a, if the user needs to hold the drill 3 in the opposite horizontal orientation from that shown in FIG. 11, user interface unit 6 may be rotated about axis 18 in direction 17 to a suitable viewing angle.

Referring to FIGS. 10, 10a, 11, and 11a, the adjustability of the position of user interface unit 6 relative to drill 3 allows the user to maintain a clear line of sight along drill axis 5 to the area being drilled in a variety of drilling positions.

Figure 12:
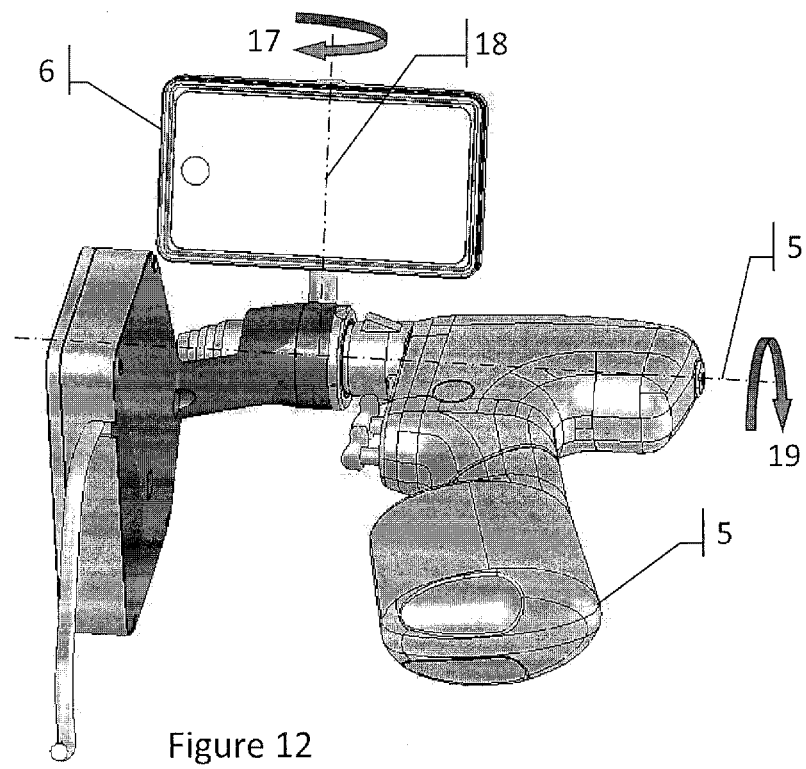
FIG. 12 shows the exemplary user interface unit mounted to a drill with the screen in position for drilling with the drill turned to a horizontal position and pointing to the user's left.
Figure 12A:
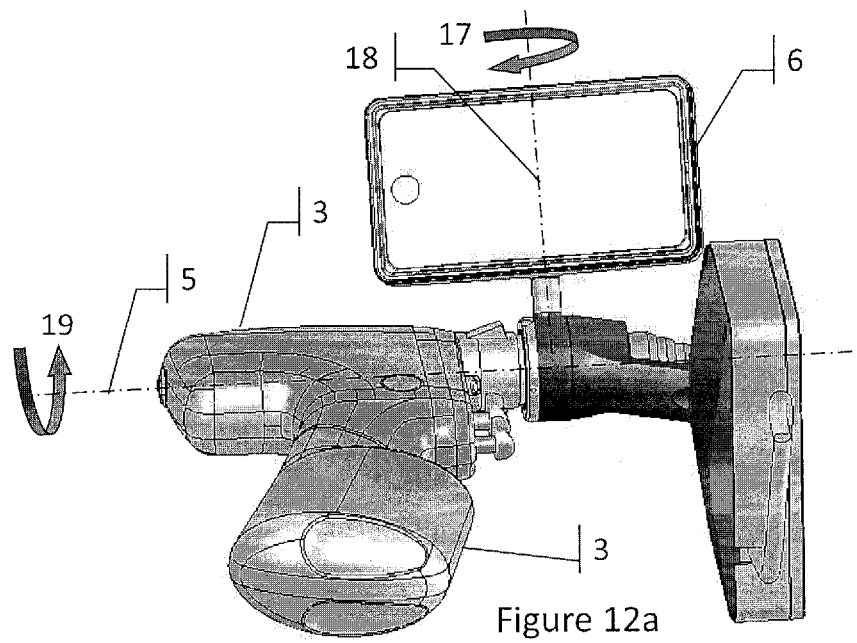
FIG. 12a is similar to FIG. 12, but with the screen adjusted to a position for drilling with the drill turned to a horizontal position and pointing to the user's right.

With reference to FIG. 12, in accordance with an embodiment of the invention, user interface unit 6 is mounted to drill 3 and adjusted to a position suitable for drilling with drill 3 turned to a horizontal position and pointing to the user's left. From the position shown in FIG. 11a, user interface unit 6 has been rotated approximately ninety degrees in direction 17, and forty-five degrees in direction 19. Referring also to FIG. 12a, opposite adjustments may be made to obtain a suitable position and angle of display 6 when drill 3 is used in a horizontal position and pointing to the user's right.

Referring to FIGS. 10 through 12a, one skilled in the art will recognize that various degrees of freedom and ranges of adjustability of user interface unit 6 relative to navigation unit 1 may be selected depending on the range of drilling positions expected in the particular application and the desired allowable positions of unit 6. For example in certain embodiments, adjustability in either direction 17 or direction 19 may not be required. For another example it may be advantageous to restrict unit 6 from being positioned in the region directly between field generator 7 and drill 3 due to clearance required for operating drill 3 and/or to limit the effects of measurement distortion from unit 6. For another example it may be advantageous to restrict unit 6 from being rotated to a position where the display screen faces distally towards the tip of drill bit 2. Certain other embodiments may require additional degrees of freedom.

Figure 13:
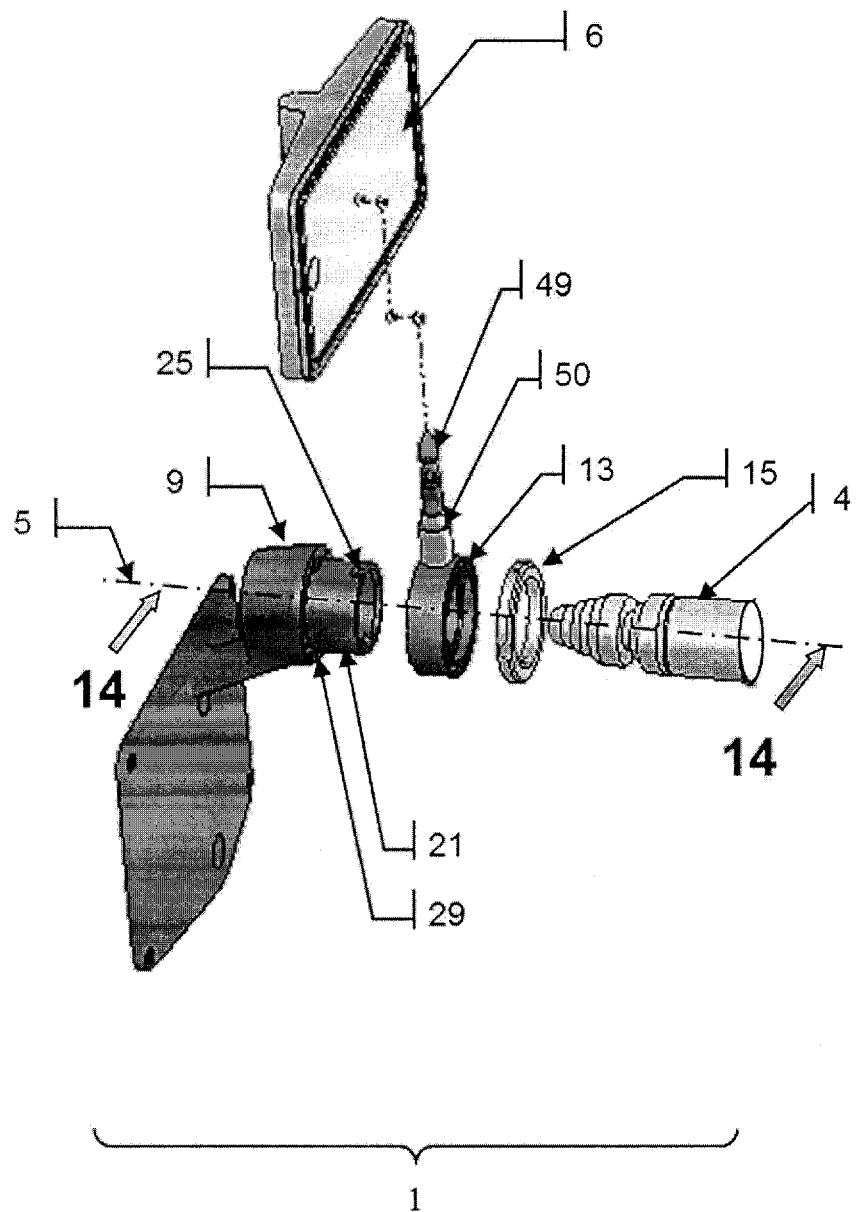
FIG. 13 shows an exploded view of the exemplary embodiment of the invention, showing a detachable user interface unit, a mounting unit, and a movable joint between the display and mounting units.

With reference to FIG. 13, in accordance with an embodiment of the invention, an exploded view of navigation unit 1 is shown illustrating one example of a structure that allows two degrees of freedom between unit 6 and chuck 4, one being rotation about drill axis 5 and the other being rotation about an axis of unit 6 that is normal to and intersecting axis 5. Housing 9 has outer cylindrical surface 21. Housing 9 is fixed to drill chuck 4 (see FIG. 8) which in turn mounts to drill 3. Rotating ring 13 slides over cylindrical surface 21. Retainer 15 has pins 23 (not shown, see FIG. 14) extending radially inwards and slides over cylindrical surface 21 such that pins 23 engage slots 25 in housing 9, and when fully engaged, retainer 15 is fixed to housing 9 in a position that pushes ball plungers 27 (not shown, see FIG. 14) of rotating ring 13 against face 29 of housing 9. Rotating ring 13 can then rotate about cylindrical surface 21 and axis 5. This arrangement allows quick and easy disassembly of retainer 15 and rotating ring 13, without requiring tools, for cleaning and sterilization. Drill 3, field generator 7 and cover 24 (seen in FIG. 8) are not shown for clarity. Rotating ring 13 also includes stud 49 and collar 50, to which user interface unit 6 is removably attached as described below.

Figure 14:
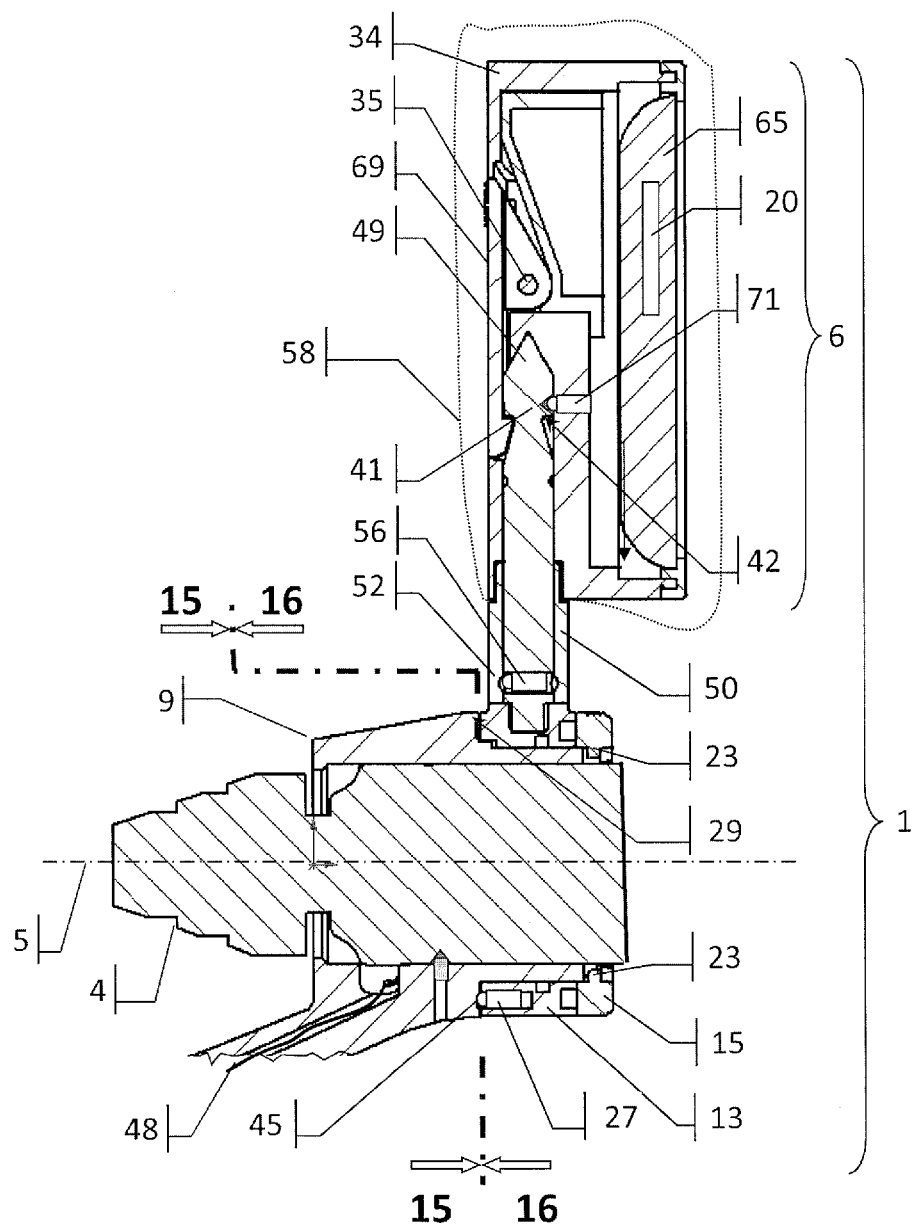
FIG. 14 is a section showing the exemplary mounting unit installed on a drill chuck.
Figure 15:
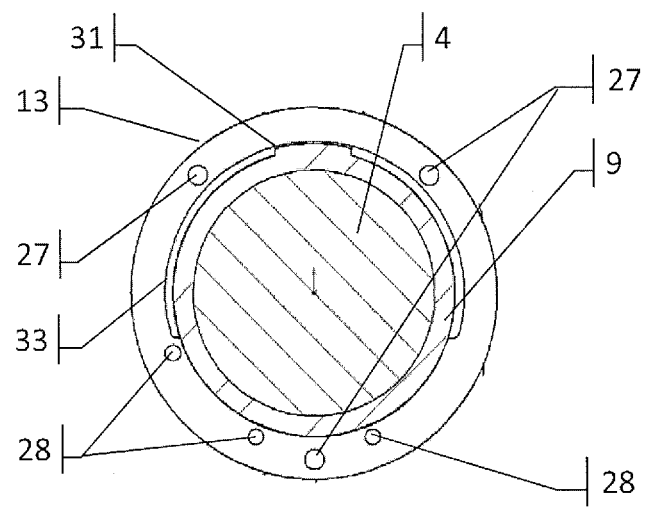
FIG. 15 is a section view taken from FIG. 14, normal to the drill axis, looking towards the drill user.
Figure 16:
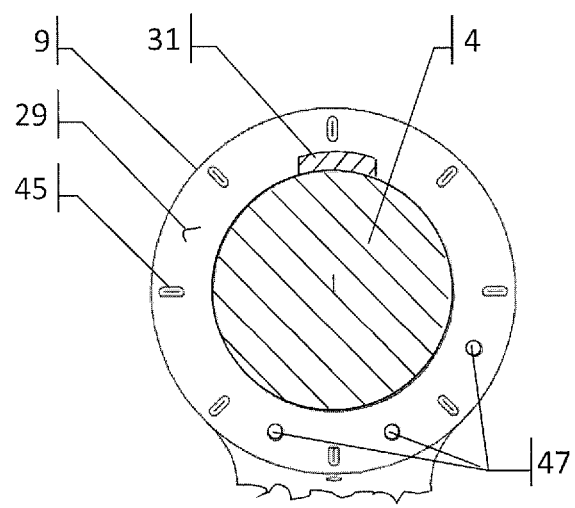
FIG. 16 is a section view taken from FIG. 14, normal to the drill axis, looking towards the drill bit.

With reference to FIG. 14, FIG. 15, and FIG. 16, in accordance with an embodiment of the invention, a section through drill axis 5 is shown with navigation unit 1 assembled and user interface unit 6 in place. Chuck 4 is fixed within housing 9 as described in FIG. 8. Housing 9 also has three proximity sensors 47 (visible in FIG. 16) installed flush with face 29 and wiring 48 leading from proximity sensors 47 to the navigation system console. Rotating ring 13 includes three ball plungers 27 (one shown, all three visible in FIG. 15) and three permanent magnets 28 (visible in FIG. 15). Retainer 15 has pins 23 that engage slots in housing 9 to lock retainer 15 in position relative to housing 9, such that ball plunger 27 installed in rotating ring 13 rolls along face 29 as rotating ring 13 is rotated by the user about axis 5. Face 29 has radial grooves 45 spaced at intervals such that ball plunger 27 engages a groove 45 at selected intervals of the rotation of ring 13. The releasable joint between user interface unit 6 and stud 49 of rotating ring 13 is also shown. User interface unit 6 comprises housing 34, electronic touchscreen 65, clasp 69 which pivots in housing 34 on pin 35 and is spring biased in a counterclockwise direction, and ball plunger 71 which engages divot 41, which is one of a set of twelve divots circumferentially spaced around the outer cylindrical surface of stud 49 at thirty degree intervals. To install user interface unit 6 onto mounting unit 2, the user slides user interface unit 6 onto stud 49 until clasp 37 engages shoulder 42 of stud 49 with an audible 'click' sound. As user interface unit 6 is rotated about stud 49, ball plunger 39 engages a divot 41 and stops with an audible 'click' sound. User interface unit 6 remains in that position until it is rotated by the user by thirty degrees and ball plunger 39 engages the next divot 41. Collar 50 is a clearance fit over stud 49 and circumferential groove 52 in collar 50 engages ball plunger 56 in stud 49 with a clearance fit, such that collar 50 is free to rotate about stud 49 but will not slide off stud 49 unless pulled off by the user for cleaning and sterilizing. Collar 50 allows user interface unit 6 to be enclosed in a sterile plastic drape 58 before installation onto stud 49, allowing user interface unit 6 to be used in the sterile field without having to be sterilized. Drape 58 is made of thin clear plastic material which is pierced as the user slides user interface unit 6 over stud 49, and when user interface unit 6 is in position as shown, the edge of the resulting pierced hole in drape 58 is compressed between housing 34 and collar 50 thereby preventing the user from having direct contact with any surface of user interface unit 6. As user interface unit 6 is rotated on stud 49 collar 50 is free to rotate with housing 34 thereby preventing twisting or tearing of drape 58. Electronic touchscreen 65 is a touch screen unit comprising a battery power source, a computer, and a wireless communication device 20 to receive and transmit information to the navigation system. A suitable electronic display screen is an EMX-270 Embedded Mobile Device unit from Compulab™ (Haifa, Ill.). Wireless communication device 20 eliminates the need for a wired connection between user interface unit 6 and the navigation system console, (or, referring also to FIG. 7, to field generator 7 and then on to the navigation system via cable 73) which is important due to the degrees of freedom between user interface unit 1, field generator 7, and the navigation system console located outside the sterile surgical field.

Referring to FIG. 15, a section through chuck 4 and housing 9 taken from FIG. 14 and looking proximally on retaining ring 13 is shown. Rotating ring 13 has three ball plungers 27 and three permanent magnets 28 installed at forty five degree intervals, with magnets bonded in place. Rotating ring 13 also has groove 33 into which boss 31 of housing 9 fits with a clearance fit.

Referring to FIG. 16, a section through chuck 4 and housing 9 taken from FIG. 14 and looking distally on face 29 of housing 9 is shown. Face 29 has radial grooves 45 evenly spaced at forty-five degree intervals about axis 5 (not shown, visible in FIG. 14), so that rotating ring 13 (not shown, visible in FIGS. 13 and 14) stops with an audible 'click' at each interval in its travel and remains in that position until it is moved by the user to the next forty-five degree interval position. Housing 9 also has boss 31 which fits in groove 33 of rotating ring 13 (see FIG. 15), and proximity sensors 47 bonded in place flush with face 29 and located at forty five degree intervals as shown.

Referring to FIGS. 15 and 16 together, groove 33 and boss 31 limit the rotation of rotating ring 13 to one hundred and eighty degrees, and in combination with radial grooves 45 defines five possible rotational positions of ring 13 relative to clamp portion 9. At each forty-five degree interval in the rotation of rotating ring 13, at least one of the three magnets 28 is aligned with at least one of the three proximity sensors 47, and at each of the five possible forty five degree interval positions of rotating ring 13 relative to housing 9, a unique combination of proximity sensors 47 senses the presence of a magnet 28. Referring to FIG. 14, via wiring 48 to the navigation system console, the unique combination of activated proximity sensors is sent as a signal to the navigation system to indicate the user interface unit 6 position relative to housing 9, and allowing the orientation of the image on touchscreen 65 to be rotated as desired.

Figure 16A:
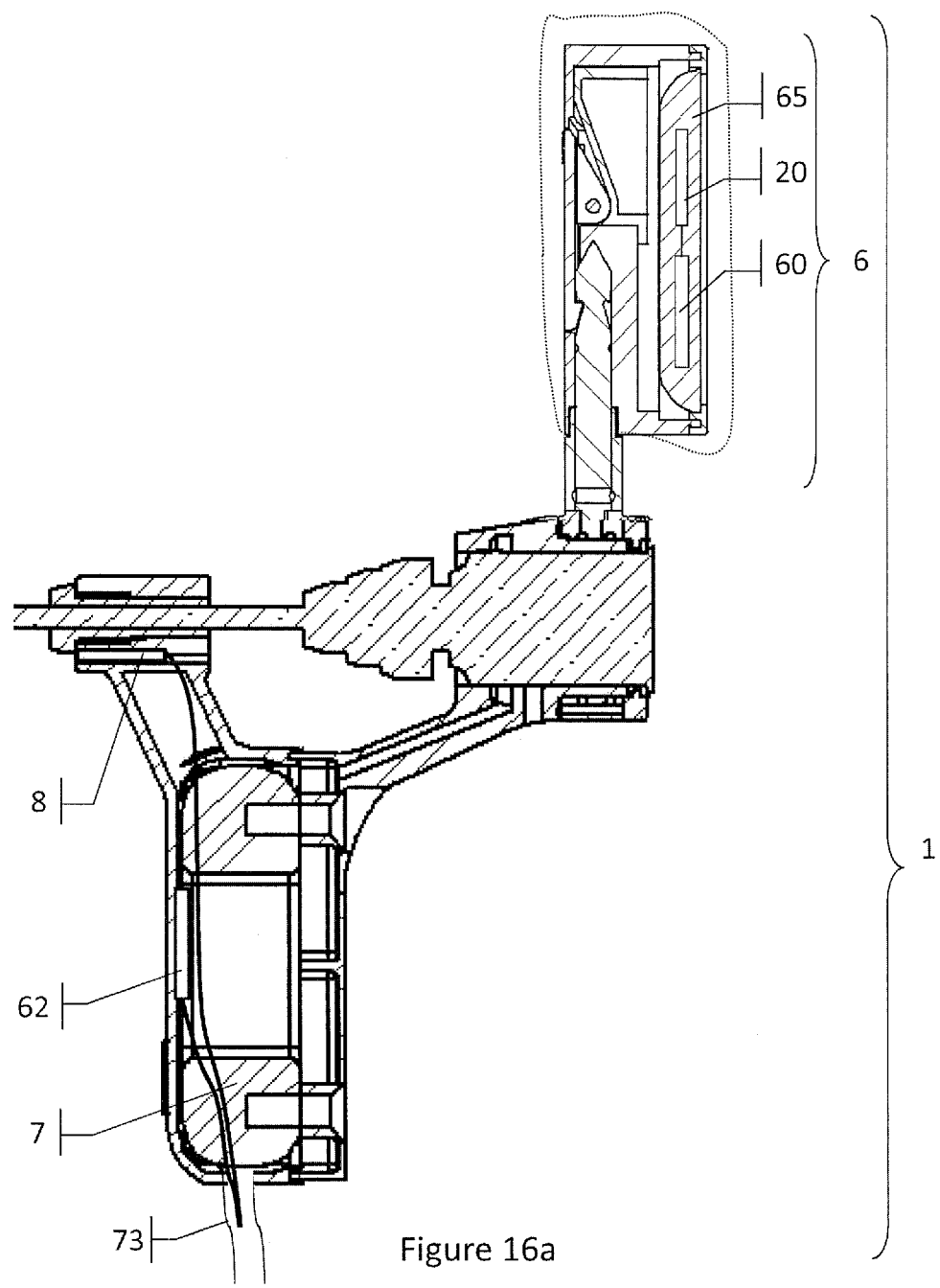
FIG. 16a shows a partial cross-sectional view of an embodiment of the navigation unit without proximity sensors, magnets and wiring.

Referring to FIG. 16a, an embodiment of the invention without proximity sensors 47, magnets 28 and wiring 48 is shown in a section view through navigation unit 1, similar to FIG. 14. In this embodiment electronic touchscreen 65 additionally includes accelerometer unit 60 which senses the direction of gravity relative to user interface unit 6 and communicates this information to touchscreen 65, and in turn to the navigation system via wireless communication device 20. Field generator 7 includes an embedded accelerometer 62 which generates a signal indicative of the direction of gravity which is sent to the navigation system via field generator cable 73. By comparing the gravity direction vectors of accelerometers 60 and 62 the relative orientation of user interface unit 6 to field generator 7 can be determined and the image displayed on unit 6 can be aligned relative to a selected sensor being tracked by the navigation system. In another embodiment of the invention, for example for applications where the orientation of the target sensor is known relative to gravity or in which aligning the image shown on unit 6 relative to gravity is sufficient, accelerometer 62 is not required, accelerometer 60 is used alone (in place of proximity sensors 47 magnets 28 and wiring 48), and the image on touchscreen 65 is aligned to the direction of gravity using the signal from accelerometer 60.

Figure 17:
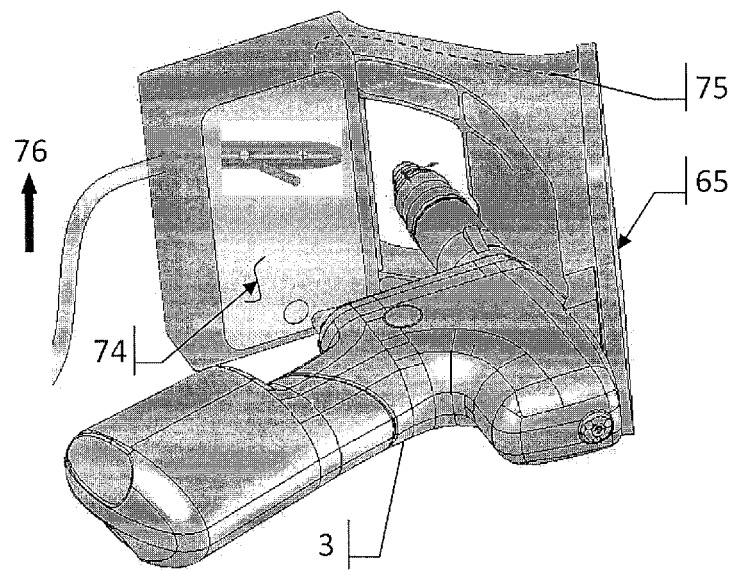
FIG. 17 shows an alternate embodiment of the invention having multiple display screens rather than a movable joint between a user interface unit and the drill.
Figure 17A:
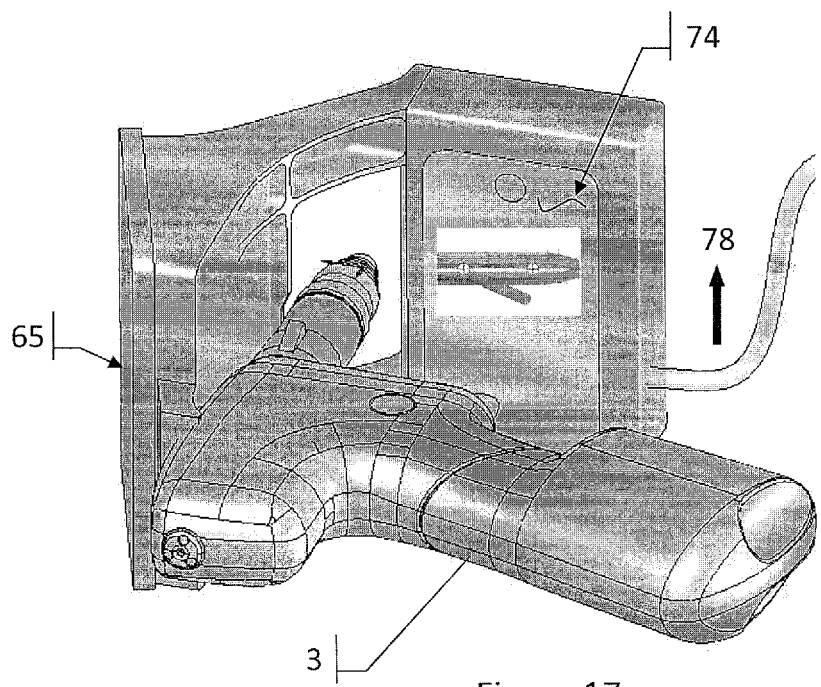
FIG. 17a shows the alternate embodiment of FIG. 17, in a second drilling position.

With reference to FIGS. 17 and 17*a*, in another embodiment a plurality of display screens are mounted to the drill at selected locations, eliminating the need for degrees of freedom between user interface unit 6 and housing 9. Auxiliary display screen 74 is powered and supplied with signals from touchscreen 65 by wiring 75 (but may alternately be similar to touchscreen 65 having a wireless communication device, internal battery, and an accelerometer, and may be a different size or shape). The horizontal drilling position shown in FIG. 17 is detected by accelerometer 60 (seen in FIG. 16*a*), and auxiliary screen 74 which is visible to the user in this drilling configuration is activated and the image on screen 74 is adjusted to the appropriate orientation and moved in direction 76 to optimize visibility. When drill 3 is operated in the position shown in FIG. 17*a*, based on signals from accelerometer 60 (seen in FIG. 16*a*) the image on screen 74 is rotated one hundred and eighty degrees relative to screen 74 and also moved in direction 78 to optimize visibility to the user.

Another aspect of the invention provides a user interface indicating the relationship of a tool to a target and also indicate tolerance limits of alignment of the tool to the target. For example the interface may comprise a display screen showing a drill icon representing a drill relative to a graphic of a target hole, and may also comprise indicators of coaxiality of the drill to the hole within specified parameters.

In some embodiments the user interface may indicates to the user where the tool is in real time relative to the target. The indication may have various forms depending on the particular targeting task, for example the task could be aligning two planes to be coplanar, aligning a tool tip with a point without indicating the angle of the tool, or aligning a tool axis to be coaxial with a target axis as described in the exemplary embodiment. The representation of the tool and the target may also be done various ways, for example the target may be shown in a fixed location on the display screen with the representation of the tool moving on the display, or vice versa, or the indication may be a hybrid in which the tool representation moves on the display in translation but the target moves on the screen in rotation, or vice versa. We have observed that users are successful at targeting in the exemplary drill alignment embodiment when a drill icon moves in both translation and rotation on the display screen while the target remains at a fixed position on screen. We have also observed that many users understand the interface well when the drill is represented by a graphic icon that looks like a drill bit and chuck.

In some embodiments the interface may automatically adjust field of view and magnification based on detected conditions of alignment. This enables optimization of view parameters without additional input from the user, such as a requirement to press a zoom in or zoom out command or to have a separate selection dialog to specify a target to zoom in on, and the like. For example in an embodiment the display shows a large field of view showing all potential targets, and then centers aligns with and zooms in on a particular target axis when the user has been within selected limits of alignment to the particular target for a selected minimum continuous time period, in order to allow fine adjustment of alignment. Similarly the embodiment infers when the user has backed away from a particular target and zooms out to a global view to allow the user to locate and select a different target. Different parameters and thresholds may be applied for zooming in and zooming out.

In some embodiments indication of one parameter of alignment being within tolerance may only be given if selected other parameters are also within tolerance. For example, we have observed better user response to the interface when acceptable angular alignment of a drill axis to a target hole axis is only indicated at times when the drill tip is simultaneously within an acceptable distance from the target axis. We have also observed that the preferred technique of many users is to align the drill tip within the acceptable tolerance range, establish a pivot point in the material being drilled if possible, and then rotate the drill into the acceptable angular tolerance range.

In some other embodiments the tolerance limit for one parameter of alignment may depend on at least one other parameter. We have observed better targeting results with many users when targeting limits of position and angle are related to each other rather than treated separately. For example if a tool tip point is located a certain distance from a target axis that is within the specified distance tolerance, and the angle between the tool axis and the target axis is also within a specified magnitude of angle tolerance, the direction of the angular error may lead the tip point closer or farther from the target axis as the tool advances along the tool axis. Therefore it may be an advantage to restrict the acceptable angular difference to those magnitudes and directions that maintain the tip point within its distance tolerance, or lead the tip point to a target region at a specified point along the target axis as the tool advances. It may also be an advantage to select a region of the target axis where distance from the tool tip to the target axis is most important, for example at the entrance to a target hole, and project the current tool path to this region to calculate the distance parameter of alignment rather than calculating distance to the target axis at the current tool tip point location. This method makes the angular tolerance limit a function of how far the tool tip is from the critical target region; the farther away, the closer the angle must be held to be aiming at the target. For example alignment between a drill axis and a target axis may have a magnitude of angle tolerance and a distance tolerance from the drill tip to the target axis, wherein the angle tolerance is reduced for certain directions depending on the location of the drill tip such that the projected drill axis passes through a selected tolerance zone. In an embodiment a positional alignment parameter may be the normal distance from a drill tip to a target axis and an angular intersection point of the projected drill axis and a selected plane near the target hole alignment parameter may be the normal distance from the target axis to the.

In another embodiment a positional alignment parameter may be the normal distance from the target axis to the intersection point of the projected drill axis and a first selected plane near the target hole, and an angular alignment parameter may be the normal distance from the target axis to the intersection point of the projected drill axis and a second selected plane near the target hole, the first and second planes defining a region of the target axis over which the coaxiality tolerance of the drill axis to the target axis is applied.

Each feature of a visual user interface described above may be advantageous individually or in combination with some or all of the other features described. Other embodiments within the scope of the invention may include a subset of the advantageous features described above, and described in more detail in example embodiments below.

Figure 18:
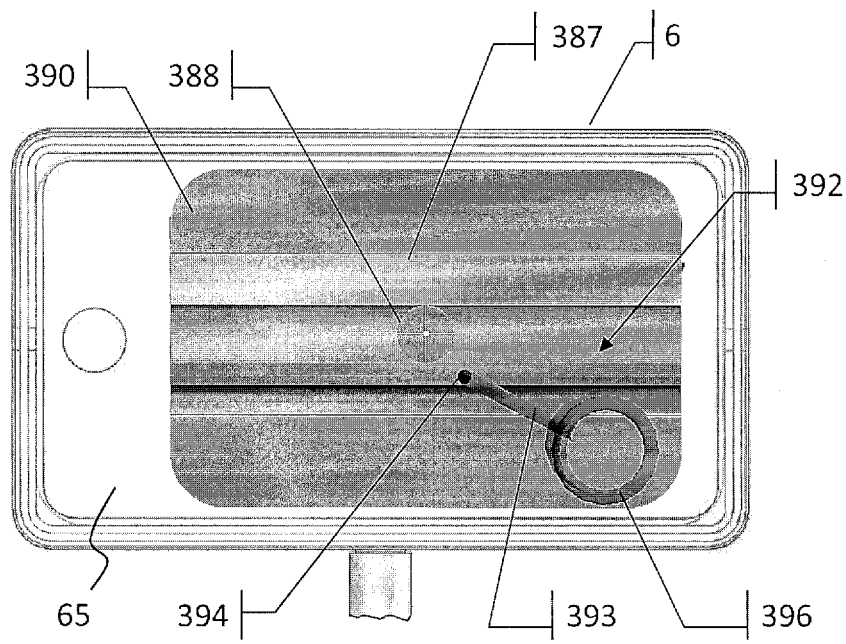
FIG. 18 shows an example user interface according to one embodiment of the invention during use in the exemplary application, with the drill approaching alignment with a locking hole.

FIG. 18 shows user interface unit 6 during targeting, with the drill approaching alignment with a locking hole. User interface unit 6 indicates to the user where the tool is in real time relative to the target. Drill icon 392 moves in both translation and rotation on screen 390 while the target, nail 37, remains at a fixed position on screen 390.

Drill icon 392 comprises a shank portion 393 connecting two separate indicators of successful alignment within a tolerance zone, one being tip indicator 394 indicating the position of the tip of drill bit 2, and the other being alignment indicator 396 representing a point on drill axis 5 closer to drill 3 and thus indicating orientation of drill axis 5.

Referring also to FIG. 7, during targeting display screen 390 shows a graphic representation 387 of nail 37 with hole 38 shown graphically by hole graphic 388 comprising the perimeter edge of hole 38 and crosshairs intersecting at the centre of hole 38. FIG. 18 shows the display zoomed in and centered on one target hole, the navigation system having detected that the drill tip has been within a selected distance from the hole axis continuously for at least a selected amount of elapsed time, as described in more detail in FIG. 18b. Tip indicator 394 is semi-transparent in its non-activated state, such that nail graphic 387 and hole graphic 388 are visible through tip indicator 394 when tip indicator 394 is in its non-activated state. Similarly alignment indicator 396 is also semi-transparent in its non-activated state, such that tip indicator 394, nail graphic 387, and hole graphic 388 are visible through alignment indicator 396 when alignment indicator 396 is in its non-activated state. Drill icon 392 is semi-transparent such that tip indicator 394, nail graphic 387, and hole graphic 388 are visible through drill icon 392 at all times. For example in the exemplary embodiment, tip indicator 394 and alignment indicator 396 are rendered in a semi-transparent gray colour when in their non-activated states, and turn to an opaque green colour when in their activated states. One ordinarily skilled in the art will recognize that many alternate graphic shapes may be used and many other differences between activated and non-activated states are possible such as visible and invisible, filled and outline, flashing and steady display, changing shapes, or changing fill pattern.

Figure 18A:
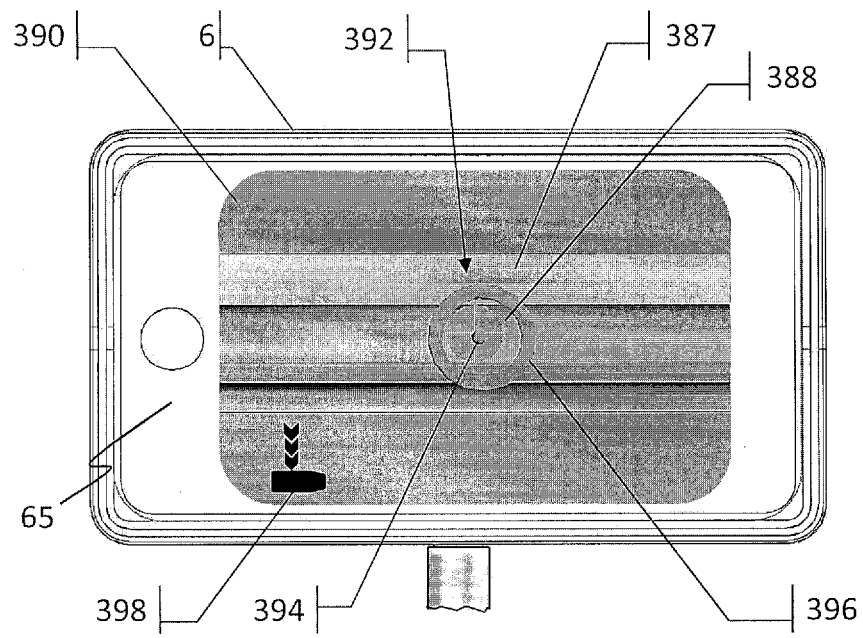
FIG. 18a shows the exemplary user interface of FIG. 18, but with the drill within alignment tolerance to a locking hole and with a depth indicator displayed.

FIG. 18a shows user display 6 with display screen 390 during targeting, with the drill within alignment tolerance with locking hole graphic 388 of nail graphic 387. In this view shank portion 393 (see FIG. 18) of drill icon 392 is not visible, and tip indicator 394 and alignment indicator 396 and depth indicator 398 are all shown in their activated states. Display 390 includes depth indicator 398 which indicates to the user that the tip of drill bit 2 as represented by tip indicator 394 is approaching the surface of nail 37, so the user has an indication of when drill bit 2 is about to enter locking hole 38. Depth indicator 398 is active and appears on display 390 only when tip indicator 394 is located within a predetermined range of distances from the plane through the Yh and Zh axes of locking hole coordinate system 136 (seen in FIG. 7), and also within a minimum normal distance to the Xh axis of locking hole coordinate system 136. Since the objective is only to indicate to the user approximately when to expect the drill tip to enter the target hole, depth indicator 398 may be a qualitative indicator and as such has three fill-bar style graphic segments which are displayed as filled progressively to qualitatively represent the approach of drill bit 2 to nail 37. Alternately depth indicator 398 may be a side view showing a real time representation of the drill tip approaching the target hole. One ordinarily skilled in the art will recognize that depth indicator 398 may be implemented in many different ways using different graphic elements, sound, text, quantitative information, or a combination of these indicators, and that depth indicator 398 may be active at all times, or activated by different or additional parameters such as the drill motor detected as being on (refer to FIG. 27 and FIG. 32).

Figure 18B:
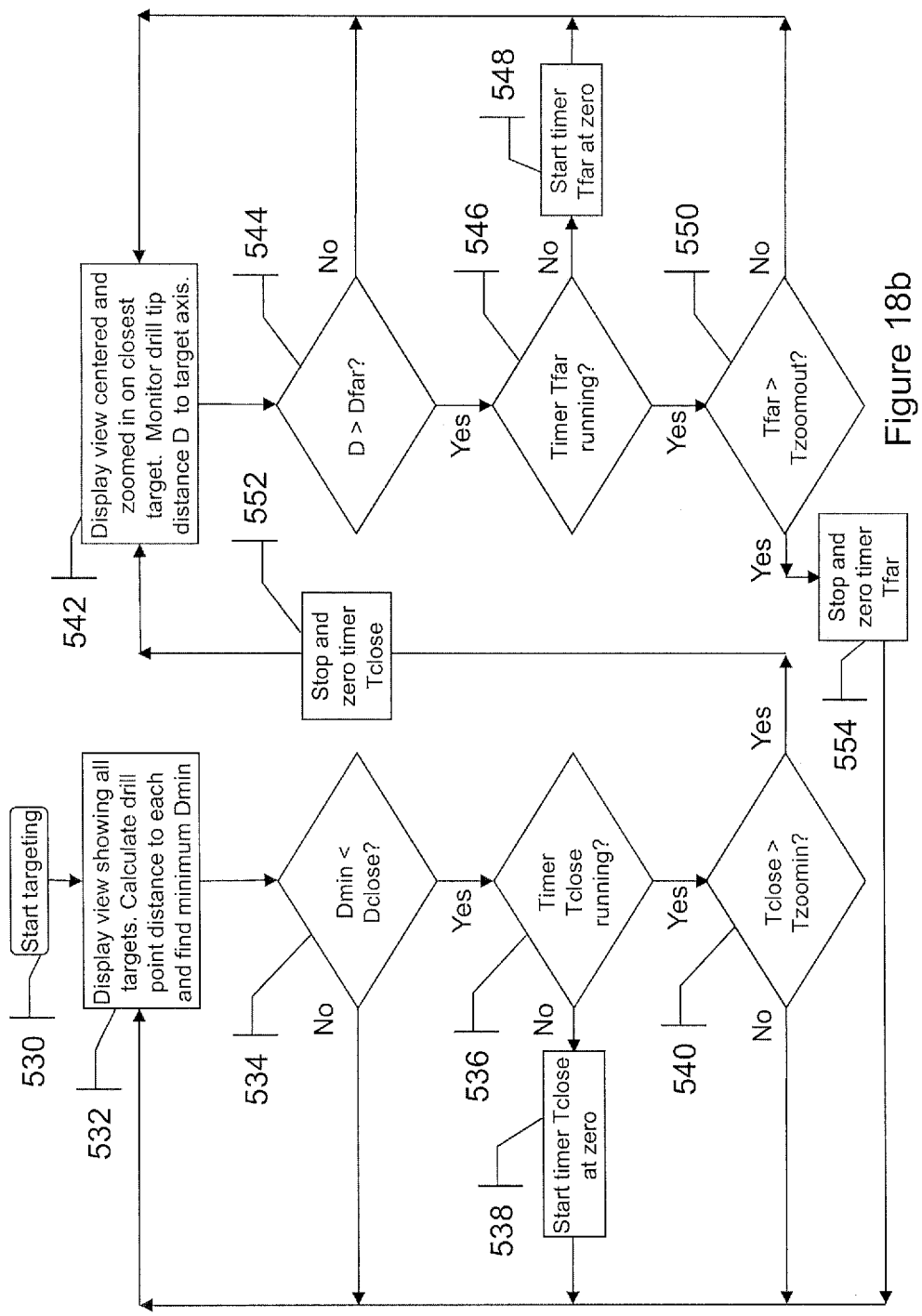
FIG. 18b shows a flowchart of a method for controlling field of view and magnification parameters of the user interface display.

FIG. 18b shows a flowchart of a method for controlling field of view and magnification parameters of the user interface display. At step 530 targeting mode is active which may occur when the targets are defined and the navigation system is tracking the tool relative to the targets. Initially a global view showing all targets is displayed in step 532, and a distance parameter from the drill tip to each target is calculated, for example the normal distance to each target hole axis. The minimum of these distances is found and compared to a selected threshold $D_{close}$ in step 534, and if the tool is within distance $D_{close}$ to any target, the state of a timer $T_{close}$ is checked in step 536. If $T_{close}$ is not already running, it is started from zero in step 538 and the system returns to step 532 remaining in a global view. If timer $T_{close}$ is already running, meaning that the tool has been near a particular target for some time, the value of that elapsed time near the target is checked against a selected threshold $T_{zoomin}$ in step 540. Once $T_{close}$ exceeds the zoom in threshold, timer $T_{close}$ is stopped in step 552 and the system changes the display to a zoomed in view centered on the target the tool has been near for the selected continuous amount of time $T_{zoomin}$ in step 542. Once zoomed in on a particular target the system checks for tool distance to the target to exceed a selected threshold $D_{far}$ in step 544, and if the tool has moved away timer $T_{far}$ is checked in step 546 and if not already running, started at zero in step 548. If timer $T_{far}$ is already running, meaning that the tool has been moved away from the current target for some time, the value of that elapsed time far from the target is checked against a selected threshold $T_{zoomout}$ in step 550. Once $T_{far}$ exceeds the zoom out threshold, timer $T_{far}$ is stopped in step 554 and the system returns to the global view in step 532.

One ordinarily skilled in the art will recognize that other parameters, for example speed and acceleration of the tool towards or away from a target, may be used in place of or in addition to time and distance. For example a characteristic motion of the tool such as a flicking motion or a rapid tilt in a particular direction may be defined, detected and used to change view parameters.

Figure 19:
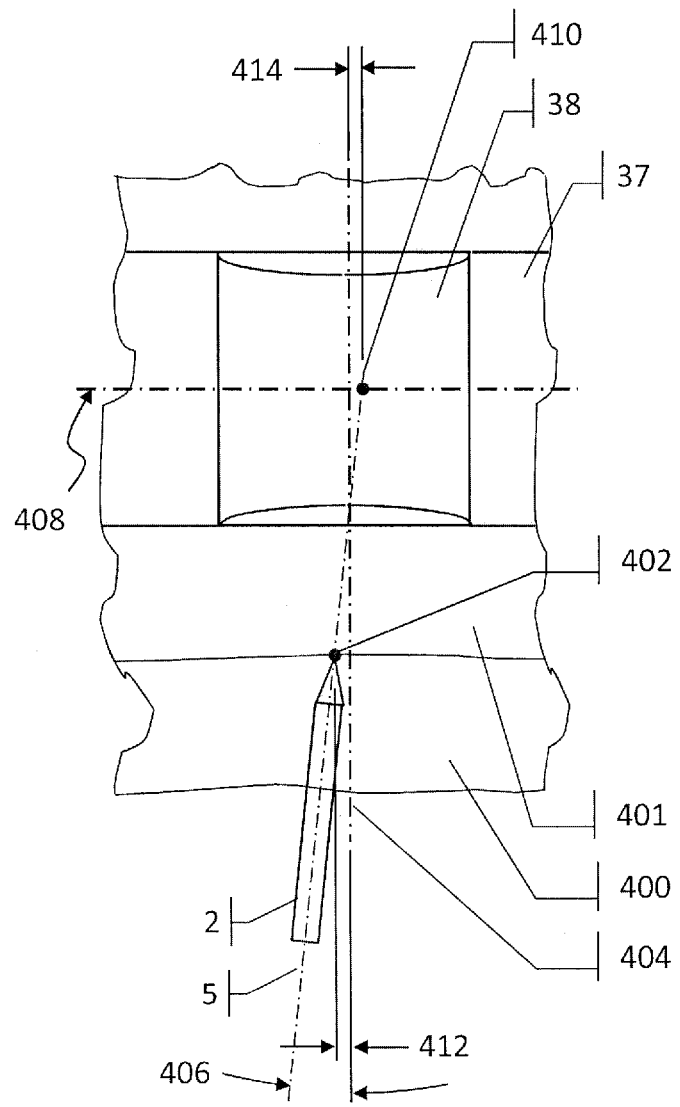
FIG. 19 shows a section view through a bone and implant during use of the exemplary embodiment in the exemplary application, with the drill aligned with a locking hole within predetermined limits.

With reference to FIG. 19, in accordance with an embodiment of the invention, a section view through a bone and implant with a drill bit approaching alignment with a locking hole in the implant is shown to illustrate an exemplary method of determining when the tool has reached an acceptable alignment with the target according to selected limits. One example of this method is described in detail as follows: Drill bit 2 has tip 402 and is shown passing through skin and underlying soft tissues 400 with tip 402 contacting bone 401. Drill axis 5 is coincident with the longitudinal centerline of drill bit 2. Drill bit 2 rotates about drill axis 5 during drilling. Locking hole 38 in nail 37 has hole axis 404 which is collinear with the Xh axis of locking hole coordinate system 136 (shown in FIG. 7). Drill axis 5 is shown at alignment angle 406 relative to the direction of hole axis 404. Plane 408 passes through the Yh and Zh axes of locking hole coordinate system 136 (shown in FIG. 7) and is therefore normal to hole axis 404 and also passes through the longitudinal axis of nail 37. Drill axis 5 intersects plane 408 at intersection point 410. Angle 406 is calculated as the acute angle between drill axis 5 and a vector normal to plane 408 passing through intersection point 410. During targeting, the position of drill tip 402 and the position and orientation of drill axis 5 relative to hole coordinate system 136 is monitored constantly, for example at a rate of twenty to forty hertz, as described in the previous figures. Therefore during targeting distance 412 from drill tip 402 normal to hole axis 404 is calculated, and at any time angle 406 does not equal ninety degrees, intersection point 410 and distance 414 from intersection point 410 normal to hole axis 404 is calculated. Referring also to FIG. 18 and FIG. 18a, to indicate to the user when position and alignment of drill bit 2 to hole axis 404 is within predetermined limit, tip indicator 394 is switched to its activated state whenever distance 412 is within a preselected limit, for example one millimeter. Then to indicate that the angular alignment is adequate, alignment indicator 396 is switched to its activated state whenever tip indicator 394 is in its activated state and simultaneously distance 414 is within a preselected limit. Note that the location of plane 408 along hole axis 404 may be selected to be a different point than the origin of hole coordinate system 136, for example plane 408 may be located near the surface of the nail 37 that is closest to drill tip 402. Projecting drill axis 5 to a point near or within hole 38 while also monitoring the distance of drill tip 402 to hole axis 404 creates an interaction between position and orientation limits that ensures that the user does not only have the drill tip 402 within an acceptable distance of hole axis 404, but also has drill bit 2 oriented such that for the current position of drill tip 402, drill bit 2 is oriented to a path that passes within a preselected tolerance zone relative to the center of hole 38. This method has the effect of reducing the allowable angular error as the distance from plane 408 to drill tip 402 is increased.

Figure 19A:
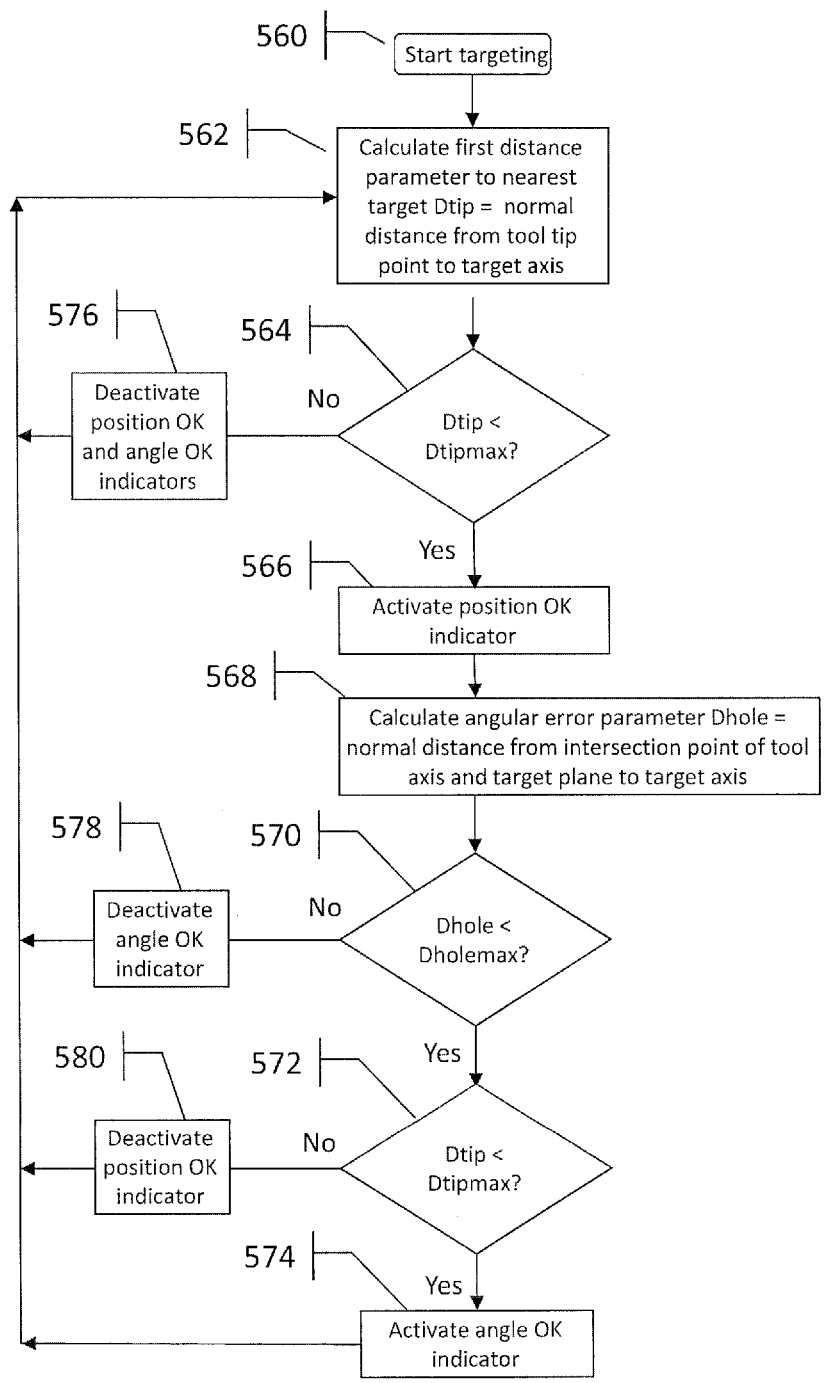
FIG. 19a shows a flowchart of the targeting and user interface method described in FIG. 19.

FIG. 19a shows a flowchart of an example targeting and user interface method described in FIG. 19. Referring also to FIG. 19, at step 560 targeting mode is active which may occur when the targets are defined and the navigation system is tracking the tool relative to the targets. At step 562 a distance parameter $D_{tip}$ is calculated as the normal distance 412 from the drill tip 402 to drill axis 5. At step 564 if distance 412 is less than a selected maximum $D_{tipmax}$, the systems activates a position indicator such as tip indicator 394 at step 566. If the distance parameter is outside of the selected limit, both tip indicator 394 and angle indicator 396 are turned off at step 576, if they are active from a previous measurement sample. At step 568 an angular alignment parameter $D_{hole}$ is calculated as the normal distance 414 from intersection point of drill axis 5 and selected plane 408. At step 570 distance 414 is compared to a threshold $D_{holemax}$ and if distance 414 is greater than $D_{holemax}$ angle indicator 396 is turned off at step 578 if it is still active from a previous measurement sample. If distance 414 is less than $D_{holemax}$ the state of tip indicator 394 is checked at step 572 and if tip indicator 394 is still active, angle indicator 396 is activated, and acceptable alignment is indicated by both tip indicator 394 and angle indicator 396 being simultaneously activated.

Figure 20:
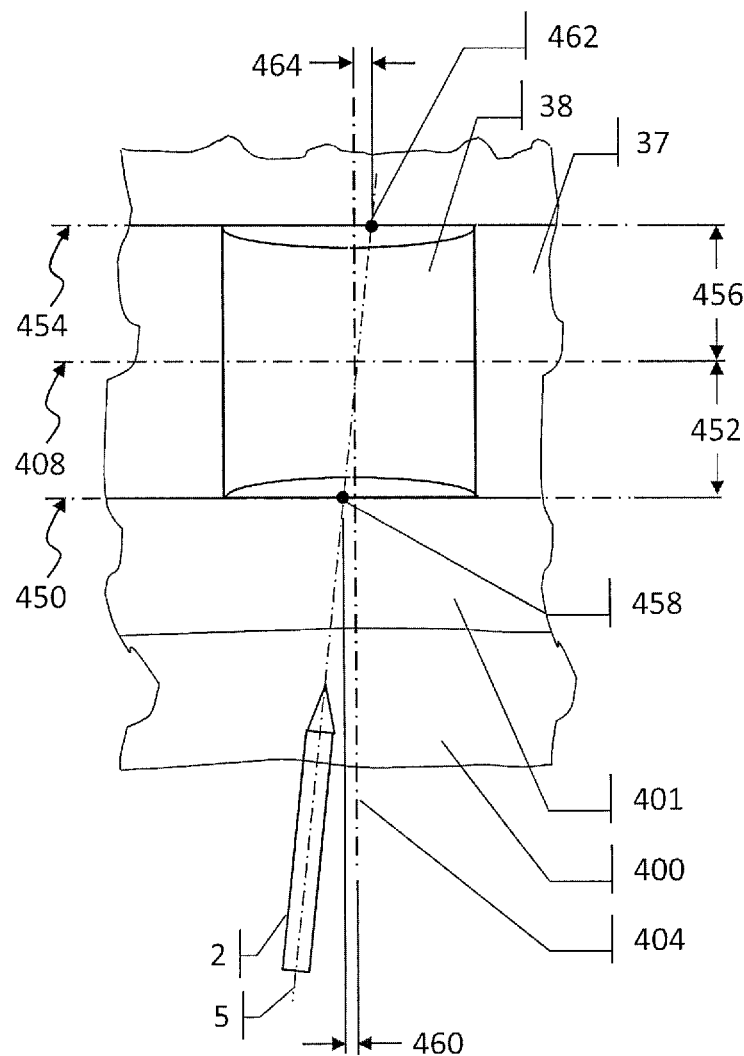
FIG. 20 is similar to FIG. 19 but shows an alternate method of defining the drill alignment limits.

With reference to FIG. 20, in accordance with an alternate embodiment of the invention, a section view through a bone and implant with a drill bit approaching alignment with a locking hole in the implant is shown to illustrate an alternate method of determining when the tool has reached an acceptable alignment with the target according to selected limits. In some applications it may be advantageous to define a segment of the target axis over which the alignment tolerances apply, and to potentially specify different tolerance limits at each end of the segment. For example an allowable angular tolerance for a shaft passing through a hole may be greater for a short hole than a long hole for a given radial clearance between the shaft and the hole. For another example in the case of a countersunk screw it may be desired to specify a tight positional tolerance at the point on the target axis in plane with the countersunk edge of the hole, so that the countersink aligns well, while the positional tolerance at the other end of the hole may be allowed to be larger. One example of this method is described in detail as follows: Nail 37, locking hole 38, skin and soft tissue 400, bone 401, hole axis 404 and plane 408 are shown and are defined in FIG. 14. The alternate targeting method shown differs from the exemplary embodiment described in FIG. 19 in that proximal plane 450 is defined normal to hole axis 404 at a selected distance 452 along hole axis 404 from plane 408, and distal plane 454 is defined normal to hole axis 404 at a selected distance 456 along hole axis 404 from plane 408, and proximal plane 450 is closer to drill bit 2 than distal plane 454. During targeting, the position and orientation of drill axis 5 relative to hole coordinate system 136 (shown in FIG. 7) is monitored constantly as described above. Therefore during targeting at any time that drill axis 5 is not normal to hole axis 404, proximal intersection point 458 between drill axis 5 and proximal plane 450 is defined and proximal distance 460 is calculated as the normal distance from point 458 to axis 404. Similarly distal intersection point 462 between drill axis 5 and distal plane 454 is defined and distal distance 464 is calculated as the normal distance from point 462 to axis 404. Referring also to FIG. 18 and FIG. 18a, to indicate to the user when position and alignment of drill bit 2 to hole axis 404 is within predetermined limit, tip indicator 394 is switched to its activated state whenever proximal distance 460 is within a preselected limit. Then to indicate that the angular alignment is adequate, alignment indicator 396 is switched to its activated state whenever tip indicator 394 is in its activated state and simultaneously distal distance 464 is within a preselected limit. This targeting method ensures that the drilled hole axis lies within a cylindrical or frustrum-shaped tolerance zone about hole axis 404, over only a selected segment of axis 404 as defined by distance 452 and distance 456. For example, for a cylindrical screw shank having a diameter one millimeter less than the diameter of hole 38, the limit for distance 460 and distance 464 may be selected to be less than one-half of a millimeter, and both proximal plane distance 452 and distal plane distance 456 may be selected to be equal to the radius of nail 37, as shown in the figure, thus ensuring that if the screw is installed coaxial with drill axis 5 the screw shank will not foul hole 38 (assuming angles are small). Alternately different limits may be applied to distance 460 and distance 464, for example to accommodate a tapered screw shank while maximizing the tolerance limits.

Figure 20A:
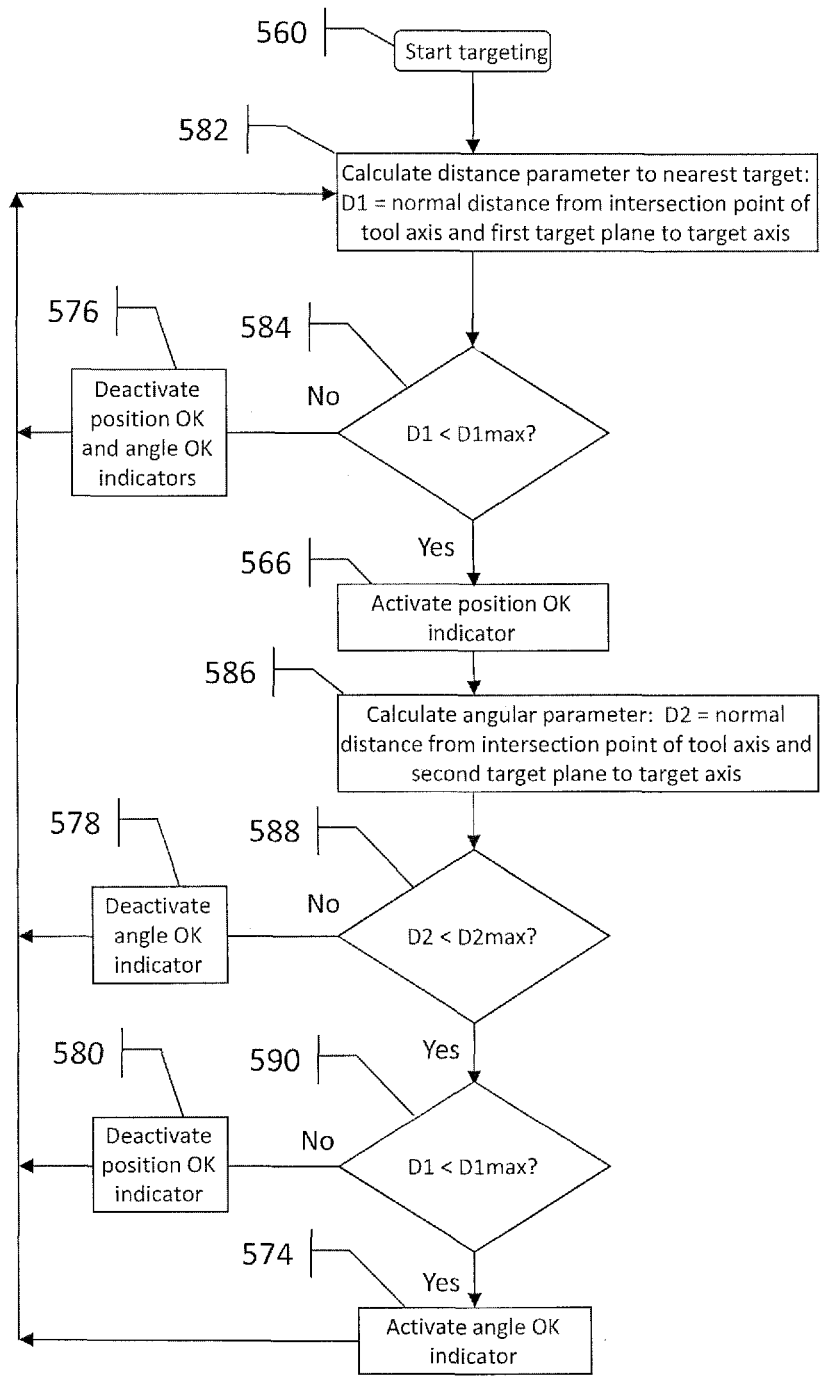
FIG. 20a shows a flowchart of the alternate targeting and user interface method described in FIG. 20.

FIG. 20a shows a flowchart of an example targeting and user interface method described in FIG. 20. Referring also to FIG. 20, at step 560 targeting mode is active which may occur when the targets are defined and the navigation system is tracking the tool relative to the targets. At step 582 a distance parameter D1 is calculated as the normal distance from hole axis 404 to the intersection point of drill axis 5 and a selected proximal plane 450. At step 584 if distance D1 is less than a selected maximum $D1_{max}$, the systems activates a position indicator such as tip indicator 394 at step 566. If the distance parameter D1 is outside of the selected limit, both tip indicator 394 and angle indicator 396 are turned off at step 576, if they are active from a previous measurement sample. At step 586 an angular alignment parameter D2 is calculated as the normal distance from hole axis 404 to the intersection point of drill axis 5 and selected distal plane 454. At step 588 D2 is compared to a threshold $D2_{max}$ and if D2 is greater than $D2_{max}$ angle indicator 396 is turned off at step 578 if it is still active from a previous measurement sample. D2 is within the selected limit $D2_{max}$ the state of tip indicator 394 is checked at step 590 and if tip indicator 394 is still active, angle indicator 396 is activated, and acceptable alignment is indicated by both tip indicator 394 and angle indicator 396 being simultaneously activated.

Another aspect of the invention provides registration apparatus configured to temporarily align a tool and field generator with selected target features, thereby allowing the invention to be used without prior knowledge of the relationship of a sensor to the target features of interest. For example some embodiments do not require a database of target component dimensions and can infer targeting information from registration data.

Target features may be measured directly in a variety of different ways, for example by digitizing the surfaces or edges of the target or by temporarily aligning the tool with the target and recording the ideal targeted position of the tool. Registration measurements may also have selected degrees of freedom, for example in registering a hole to be drilled through, it may be sufficient to measure only the hole centerline and disregard orientation about or location along the centerline, for example if it is only important that the navigated tool aligns with the hole.

In other cases it may be useful to additionally register a point on the centerline (for example to measure tool proximity to the hole) and/or a rotational position about the centerline (for example to be able to infer the location of other features relative to the hole in a single registration measurement).

With particular relevance to electromagnetic navigation systems, registration is advantageously done with all components that may affect navigation measurements present and in place as they will be used during targeting, and in the relative positions that will be most critical during targeting. The registration apparatus may alternately approximate the effects of any components that may be not be present during registration.

In some embodiments the registration apparatus is a registration tool that may be mountable directly to the tool, for example the registration tool may slide over a drill bit portion of the tool, and be made of selected materials that do not affect the navigation system.

In some embodiments the registration apparatus is a registration tool that temporarily replaces part of the tool and approximates the effect of the replaced part on the navigation system. For example the registration tool may replace a drill bit and have similar material, form and mass to the drill bit.

In some embodiments the registration apparatus is a feature or adaptation of the tool. For example the tool may include a shoulder adapted to fit the target feature to be registered and incorporated into the structure of the tool. For another example a drill bit may include a series of shoulders adapted to fit a selected range of target features.

Each feature of a registration apparatus described above may be advantageous individually or in combination with some or all of the other features described. Other embodiments within the scope of the invention may include a subset of the advantageous features described above and in example embodiments.

Figure 21:
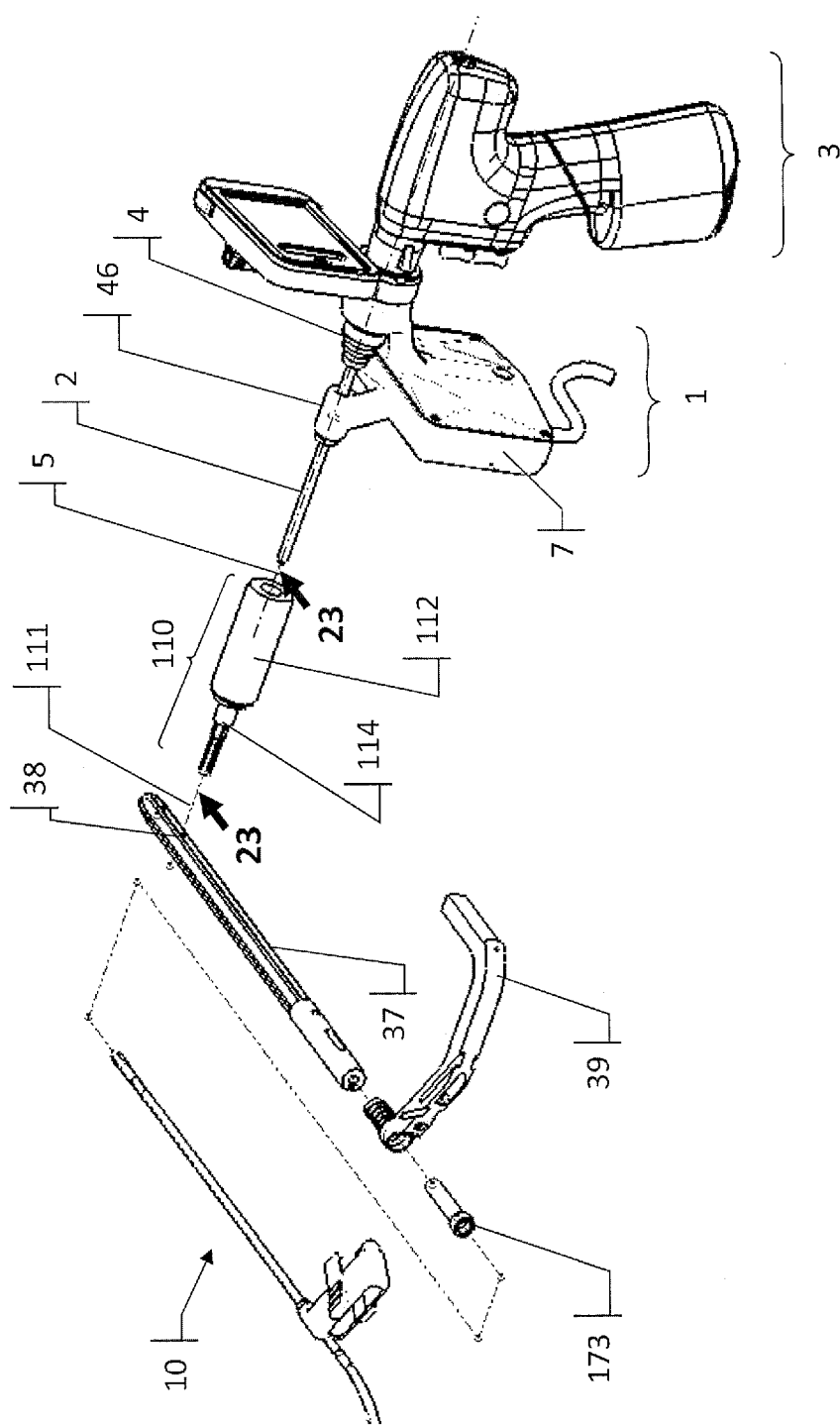
FIG. 21 shows an exploded view of an example field generator component of a navigation system, a drill, a drill bit, an IM nail with a distal locking hole, a sensor inserted in the nail, a registration tool, and a drill bushing integrated with the field generator according to one embodiment of the invention.

With reference to FIG. 21, in accordance with an embodiment of the invention, an exploded view of the apparatus is shown similar to FIG. 7 and additionally illustrates an example of a registration tool included to allow direct measurement of the target holes relative to sensor 10. Navigation unit 1 has bushing 46 and chuck 4, drill bit 2 which rotates about drill axis 5, drill 3 coupled to navigation unit 1, IM nail 37 having distal locking hole 38, sensor 10, cannulated screw 173, and insertion tool 39 are shown, and also including registration tool 110 for temporarily aligning drill axis 5 with hole 38 for the purpose of directly measuring and recording the relative position of sensor tool 10 to hole 38. Registration tool 110 has body portion 112 and tip portion 114 and longitudinal axis 111.

Figure 22:
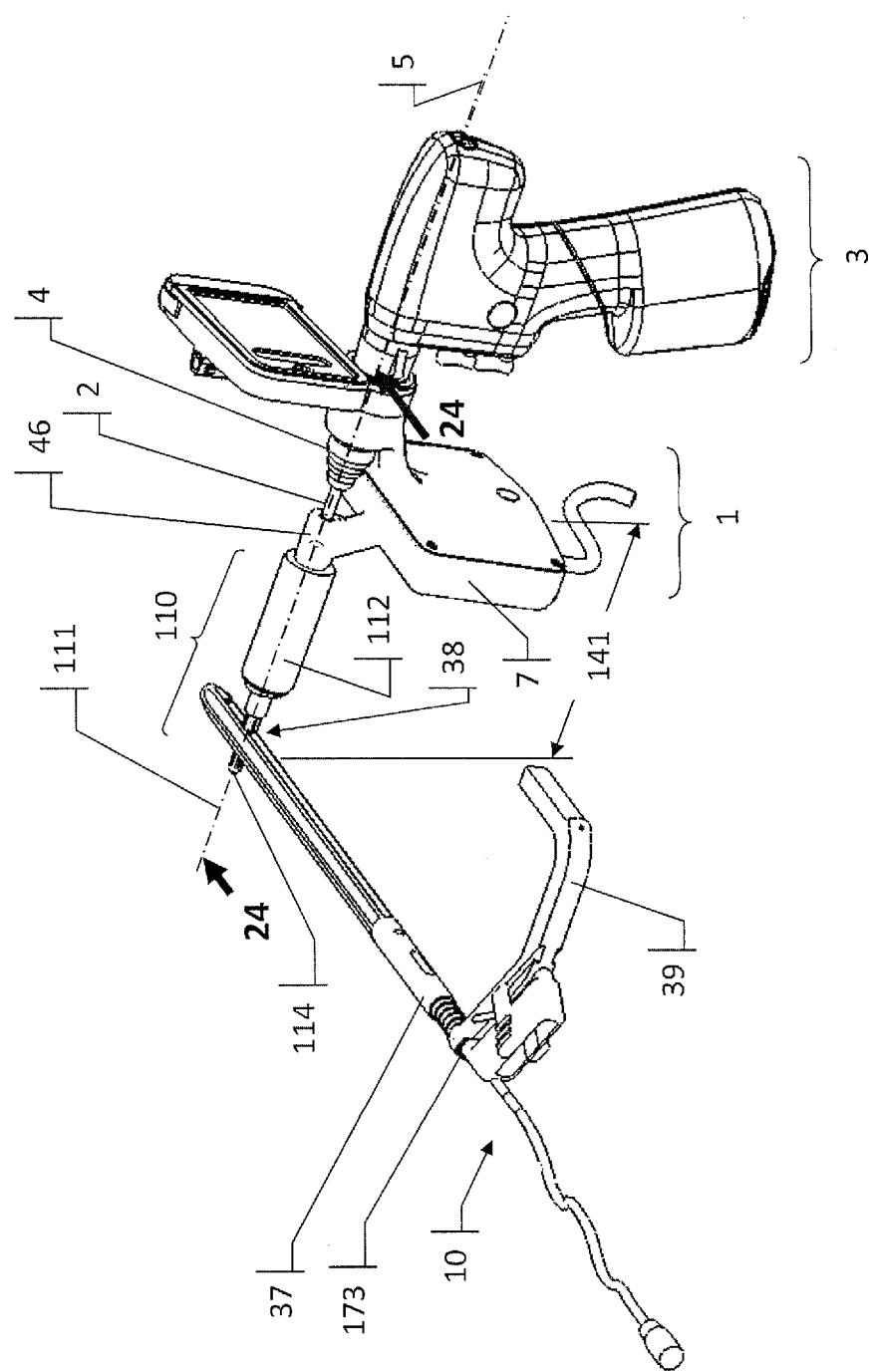
FIG. 22 shows the components of FIG. 21 assembled according to the exemplary embodiment and exemplary application, with the registration tool inserted in the distal locking hole and in position for registering the system to the hole.

With reference to FIG. 22, the components of FIG. 21 are shown assembled with registration tool 110 inserted in the distal locking hole 38 of nail 37, in position for calibrating the system to hole 38. IM nail 37, insertion tool 39, cannulated screw 173 and sensor 10 are assembled (as described above in FIG. 7) such that sensor 10 is held in a fixed, predetermined location relative to a target location on the object being drilled, in this embodiment locking hole 38. Registration tool 110 slides on to drill bit 2 and abuts against drill bushing 46. Body portion 112 of registration tool 110 fits drill bit 2 with a close sliding fit (referring also to FIG. 24), causing the longitudinal axis 111 of registration tool 110 to be coincident with drill axis 5. Tip portion 114 fits locking hole 38 with an interference push fit. Thus when assembled for hole registration as shown, locking hole 38 and drill bit 2 are coaxial and their axes are coincident with drill axis 5 which is fixed relative to navigation unit 1, and sensor 10 is fixed in all degrees of freedom except rotation about drill axis 5 with respect to navigation unit 1. Distance 141 from unit 1 to sensor 10 as defined above in FIG. 7 is shown.

Figure 23:
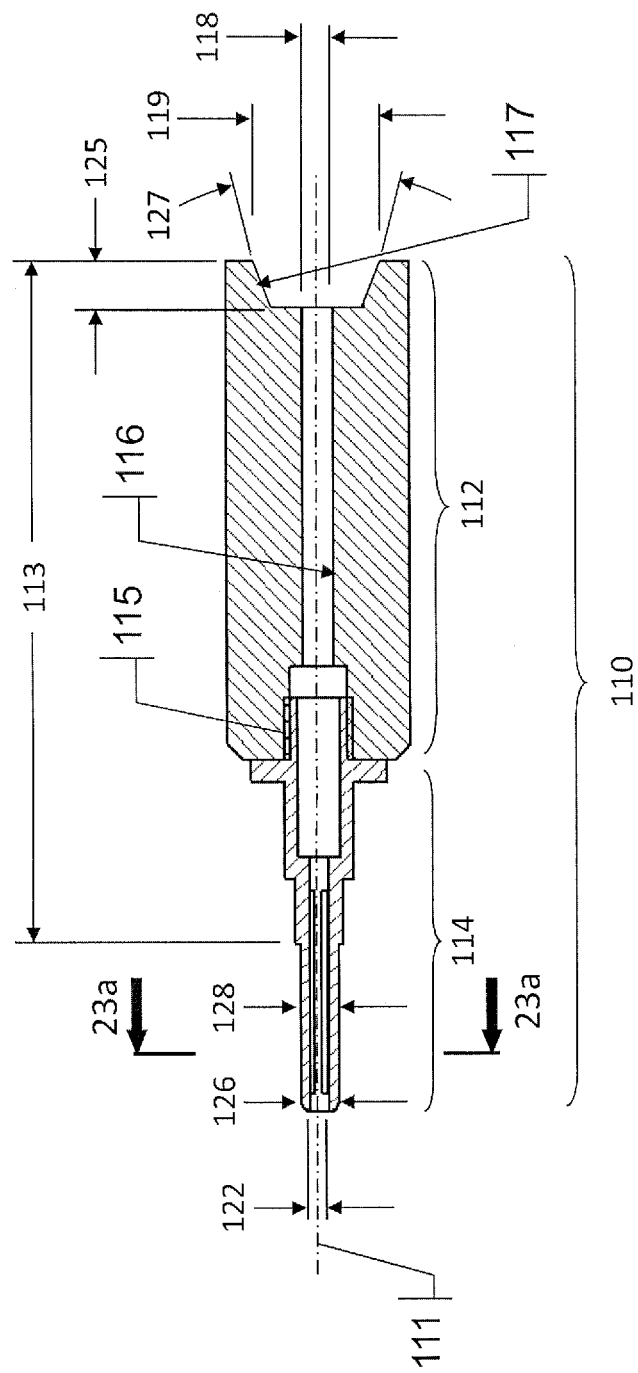
FIG. 23 shows a section through the exemplary registration tool.
Figure 24:
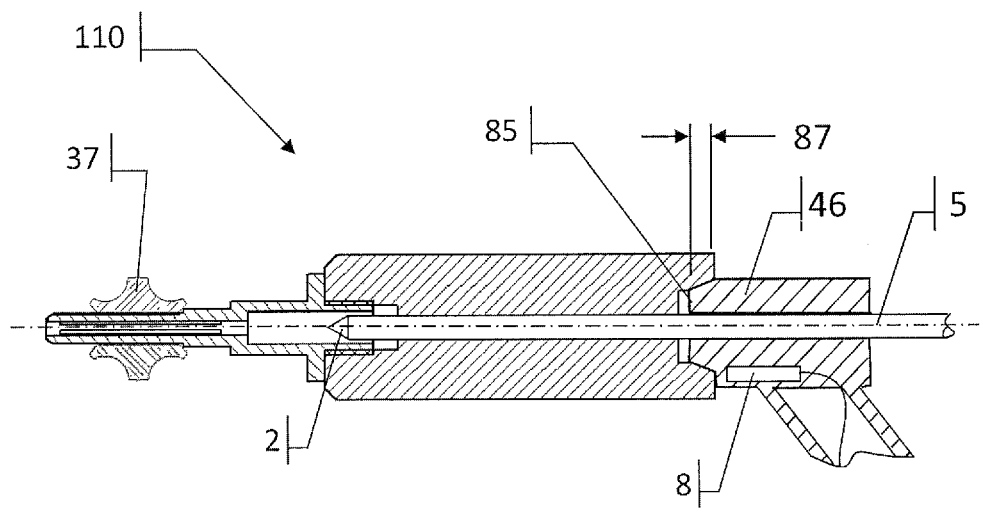
FIG. 24 shows a section through the exemplary registration tool and IM nail when in position for registering the system to the hole.

With reference to FIG. 23, a section through registration tool 110 taken from FIG. 21 is shown. Registration tool 110 comprises body portion 112 and tip portion 114 connected by threads 115 so that tip portion 114 may be replaced with an alternate tip portion having a different diameter or shape. Longitudinal axis 111 is common to tip portion 114 and body portion 112. Body portion 112 has hole 116 along axis 111. Hole 116 has diameter 118 selected to be a close sliding fit over the shank of drill bit 2 (seen in FIG. 21) such that registration tool 110 may be slid on and off drill bit 2 by hand with a friction fit, and bending of drill bit 2 and play between drill bit 2 and registration tool 110 is minimized when registration tool 110 is installed over drill bit 2 as shown in FIG. 24. Also referring to FIG. 24, registration tool 110 has length 113 a selected amount greater than the length of drill bit 2 extending distally from drill bushing 46 so that when assembled for calibrating a locking hole (as shown in FIG. 22), the distal tip of drill bit 2 is positioned in approximately the same position relative to sensor 10 as it will be during surgery as the drill bit 2 enters bone and approaches hole 38. The materials used for registration tool 110 are ideally non-ferromagnetic, and preferably of low electrical conductivity, to minimize effects on the electromagnetic navigation system. Body portion 112 may be made of a rigid material and tip portion 114 may be made of a material with an elastic range and modulus sufficient to provide a suitable push fit in a hole having a selected diameter range. For example body portion 112 may be made of round acetal rod having a one inch outside diameter, and tip portion 114 may be made of 300 series stainless steel. Many other materials may be suitable for both parts, for example titanium, and high modulus sterilizable plastics such as PEEK or Ultem™.

Figure 23A:
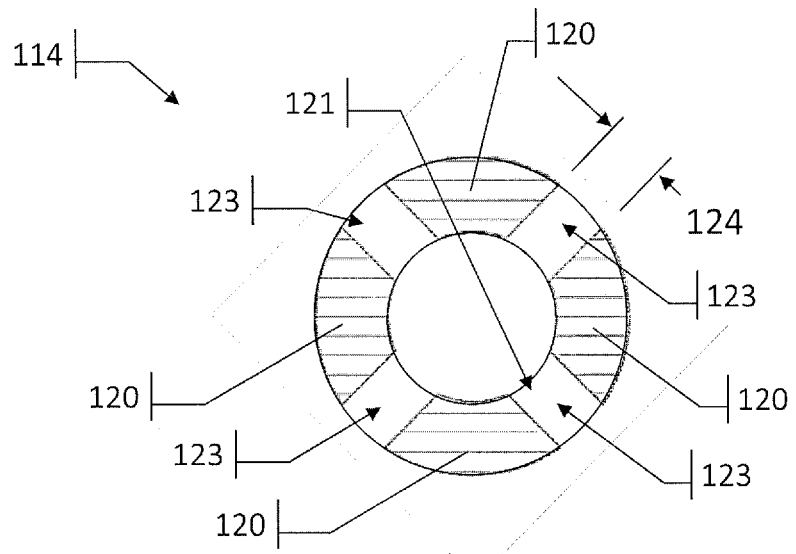
FIG. 23a shows a section through the tip portion of the exemplary registration tool.

With reference to FIG. 23*a*, a section through the tip portion 114 of registration tool 110 is shown. Referring to FIG. 23 and FIG. 23*a* together, tip portion 114 has hole 121 along axis 5, and four slots 123 extending radially outwards from axis 111, thus forming four flexible segments 120 all having the same cross section and shape defined by hole diameter 122 and slot width 124 and all being evenly distributed about axis 111. Hole diameter 122 and slot width 124 are selected along with the material properties of the material selected for tip portion 114 such that flexible segments 120 flex within the elastic range of their material such that free diameter 128 may be compressed down to tip fixed diameter 126 without breaking or permanently deforming. Since flexible segments 120 compress radially inwards evenly when tip portion 114 is in a cylindrical bore having a diameter less than free diameter 128, tip portion 114 is centered within any cylindrical bore within a predetermined diameter range between tip fixed diameter 126 and free diameter 128. Flexible segments 120 are furthermore designed to flex within a subrange of the elastic range of the material such that registration tool 110 may be inserted and removed by hand with a push fit, yet provide resistance to forces tending to make axis 111 non-colinear with the cylindrical axis of hole 38 (seen in FIG. 21). A suitable non-colinearity limit is one degree when subjected to a moment in any plane passing through axis 111 of up to 5 N-m. For example, for a locking hole having a tolerance range of 5.1 millimeters to 5.2 millimeters and a tip portion 114 made of 303 stainless steel, suitable values for hole diameter 122, slot width 124, tip fixed diameter 126, and free diameter 128 are 2.8, 1.0, 4.9 and 5.3 millimeters respectively. One skilled in the art will recognize that the apparatus shown in FIGS. 23 and 23a may be adapted to various shapes such as slotted hole by way of suitable detail design of slots 124 and flexible segments 120.

Referring to FIG. 24, a section through registration tool 110 taken from FIG. 22 is shown, with registration tool 110 installed. Referring also to FIG. 23, longitudinal axis 111 and is coincident with drill axis 5 when registration tool 110 is installed over drill bit 2. Countersink 117 has diameter 119, depth 125, and angle 127 selected to fit over boss 85 of drill bushing 46, boss 85 having length 87 and sharing diameter 119 and angle 127 with countersink 117. Length 87 is less than depth 125. Boss 85 and countersink 117 thereby together provide a positive stop defining the position of registration tool 110 along axis 5 and coaxiality of axis 111 to axis 5.

Figure 24A:
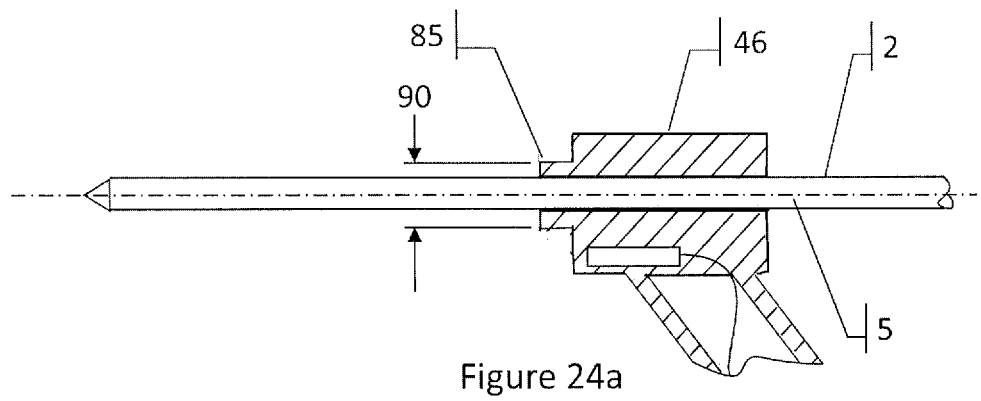
FIG. 24a shows a section through a first additional example embodiment of a registration apparatus.

Referring to FIG. 24a, a section through a first additional example embodiment of a registration apparatus is shown similar to FIG. 24, but wherein registration tool 110 is not used and instead bushing 46 includes boss 85 adapted as shown with diameter 90 chosen to fit the target feature. Drill bit 2 and drill axis 5 are also shown.

Figure 24B:
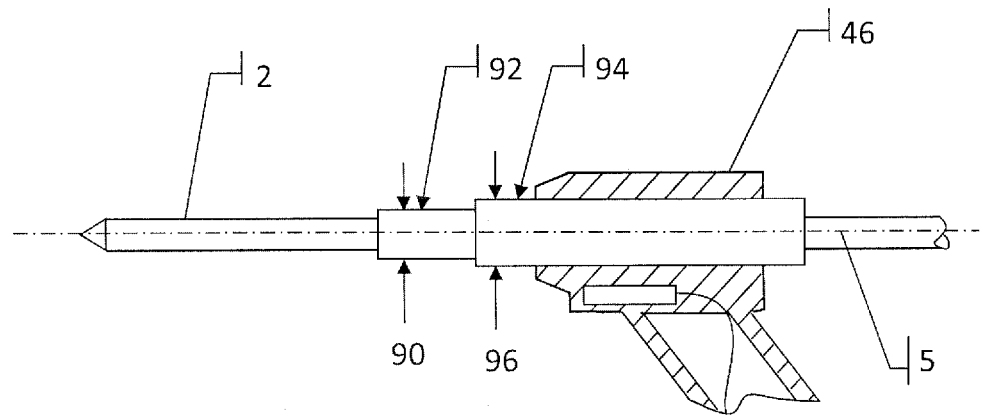
FIG. 24b shows a section through a second additional example embodiment of a registration apparatus.

Referring to FIG. 24b, a section through a second additional example embodiment of a registration apparatus is shown, similar to FIG. 24, but wherein registration tool 110 is not used and instead drill bit 2 has shoulder portions 92 and 94 adapted to fit target features having diameters 90 and 96. Bushing 46 and drill axis 5 are also shown.

Figure 24C:
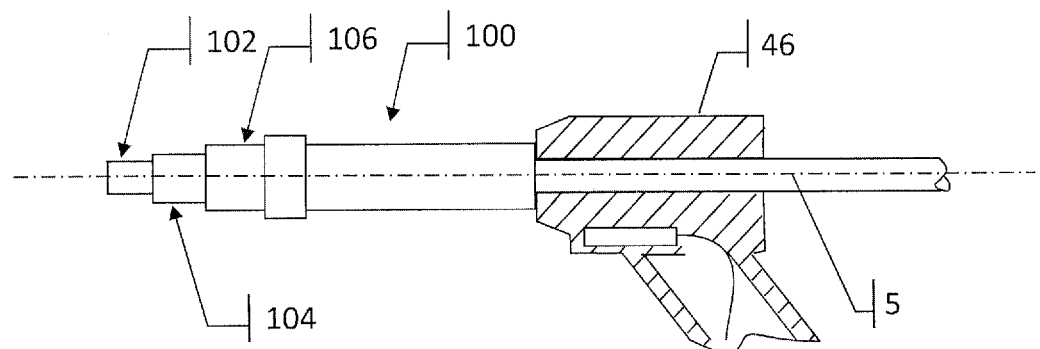
FIG. 24c shows a section through a third additional example embodiment of a registration apparatus.

Referring to FIG. 24c, a section through a third additional example embodiment of a registration apparatus is shown similar to FIG. 24, but wherein registration tool 110 is not used and instead drill bit 2 is removed and replaced with registration tool 100 having a series of shoulders 102, 104, and 106 having diameters selected to fit three different target features. In this embodiment the design and material of registration tool 100 are selected to have similar effect on electromagnetic position tracking as drill bit 2. Referring also to FIG. 22, in this embodiment the diameter of the target feature may be determined from among the three possible diameters by recording the distance 141 along drill axis 5 from navigation unit 1 to a sensor fixed relative to the target feature.

Figure 24D:
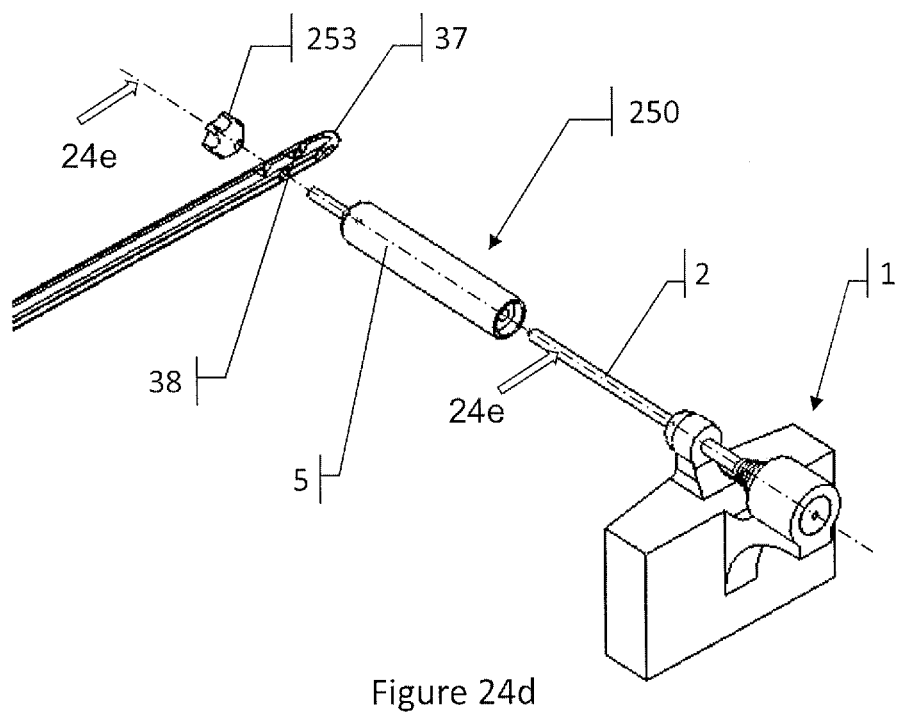
FIG. 24d shows an exploded view of a fourth additional example embodiment of a registration apparatus.
Figure 24E:
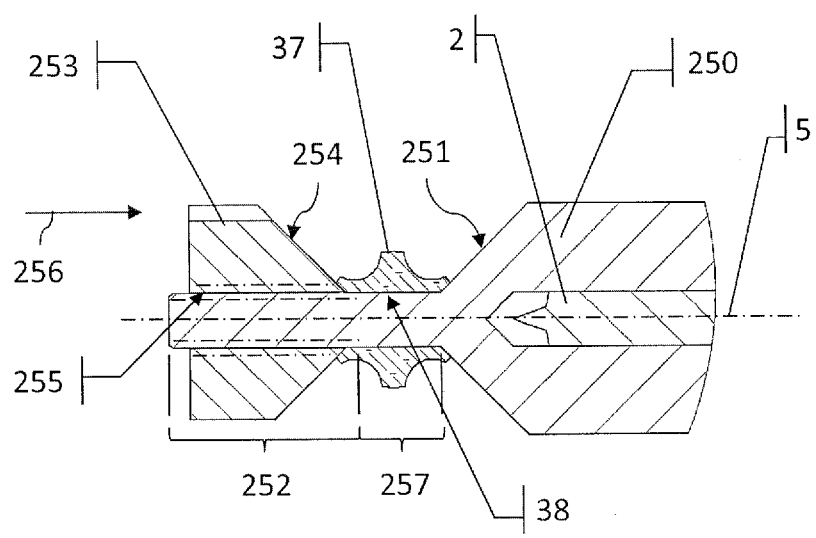
FIG. 24e shows a section through the fourth additional example embodiment of a registration apparatus.

Referring to FIG. 24d and FIG. 24e, a fourth additional example embodiment of a registration apparatus is shown which is suitable for a target hole having a revolved section portion that makes a complete revolution about the hole axis at each end of the hole, for example a sharp edge, or a chamfered edge of a minimum depth. This embodiment has the advantage of being adaptable to a wider range of target hole diameters than the previous examples. In the example embodiment shown in FIG. 24d and FIG. 24e, locking hole 38 has a ninety degree countersink having a minimum depth at both ends of the hole. Locking registration tool 250 slides over drill bit 2 and further includes conical surface 251, threaded portion 252 and cylindrical portion 257, and lock nut 253 has conical surface 254 and threaded hole 255. In use registration tool 250 is passed through the hole 38 and lock nut 253 is threaded on to registration tool 250 and tightened to create a seating force along direction 256 which compresses conical surfaces 251 and 254 against the countersunk edges of hole 38, thereby making axis 5 coaxial with hole 38. In this embodiment cylindrical portion 257 of registration tool 250 need only be smaller than the diameter of hole 38 and therefore locking registration tool 250 may be used with a range of hole diameters, and the user does not have to operate an interference fit as described in some other example embodiments. One skilled in the art will recognize that a variety of mechanical arrangements may be used in place of the threaded connection between lock nut 253 and registration tool 250; any mechanism which can maintain conical surfaces 251 and 254 coaxial and apply a seating force acting to compress conical surfaces 251 and 254 towards each other along common axis 5 may be used.

Figure 24F:
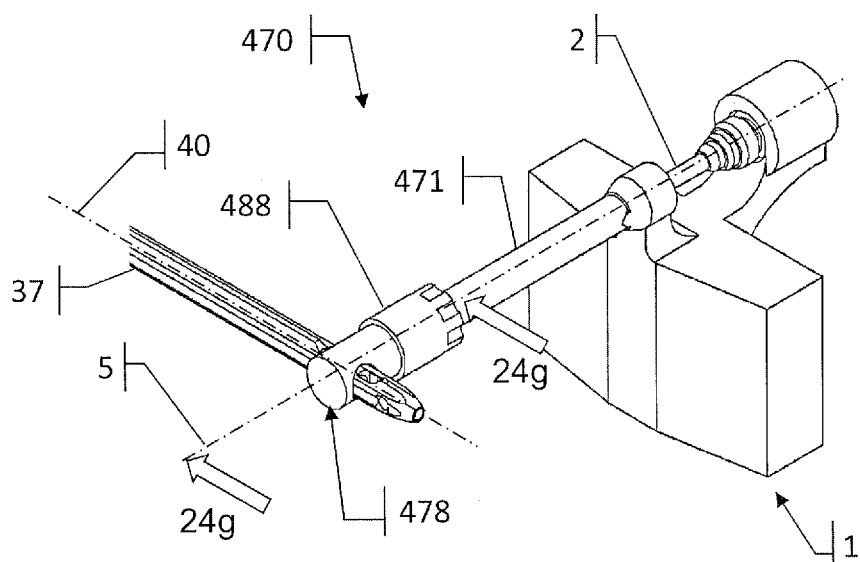
FIG. 24f shows a section through a fifth additional example embodiment of a registration apparatus, in which an additional degree of freedom is controlled.
Figure 24G:
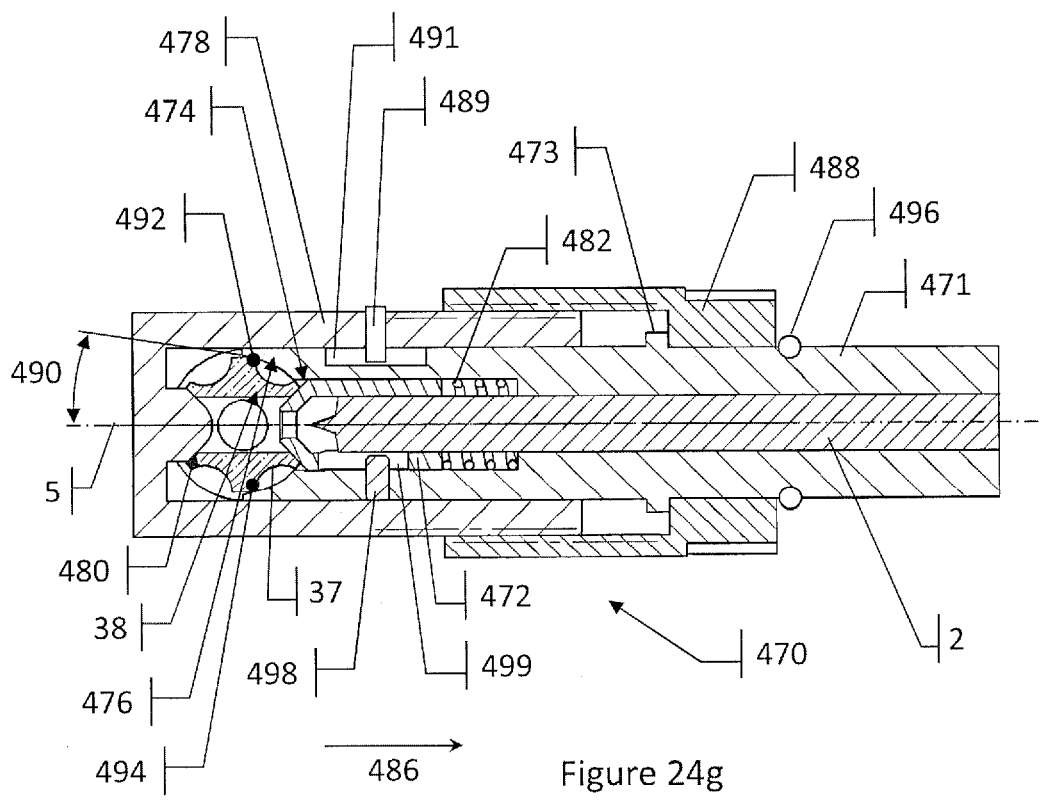
FIG. 24g shows another view of the fifth example embodiment of a registration apparatus of FIG. 24f.
Figure 24H:
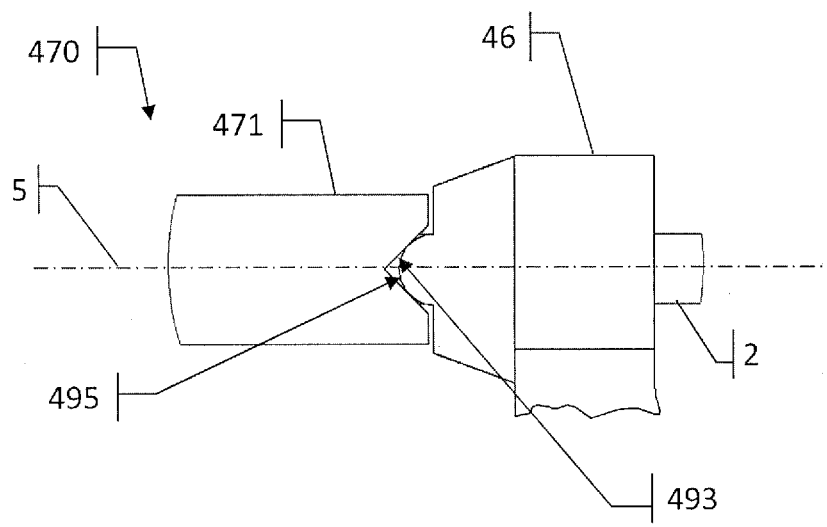
FIG. 24h shows another view of the fifth example embodiment of a registration apparatus of FIG. 24f.

Referring to FIG. 24f, FIG. 24g and FIG. 24h, a fifth additional example embodiment of a registration apparatus is shown, in which an additional degree of freedom is controlled. In addition to temporarily fixing drill axis 5 coaxial with hole 38 as in the previously described embodiments, registration tool 470 can additionally fix the rotational position of navigation unit 1 relative to nail 37 about axis 5, thereby providing the definition of a plane through nail longitudinal centerline 40 and the axis of hole 38 relative to sensor coordinate system 134 (seen in FIG. 7) as additional registration information. This additional constraint may be achieved in a variety of ways depending on the specific form of nail 37 and hole 38, for example referring also to FIG. 1a, if every nail 37 in a set of IM nails 164 has some common geometric element, the example registration tools described above may easily be adapted to constrain the nail in rotation about axis 5. For example if the common geometric element is at least two holes in group 189, the registration tool could have a variety of structural elements added to engage the second hole and also be adapted as shown in FIG. 24h to have a fixed rotational position relative to navigation unit 1. In the example embodiment shown, nail 37 has a constant cross section with a cylindrical outer envelope within a selected diameter range in the area of hole 38. The centerline of hole 38 is perpendicular to and passes through nail centerline 40, and hole 38 has a countersink at each end. Registration tool 470 includes body portion 471 having multi-faceted surface 476. Threaded collar 488 engages clamp portion 478 and bears on shoulder 473 such that when tightened, clamp portion 478 is drawn towards surface 476 in direction 486 and creates a seating force holding nail 37 against surface 476. Surface 476 has at least two planar facets at angle 490 symmetrical about a plane through axis 5 and nail centerline 40, therefore when nail 37 is seated against surface 476 by a seating force in direction 486, nail 37 is held in line contact with surface 476 at two lines, both parallel to nail centerline 40 and passing through contact points 492 and 494, thereby constraining nail 37 in rotation about axis 5 relative to registration tool 470. Clamp portion 478 has conical surface 480 having an axis of revolution coincident with axis 5 and engaging hole 38, therefore when nail 37 is compressed between surface 476 and surface 480 by a seating force in direction 486, hole 38 is constrained to be coaxial with axis 5. Plunger 472 has conical surface 474 having an axis of revolution coincident with axis 5 and spring 482 pushes plunger 472 against nail 37, thereby constraining rotation of nail 37 about centerline 40. Plunger 472 is stopped from sliding out of body portion 471 by set screw 498 which engages slot 499 in plunger 472. Clamp portion 478 is stopped from sliding off of and rotating relative to body portion 471 by set screw 489 which engages slot 491 in body portion 471. Threaded collar 488 is held from sliding off body portion 471 by snap ring 496. As long as at least one of the line contacts passing through point 492 and point 494 can be maintained and conical surfaces 474 and 480 remain seated in the edges of hole 38, nail 37 is constrained in all six degrees of freedom relative to body portion 471. One skilled in the art will recognize that there may be other mechanical arrangements that may be used to apply the constraints described above, and that various adaptations may be made to accommodate variations in the shape of nail 37 and hole 38, for example for non-cylindrical cross sections of nail 37, surface 476 may be modified to have asymmetrical facets, non-planar facets, or a specific form to match the nail. Similarly surface 476 may be replaced with a variety of mechanical clamping arrangements. Referring to FIG. 24*h*, body portion 471 has vee-shaped groove 493, and bushing 46 is adapted to include convex boss 495. Groove 493 engages boss 495 and constrains rotation of registration tool body portion 471 about axis 5 relative to unit 1 when the user inserts unit 1 and drill bit 2 into registration tool 470.

Referring to the exemplary registration tools described above, one ordinarily skilled in the art will recognize that the target feature to be registered may be of other forms such as a recess, slot, conical hole, or non-cylindrical hole, with corresponding adaptation of the registration tool shape, and that a variety of mechanical arrangements may be used to temporarily align the registration tool to the feature such as clamping, bolting, using an expanding shaft or collet, and the like.

Figure 25:
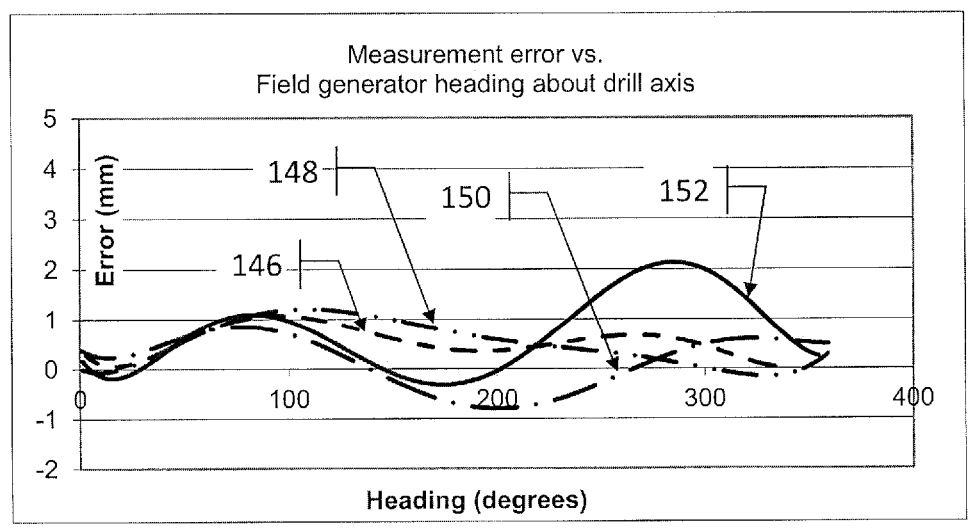
FIG. 25 shows an example plot of typical measurement error versus field generator position about the drill axis at various distances from the field generator, with the field generator mounted to a typical drill.

With reference to FIG. 25, a plot is shown of typical measurement error versus field generator heading 139 (referring also to FIG. 7 and FIG. 7*a*) about drill axis 5 at selected distances 141, with navigation unit 1 and drill bit 2 mounted to a typical drill 3. When ferromagnetic and/or conductive metals are within or near the measurement volume of the navigation system, the magnetic fields generated by the navigation system may be distorted, causing the measurements to become inaccurate. These effects may be exaggerated with field generators such as field generator 7 which are small and light enough to be directly mounting on a handheld tool; smaller, lighter field generators generally have smaller drive coils and generate weaker magnetic fields. Large masses of ferromagnetic and/or conductive materials, such as those found in a typical electric drill such as drill 3, can distort measurements even if they are placed near, but not necessarily within, the measurement volume of the navigation system. For example placing a steel plate of sufficient mass behind unit 1 will distort the measurement field enough to cause large errors throughout the measurement volume in front of unit 1. We have observed that when drill 3 is positioned close behind field generator 7 included in unit 1, measurement errors become larger as the measured sensor is brought closer to unit 1, as illustrated in FIG. 25. Therefore to integrate tools such as drill 3 and ferromagnetic drill bit 2 with field generator 7 and maintain sufficiently accurate navigation for the application, detection of and compensation for magnetic field distortion due to the presence of tools is advantageous. In FIG. 25 the horizontal axis of the plot is heading 139. The vertical axis of the plot shows the deviation in millimeters of the origin of sensor coordinate system 134 from nominal circle 142 as field generator 7 is rotated about drill axis 5. Curve 146 shows errors when nominal circle 142 described by sensor 10 lies in a plane intersecting the Zw axis of field generator coordinate system 130 at a distance 141 of one hundred and thirty millimeters. Similarly curves 148, 150, and 152 are generated at values of distance 141 of one hundred and ten, one hundred, and eighty millimeters respectively. FIG. 25 illustrates that measurement error varies with heading 139 of field generator 7 about drill axis 5 when drill axis 5 is aligned with the axis of hole 38, and measurement error increases as sensor 10 is brought closer to field generator 7 and drill 3.

Another aspect of the invention provides a registration method for measuring a target feature position relative to a sensor. In one embodiment, the method comprises the steps of temporarily fixing a tool and field generator assembly to the target feature of the target component at a known position in selected degrees of freedom, recording the position of the sensor relative to the field generator, calculating the relative position of the feature to the sensor, and storing the relative position of the feature to the sensor into the memory of the navigation system. For example in an embodiment the target feature may be a hole, the tool and field generator may be a drill, the drill axis and the hole axis may be held coaxial during registration, and the hole may be defined as a target axis expressed in the coordinate system of the sensor and representing a target axis which is calculated from an average of a selected number of position measurements.

The method may additionally comprise a step producing a lookup table of hole locations at a number of different locations of the sensor relative to the tool and field generator assembly. For example in another embodiment the registration measurement may be made as described above, with registration data being recorded as the user rotates the tool and field generator assembly about the common tool and hole axis. Target location relative to the sensor may then be stored for a selection of different rotational positions, and the appropriate location recalled during targeting when the tool and field generator assembly is at a similar position. In another embodiment the lookup table of target positions may be interpolated and/or a continuous function of target position versus field generator position may be created.

Each feature of a registration method described above may be advantageous individually or in combination with some or all of the other features described. Other embodiments within the scope of the invention may include a subset of the advantageous features described above and in example embodiments.

Figure 26:
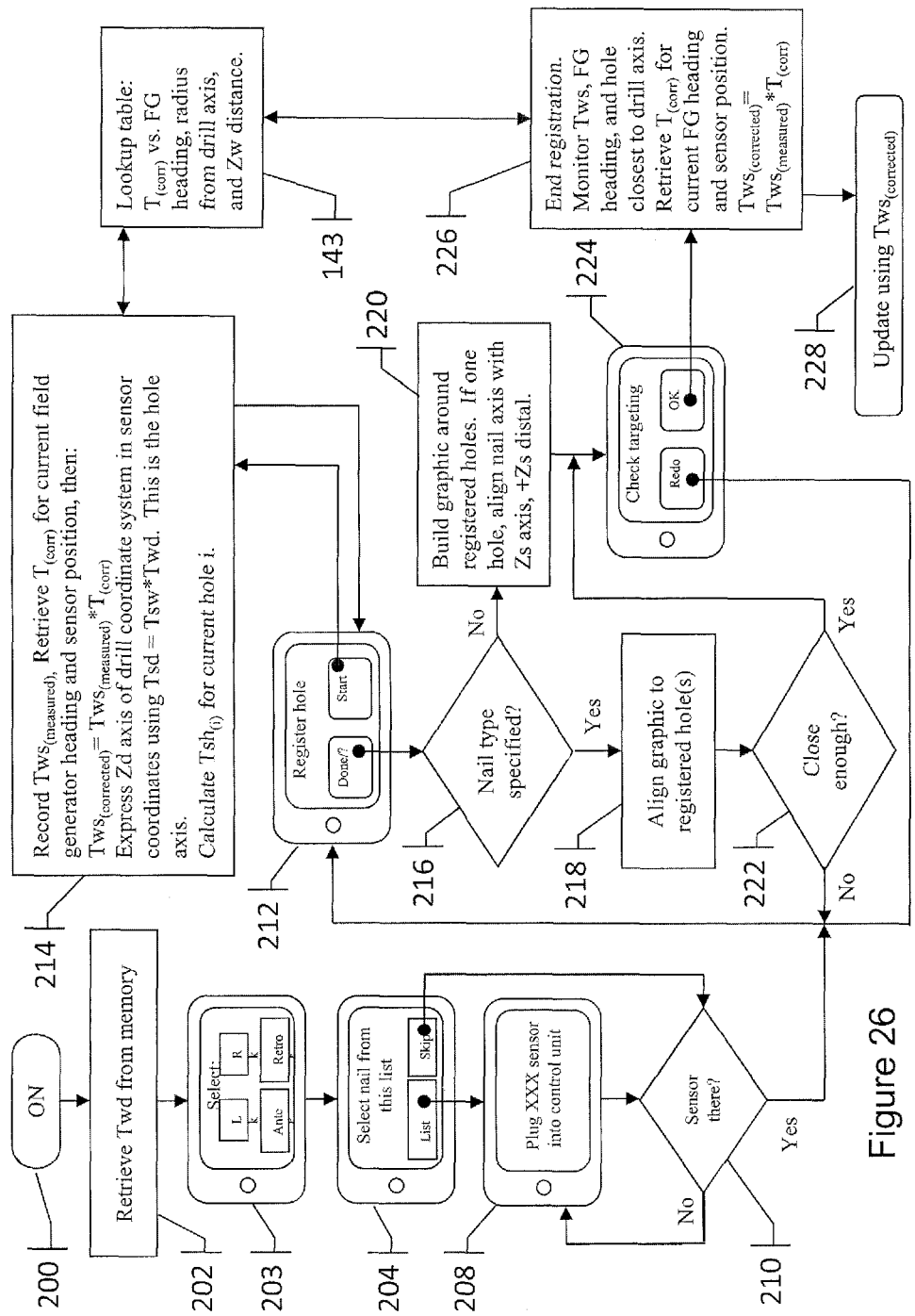
FIG. 26 shows an example flowchart of the registration and operation steps of the system according to one embodiment of the invention.

With reference to FIG. 26, in accordance with an exemplary embodiment of the invention, a flowchart of the method of intraoperative registration and operation of the navigation system is shown, in which factory calibration has been performed and lookup table 143 is stored in system memory. The exemplary method illustrated generally includes the steps of registering the target features and determining the current measured location of a sensor and applying a predetermined correction to the measured location to estimate a more accurate location. The method may also advantageously include defining a subset of critical sensor locations and determining corrective maps or functions for these locations only.

Referring also to FIG. 7a and FIG. 22, measurement errors as shown in FIG. 25 which are a function of radius 144, heading 139, and distance 141 are measured at manufacture and lookup table 143 of correction values is stored in a memory device embedded in field generator 7. Lookup table 143 includes corrections to translations and rotations in the transform Tws from field generator coordinate system 130 to sensor coordinate system 134 which is measured by the navigation system during targeting. For example, navigation unit 1 with drill bit 2 is attached to drill 3 and mounted in a coordinate measuring machine, which may be programmed to move a nail 37 and sensor 10 through a series of nominal circles 142 (having known accuracy and precision limits), in planes normal to the Zw axis of field generator coordinate system 130 and having a range of radii 144, a range of distances 141, and a number of headings 139. A suitable range of radii 144 is ten to ninety millimeters in increments of twenty millimeters, a suitable range of distances 141 is eighty to one hundred and forty millimeters in increments of twenty millimeters, and a suitable number of headings 139 is thirty six, evenly distributed into increments of ten degrees. Thus lookup table 143 is generated from seven hundred and twenty pair of nominal $Tws_{(nom)}$ and measured ($Tws_{(measured)}$) transforms, and contains seven hundred and twenty corrective transforms $Tws_{corr}$, such that for each set of parameters i of radius 144, heading 139, and distance 141:

$$Tws_{(nom)(i)}=Tws_{(measured)(i)}*T_{(corr)(i)}$$

To begin the registration procedure, the system is assembled as shown in FIG. 22 including drill bit 2 installed into navigation unit 1 and registration tool 110 is slid over drill bit 2 and pushed proximally until it abuts bushing 46, and the selected nail 37 is assembled to insertion tool 39 by tightening cannulated screw 22. In step 200 the user powers on the system and in step 202 the transform Twd from field generator coordinate system 130 to drill coordinate system 132 (see FIG. 7) is retrieved from the system memory. In step 203 the user selects right limb or left limb, and antegrade or retrograde approach, so that the correct image orientation may be determined. In step 204 the user inputs either the selected nail being used by selecting it from a preprogrammed list, or a skip command to bypass the specific nail selection and use a generic nail graphic. If the user selects a nail from the list in step 204, the system proceeds to step 208 in which the user is advised of the best length sensor tool 10 to use. In certain cases there may additionally be alternate sensor tool lengths recommended for use with the selected nail and indicated in step 208. Sensors may additionally be colour coded and step 208 may have colour and graphic advisory messages in addition to or in place of text. Step 208 also begins a sensor detection routine 210 in which the navigation system checks to determine if a sensor is plugged in. If the system does not detect a sensor, the process returns to step 208 and cycles through step 208 and step 210 constantly until a sensor is detected.

When a suitable sensor is detected, the system proceeds to step 212 which prompts the user to begin calibrating locking holes. In the exemplary embodiment the criterion for a suitable sensor is a functioning sensor returning complete position and orientation data. In another embodiment sensor tool 10 has sensor identification information stored in a memory device which is read by the navigation system, and the system proceeds to step 212 only if the sensor is one of the recommended types displayed in step 208. Referring back to step 204, if the user elected to skip the specification of the particular nail being used then the system bypasses step 208 advising the user of which sensor to use and proceeds directly to step 210.

In step 212 the user selects 'Start Registration' when the system is assembled as shown in FIG. 22, which starts the locking hole axis measurement process of step 214. In step 214 (referring also to FIG. 7 and FIG. 7a), locking hole coordinate system 136 is defined relative to sensor coordinate frame 134 by calculating the constant transform Tsh for the current locking hole as follows, with drill axis 5 is held coincident with the axis of locking hole 38. Field generator to sensor transform $Tws_{(measured)}$ is recorded from the navigation system, and heading 139, distance 141, and radius 144 are calculated. $Tws_{(measured)}$ is then corrected to $Tws_{(corrected)}$ using lookup table 143 by retrieving the corrective transform $T_{(corr)}$ corresponding to heading 139, radius 144 and distance 141 at the current position:

$$Tws_{(corrected)}=Tws_{(measured)}*T_{(corr)}$$

Then Tsw, the inverse of $Tws_{(corrected)}$, is calculated. The transform Tsd from sensor coordinate frame 134 to drill coordinate system 132 is then calculated as:

$$Tsd=Tsw*Twd,$$

where Twd is the constant field generator to drill transform retrieved in step 206. The Zd axis of drill coordinate system 132, which is collinear with drill axis 5, can then be expressed as a line in the coordinates of sensor coordinate frame 134 using the transform Tsd. Locking hole coordinate system 136 for the current locking hole may then be defined relative to sensor coordinate frame 134 as described above in the detailed description of FIG. 7 and expressed as the transform Tsh. Accuracy is increased by recording a number of samples of $Tws_{(corrected)}$, calculating Tsh for each sample, and averaging the resulting group of transforms Tsh. A suitable number of samples of $Tws_{(corrected)}$ is thirty. The resulting transform Tsh(i) is stored as a constant for the current hole i.

After registration of a hole the system returns to step 212 and when at least one hole has been calibrated the user may select 'Done' to advance the system to step 216 in which it is determined if the user selected a specific nail being used in step 204, or elected to skip nail selection. If a specific nail type was selected in step 204, the system advances to step 218 and retrieves the graphic model of the selected nail from memory. If only one locking hole was calibrated at step 212, the graphic model of the specified nail is aligned with the calibrated hole and rotated about the hole axis such that the nail longitudinal centerline 40 (seen in FIG. 7) is coincident with the projection of the sensor Zs axis onto the plane through the Yh and Zh axes, with the distal tip of the nail at a positive Zs value. If the specified nail graphic model has more than one locking hole, the hole that was calibrated is determined by comparing the distance along Zs from the origin of sensor coordinate frame 134 to the origin of hole coordinate system 136 (seen in FIG. 7) to the expected values for the specified nail and the recommended sensor tool lengths of step 208. If more than one locking hole was calibrated at step 212 the system fits the graphic model to the calibrated hole axes such that the mismatch between the calibrated hole axes and the graphic model hole axes is minimized, and the maximum mismatch among the calibrated holes is reported as two mismatch parameters:

Angular difference between a calibrated hole axis and the corresponding graphic model hole axis, and Distance between the intersection points of a calibrated hole axis and the corresponding graphic model hole axis with a plane passing through the longitudinal centerline of the graphic model of the nail.

One skilled in the art will recognize that other fitting algorithms such as least-squares or other methods to fit selected points or vectors in locking hole frames to graphic model frames may alternately be used.

The system proceeds to step 222 to determine if the calibrated holes match the nominal hole positions in the graphic model for the selected nail. If the mismatch parameters are greater than the predetermined limits the system returns the user to step 212 to recalibrate the holes. If all calibrated hole axes are coincident with the corresponding nominal axes in the graphic model within predetermined limits of the mismatch parameters, the system proceeds to step 224 to draw the targeting view and prompt the user to check registration by confirming that the target graphic shows good alignment with the correct holes. If the user accepts the registration the system proceeds to step 226 in which the navigation system changes from registration to targeting mode and begins constantly reading Tws. If the registration is not correct, the user rejects the registration and returns to step 212. If the user has selected the wrong nail setup in step 203 or nail type in step 204, they may power the system off and on again to return to step 203.

Referring back to step 216, if the user had elected not to select a specific nail in step 204 then the system proceeds to step 220 in which a generic nail graphic model is drawn showing the calibrated holes at their as-calibrated positions, a typical nail shape around these holes having a distal tip at a typical +Zs location. In step 220 if a single hole was calibrated, the graphic is aligned such that the longitudinal axis of the generic nail graphic model is coincident with the projection of the sensor Zs axis onto the plane through the Yh and Zh axes, with the distal tip of the nail at a positive value along the Zs axis of sensor coordinate system 134 (seen in FIG. 7). If two or more holes were calibrated, the longitudinal axis of the generic nail graphic model is aligned with the least squares best fit line to the group of Zh axes of the hole coordinate systems 136 of all the calibrated holes (seen in FIG. 7). The system may then proceed to step 224 and registration can be confirmed as described above.

In step 226 the set of parameters of the current sensor position, heading 139, radius 144, and distance 141, is calculated and the corresponding correction transform $T_{(corr)}$ is retrieved from lookup table 143. A corrected value of Tws for the current reading is calculated by:

$$Tws_{(corrected)} = Tws_{(measured)} * T_{(corr)}$$

and the system proceeds to step 228 to update the targeting display for final alignment using the corrected value.

Figure 26A:
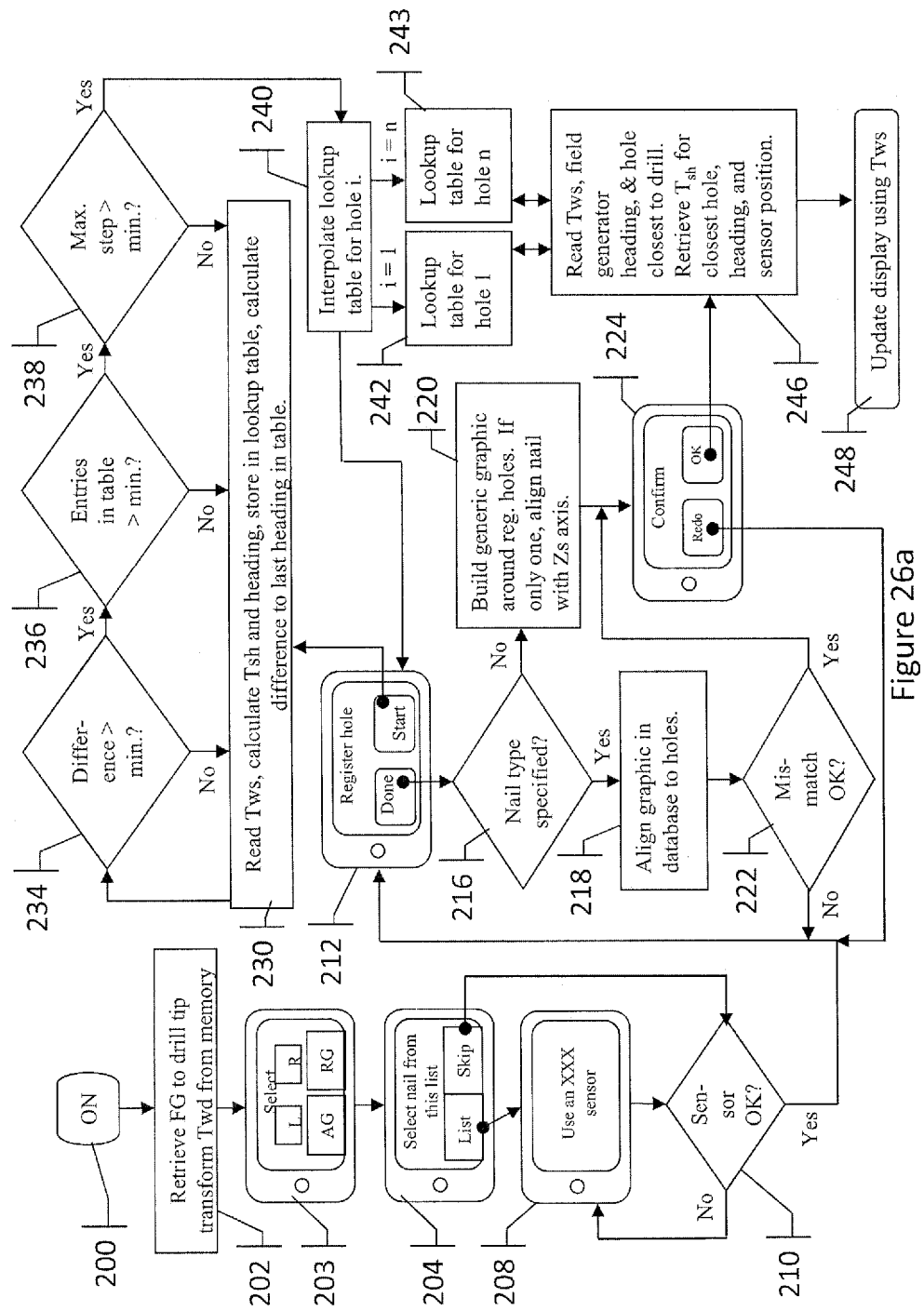
FIG. 26a shows a flowchart of intraoperative calibration of a navigation system which also generates a lookup table of correction values, according to an alternate embodiment of the invention.

With reference to FIG. 26a, in accordance with an alternate embodiment of the invention, a flowchart of an alternate method of intraoperative calibration of the navigation system which generates a lookup table of correction values and registers a target feature intraoperatively is shown. The alternate method illustrated generally includes the steps of registering a target feature, recording a correction map for a subset of critical sensor locations, determining correction functions, determining the current measured location of a sensor, and applying a correction if available for the measured location to estimate a more accurate location. Referring also to FIG. 7, FIG. 7a, and FIG. 22, the alternate method is identical to that shown in FIG. 26 except that step 214 of FIG. 26 is replaced by alternate hole axis measurement steps 230, 234, 236, 238, and 240, and the resulting lookup tables 242 and 243 are used in step 246 to compensate for measurement distortions related to the position of field generator 7 about drill axis 5 during targeting.

In contrast to recording transform Tws with navigation unit 1 a randomly selected heading 139 about drill axis 5 as described in step 214 of FIG. 26, the user is instead prompted to begin rotating navigation unit 1 about drill axis 5 through a range of headings 139 in either the positive direction 140 or the negative direction opposite to direction 140, with drill axis 5 held coincident with the axis of locking hole 38 by registration tool 110. The user may rotate all the way around drill axis 5 in either direction, or back and forth. In step 230, the position of sensor 10 relative to field generator 7 (expressed as transform Tws) is measured, the sensor to hole transform Tsh is calculated (as described above for FIG. 26), the corresponding heading 139 is calculated, and the Tsh and corresponding angle are stored in lookup table 242. Also in step 230, continuous measurement of Tws and calculation of heading 139 begins, and the difference between the current measured heading 139 and the last recorded value of heading 139 in lookup table 242 is calculated. In step 234 the difference between the current measured heading 139 and the last recorded heading in lookup table 242 is compared to a predetermined angular movement threshold. If the difference exceeds the threshold the current measured Tws and heading 139 pair is recorded and stored in lookup table 242. In step 236, the number of entries in lookup table 242 is compared to a predetermined minimum number of readings. In step 238 headings 139 in lookup table 242 are sorted into numerical order and the maximum difference between consecutive ordered headings in lookup table 242 is compared to a maximum angular gap. Recording continues until both the minimum number of readings in lookup table 242 and the maximum allowable angular gap between adjacent headings have been reached. A suitable angular movement threshold is three point five degrees, a suitable number of readings is two hundred, and a suitable maximum angular gap is two degrees.

In step 240, the completed lookup table 242 is interpolated by fitting a quadratic polynomial to position data and quaternions to data in the lookup table segments neighbouring the point of interest, to create a smooth transition between transforms Tsh at adjacent field generator headings 139. Alternately in step 240, a smooth function may be determined by curve fitting to the Tsh values recorded in steps 230 through 240, the resulting function producing corrected Tsh values as a function of heading 139. The system returns to step 212 giving the user the option to calibrate a second locking hole and generate a corresponding lookup table 243 for that hole, and so on until all desired holes are calibrated and each has an associated lookup table. After at least one hole is calibrated, at step 212 the user may proceed to steps 216 through 224 which are as described in FIG. 26.

In step 246, during tracking to target a locking hole, the position of sensor 10 relative to field generator 7 measured by the navigation system and expressed as transform Tws, and the current field generator heading 139 is calculated and the calibrated hole currently closest to drill axis 5 is determined. The lookup table corresponding to the closest calibrated hole is retrieved, the heading in the lookup table closest to the current heading is found, and the corresponding transform Tsh is retrieved from the lookup table and used to generate the display of relative position between locking hole coordinate system 136 and drill coordinate system 132 in step 248, thereby correcting for tracking errors that are a function of heading 139. The definition of drill axis 5 to field generator coordinate system 130 transform Twd may then be checked using the data from the hole registration procedure described above, by fitting a plane through the data points recorded from the origin of sensor coordinate system 134 as it rotates about drill axis 5 relative to field generator coordinate system 130, fitting a circle to the data points, and comparing the plane normal passing through the circle center to the Zd axis of drill coordinate system 132. Transform Twd may also be optimized by finding the Zd axis of drill coordinate system 132 relative to sensor coordinate system 134 at each of the data points recorded during rotation of field generator 7 about drill axis 5 in steps 230 to 240 above (using the current Twd and the recorded transform Tws at each data point), producing a group of axes, and modifying Twd until the variation in this group of axes is minimized. For example an optimization method such as a Nelder-Mead simplex method may be used to minimize the range of angles found between each Zd axis and the mean axis of the group.

Another aspect of the invention provides methods and apparatus for monitoring the measurement conditions affecting field generators integrated with tools. In an embodiment, the tool and field generator assembly may include a reference sensor in a fixed position relative to the field generator, and the location of the reference sensor is constantly monitored by the navigation system, and the nominally constant reading of reference sensor position may be analysed for unusual variations which may indicate measurement distortion, interference, signal noise, and the like.

In some embodiments the reference sensor may self-calibrate upon startup of the navigation system, during use, and/or upon a user-issued command. To calibrate the reference sensor the system may average a number of reference sensor readings at a time when there is unlikely to be unusual interference or distortion conditions present. For example reference sensor calibration may automatically carry out during the registration step described above. For another example the user may be prompted to run a reference sensor calibration with no known interference conditions present.

In some embodiments the reference sensor location may be compared to previous values stored in system memory to indicate a possible system error or change in the characteristics of the tool and field generator assembly. For example upon system startup, the last known calibrated location of the reference sensor may be retrieved from memory and compared to the current value, and if the difference is greater than a selected threshold, the user may be prompted to check for interference or distortion causing conditions, run a reference sensor calibration routine, or carry out a service procedure.

In some embodiments data from the reference sensor may also be used to help determine certain states of a tool, such as motor on or off, and certain conditions of use of the tool, such as motor speed range and engaged or not engaged with the target. For example the tool may have an electric motor, and the reference sensor data may be searched for characteristic variation corresponding to the motor running or not running.

An example of a method of using reference sensor data to monitor measurement conditions and modify navigation system function accordingly may comprise the steps of comparing selected parameters of the deviation in position and/or orientation of the reference sensor to predetermined threshold values, and then activating warning functions, modifying selected characteristics of the navigation system, and/or modifying the filtering and processing of navigation data including the display of navigation information to the user when the selected parameters or combinations of the parameters fall within a range of predetermined values or exceed threshold values. Parameters may include position and orientation of the reference sensor, or their time derivatives, or any other function thereof. Warning functions may be visual warning on the user interface, suspension of navigation, an alarm, and the like. Characteristics of the navigation system may include filtering parameters to smooth navigation data, for example applying selected filters when an electric motor in the tool is running.

Each feature of a method and apparatus for monitoring measurement conditions described above may be advantageous individually or in combination with some or all of the other features described. Other embodiments within the scope of the invention may include a subset of the advantageous features described above, and described in more detail in example embodiments below.

Figure 27:
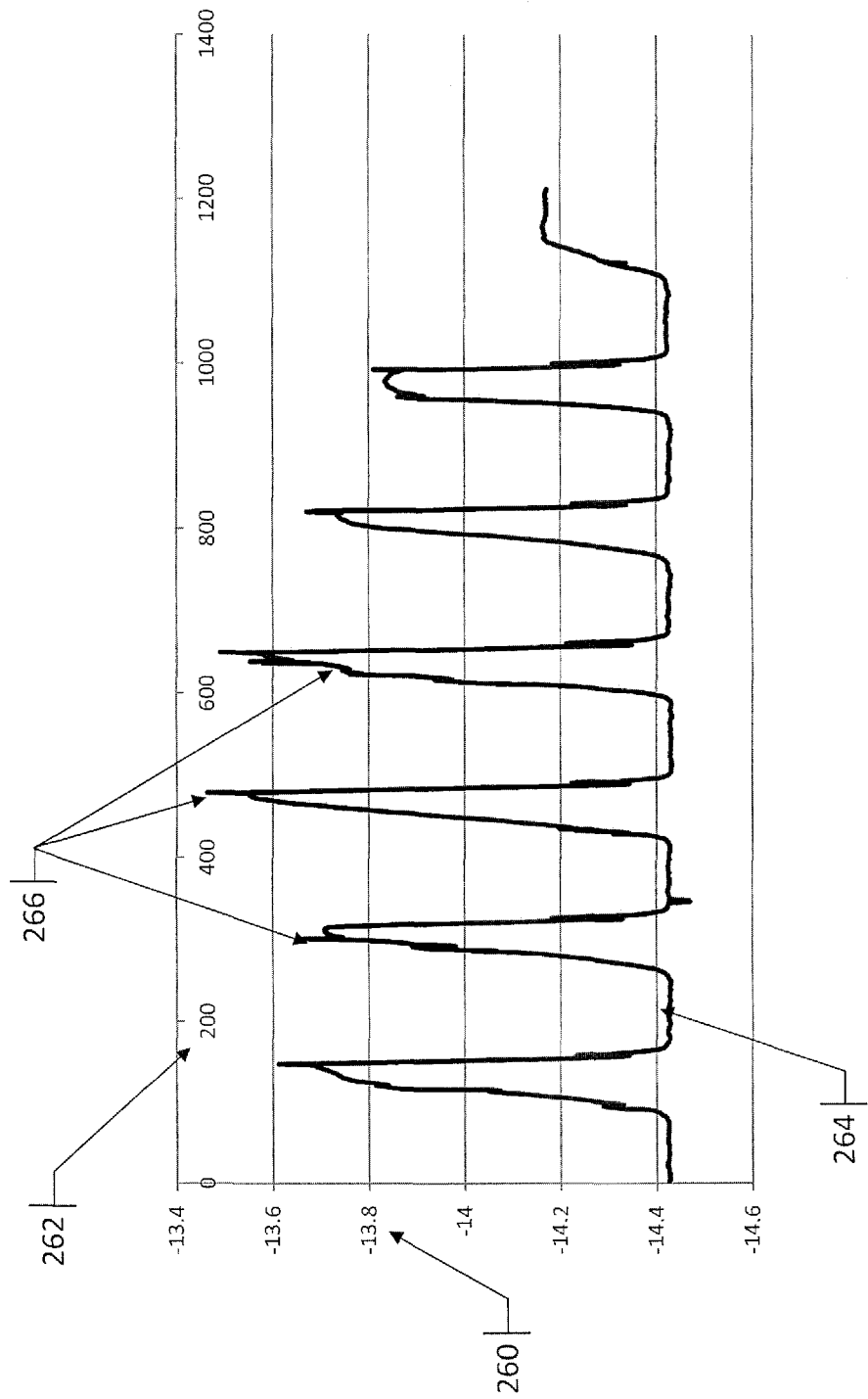
FIG. 27 shows an example plot of reference sensor readings when a ferromagnetic tool is passed in and out of the measurement range of a field generator and causing measurement error.

With reference to FIG. 27, in accordance with an embodiment of the invention, and referring also to FIG. 7, a plot of readings from reference sensor 8 is shown when a ferromagnetic tool is passed in and out of the measurement range of the field generator, creating a distorted field and causing measurement error. Vertical axis 260 is the Zw component of the transform Twr from the field generator coordinate system 130 to reference sensor coordinate system 137 in millimeters. Horizontal axis 262 is number of readings of Twr and the plot shown includes thirty seconds of continuous consecutive readings of Twr at a rate of forty hertz, the plot therefore showing about one thousand two hundred readings. Curve 264 is the Zw component of Twr when a ferromagnetic tool is passed in and out of the measurement range seven times during the thirty second recording, producing measurement distortion peaks 266.

With reference to FIG. 28, in accordance with an embodiment of the invention, and referring also to FIG. 7, a plot is shown of readings from reference sensor 8 when the electric motor of the attached drill 3 is started and stopped, creating external magnetic fields that affect the navigation system measurements. We have observed that drills such as drill 3 may produce magnetic field distortions when the drill motor is spinning, which in turn can cause high frequency signal noise affecting electromagnetic navigation systems. This signal noise can cause the targeting display to become erratic and show unrealistic movement of the graphic drill icon 392 shown in (FIGS. 18 and 18a) when the drill motor of drill 3 is running. This erratic display behaviour makes it difficult for the user to maintain and check alignment while drilling. In FIG. 28, vertical axis 270 is the Zw component of the transform Twr from the field generator coordinate system 130 to reference sensor coordinate system 137. Horizontal axis 272 is number of readings of Twr and the plot shown includes thirty seconds of continuous consecutive readings of Twr at a rate of forty hertz, the plot therefore showing about one thousand two hundred readings. Curve 274 is the Zw component of Twr when the motor of drill 3 is started and stopped eight times during the thirty second recording, producing measurement distortions 276 during the time the drill motor is running.

Another aspect of the invention provides methods and apparatus for filtering measurement data from field generators integrated with tools, which may include detection, exclusion, correction or estimation of data that is altered by interference or measurement errors. An embodiment the method may comprise the steps of reading the current sensor position and motion data, calculating selected characteristics of the data over a selected time period, comparing the characteristics to predetermined threshold values, deleting the current data if selected characteristics exceed selected thresholds, and monitoring the frequency of deleted position and orientation readings over a selected time period preceding the current reading, and if this frequency exceeds a selected threshold, displaying to the user a warning, and optionally displaying an estimate of current position and orientation calculated from previous data.

In another embodiment, a reference sensor in a fixed location relative to the field generator is used to provide a correlated measure of interference noise and used to remove interference noise in other sensors. Noise cancellation may be performed with a linear adaptive noise cancellation technique, or any other cancellation method that uses a noise reference source as input. For example a Kalman filter may be applied to the sensor readings. One ordinarily skilled in the art will recognize that any other adaptive method that uses the statistics of the input signal to adjust its filter behavior, such as recursive Bayesian estimation methods, may also be applied.

Each feature of a method and apparatus for filtering measurement data from field generators integrated with tools described above may be advantageous individually or in combination with some or all of the other features described. Other embodiments within the scope of the invention may include a subset of the advantageous features described above, and described in more detail in example embodiments below.

Figure 29:
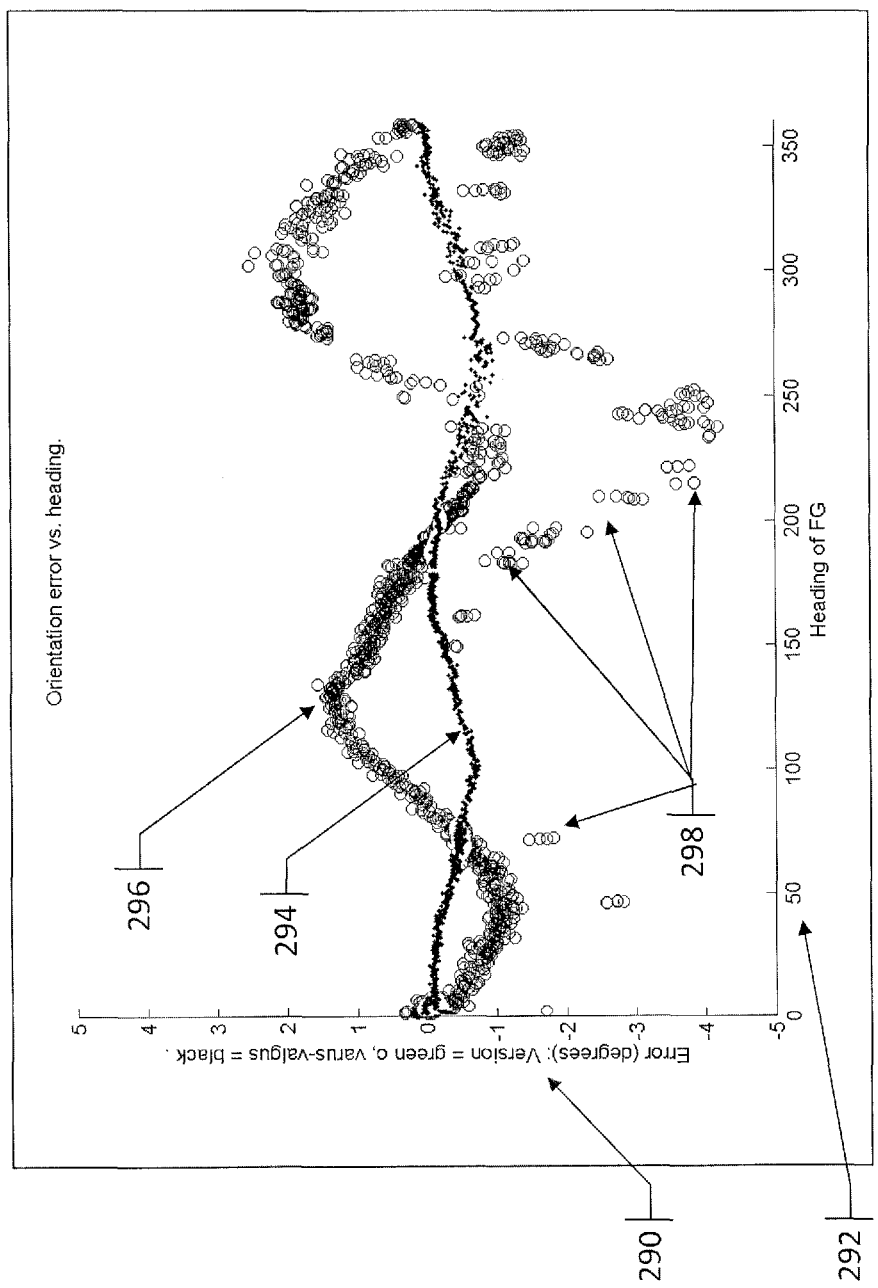
FIG. 29 shows an example plot of sensor orientation readings versus field generator position about the drill axis, with a field generator mounted to a typical drill.

With reference to FIG. 29, in accordance with an embodiment of the invention, a plot of orientation errors versus field generator heading is shown. Referring also to FIG. 7 and FIG. 7a, the plot shows data taken from a complete rotation of navigation unit 1 and drill 3 about drill axis 5, with the motor of drill 3 off, and no substantial magnetic interference present. Vertical axis 290 is the angular error in degrees of the tracked transform Tws from field generator coordinate frame 130 to sensor coordinate frame 134. Horizontal axis 292 is heading 139 of navigation unit 1 and drill 3 about drill axis 5. Curve 294 is the angular error in varus-valgus, which is defined as rotation about the Yh axis of locking hole coordinate system 136. Curve 296 is the angular error in version, which is defined as rotation about the longitudinal centerline 40 of nail 37. Curve 294 shows a generally smooth function of error in the range of plus or minus one half of a degree which is within the normal capabilities of typical electromagnetic tracking systems having a small enough field generator to be mounted on a hand-held tool, and a small enough sensor element for the exemplary application. Curve 296 shows a smooth pattern of errors of up to two degrees in version, which is expected because version error is rotation about the Zs axis of sensor coordinate system 134, which is typically two to four times less precise than rotation measurements about the remaining two axes Xs and Ys. This is a typical characteristic of electromagnetic tracking systems and is due to the physical arrangement of the sensing coils within sensor 10 being restricted to fit within a small radius about the Zs axis in order to make sensor 10 small enough to fit within the cannulation of nail 37 along longitudinal centerline 40. However outliers 298 of version error having magnitudes up to four degrees error have been observed and cause noticeable inconsistencies in tracking accuracy at various headings 139 and can lead to drill axis 5 being substantially misaligned with locking hole 38 when the targeting display indicates correct alignment.

Figure 30:
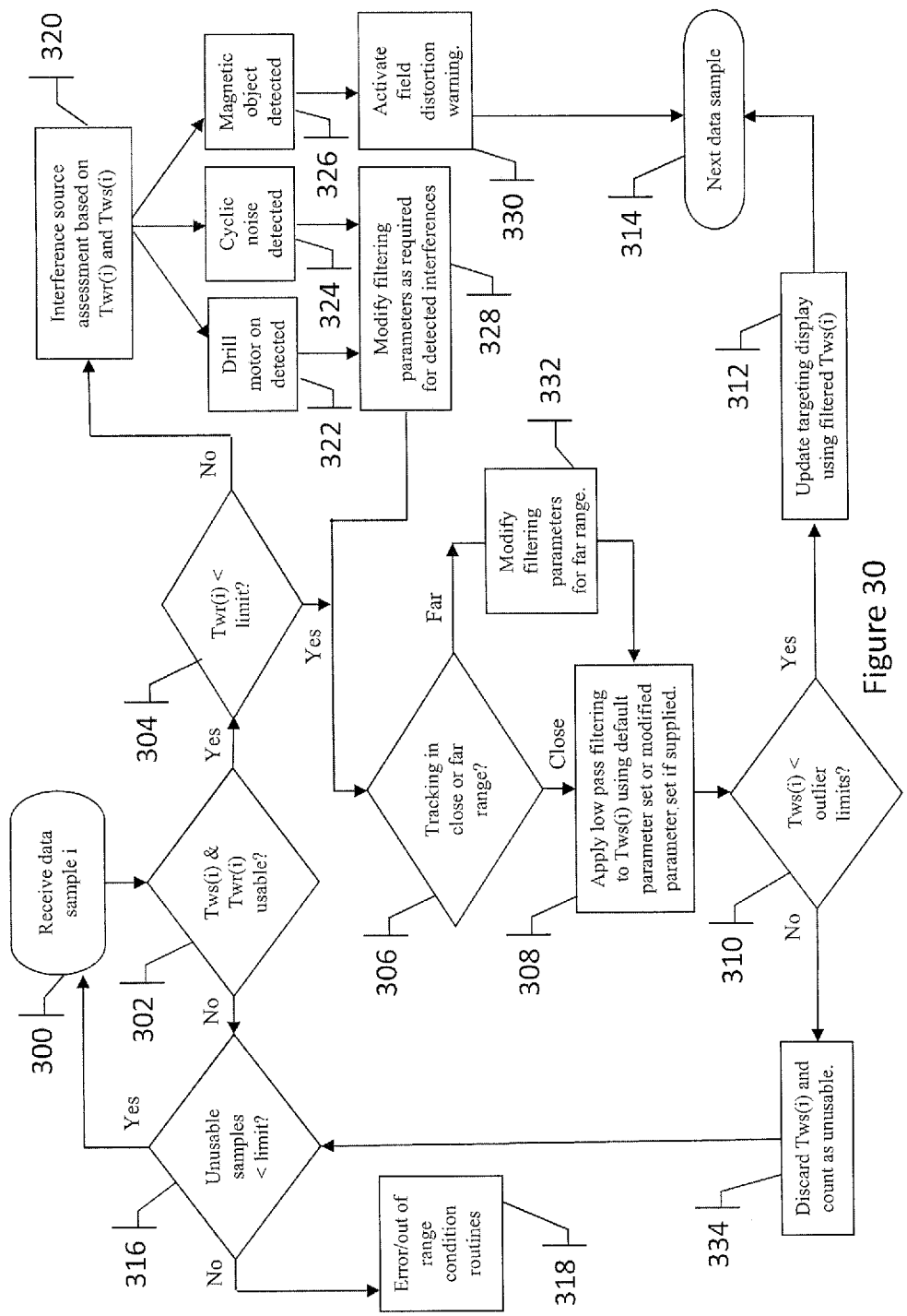
FIG. 30 shows a flowchart of an example filtering method for smoothing and correcting sensor position and orientation data during navigation, and modifying filtering parameters based on selected conditions detected by the system, according to one embodiment of the invention.

With reference to FIG. 30, in accordance with an embodiment of the invention, a flowchart of the filtering method for smoothing and correcting sensor position and orientation data during navigation is shown. The method generally includes the use of tracked sensor location and motion data, optionally in combination with reference sensor data, to determine signal processing parameters and inform the user of measurement conditions.

Referring also to FIG. 7, in step 300, the current reading of data is received from the navigation system. Typical navigation systems return parameters along with the spatial position data indicating if the data is present, and if so if it is valid or likely to be unreliable. In step 302, the parameters supplied by the navigation system are assessed, and if the current reading is usable the system proceeds to step 304 in which the data from the reference sensor is assessed. If in step 302 it is determined that the current reading is missing or invalid, the system indexes a missing sample counter by one and compares the missing data counter to a preselected limit in step 316. Alternately the limit for missing data in step 316 may be a percentage of missing readings over a selected time period, or a selected time period since the last usable reading. If the limit of missing data has been reached, the system moves to step 318 and an unreadable data state or warning is activated. Step 318 most commonly will be activated by sensor 10 being out of range, however other conditions may be detectable from the parameters supplied by the navigation system, and this information is passed to step 318 to activate a more specific warning (for example sensor unplugged, field generator unplugged, and unrecognized sensor type).

If in step 302 the reading is successful, the transforms Tws from field generator coordinate system 130 to sensor coordinate system 134 and Twr from field generator coordinate system 130 to reference sensor coordinate system 137 are received and in step 304 the current transform Twr(i) is compared to the constant Twr stored in system memory. If the current Twr(i) differs from the stored constant Twr by more than a predetermined limit, some form of interference or distortion of tracking is indicated and the system moves to interference assessment and classification step 320.

Referring also to FIG. 27 and FIG. 28, distortion 266 due to ferromagnetic object interference and distortion 276 due to drill motor interference are distinguishable from each other and from the referenced sensor location tracked during normal aiming motions as shown in curve 284. Therefore by monitoring reference sensor 8 continuously during targeting a warning message can be activated when distortions similar to distortion 266 having parameters above predetermined thresholds are detected. Suitable parameters for magnetic object interference detection are a threshold of three millimeters for position and a threshold of 0.01 for orientation expressed as quaternions. Similarly activation of the drill motor in drill 3 may be detected by monitoring for distortions similar to distortion 276 having parameters above predetermined thresholds, and signal processing parameters such as noise filtering parameters may be changed accordingly. Similarly cyclic interference from nearby equipment also typically have distinct patterns of variation in Twr(i). Interference may also create distinct variations in Tws(i) that may also be used to detect and classify the type of interference. Interference may also create distinct variations in Tws(i) that may also be used to detect and classify the type of interference. In step 320 the type of interference is identified and classified into classes 322, 324, or 326.

Depending on the type of interference detected, filtering and data smoothing parameters may be selected in step 328 to make the data usable, or if the data is inaccurate (such as in the case of a constant field distortion due to a ferromagnetic object being too close to field generator 7 or sensor 10), filtering cannot make the data usable then the system proceeds to step 330 in which a warning is activated. If in step 304 the current Twr(i) matches the stored constant Twr within the predetermined limit, the system proceeds to step 306 to determine what region of the measurement range sensor 10 is in.

Typically, navigation systems have worse response, accuracy, and precision in the far range which can lead to greater measurement noise levels and in turn a jumpy or erratic targeting display. In the exemplary embodiment, the measurement range of field generator 7 is divided into two ranges, close range and far range. Close range is defined as sensor 10 being within the cylindrical volume about the Zw axis of field generator coordinate system 130 extending from Zw of negative five millimeters to negative one-hundred and eighty millimeters and having a radius of one hundred and ten millimeters. Far range is defined as sensor 10 being within the cylindrical volume about the Zw axis of field generator coordinate system 130 extending from Zw of negative five millimeters to negative two-hundred and seventy-five millimeters and having a radius of two hundred millimeters, but excluding the close range volume defined above. If the current reading Tws(i) is in the far range, the system proceeds to step 332 and applies filtering parameters suitable for the far range. In the exemplary embodiment a moving average filter is used with default averaging over ten samples while in the close range, increasing to twenty samples while in the far range. In step 308 either a default low pass filter or the filtering parameters determined in the preceding steps is applied to Tws. In step 310 the current filtered Tws(i) is compared to previous values and it is determined if Tws(i) is an outlier 298 (as shown in FIG. 29).

In the exemplary embodiment, outliers 298 are detected by comparing the change of Tws over a selected time period to a threshold. If the change is substantially higher than that normally recorded during targeting, an outlier 298 is indicated. A suitable time period is fifty milliseconds and a suitable change threshold is ten millimeters for translation and 0.25 for orientation expressed as quaternions, with both thresholds applied to the sum of the absolute values. If an outlier 298 is detected, the system proceeds to step 334 and the current reading is discarded, the missing reading counter is indexed, and the system returns to step 316. If it is determined in step 310 that Tws(i) is not an outlier, the system proceeds to step 312, where the targeting display is updated using filtered data, and then to step 314 where the next data sample is retrieved from the navigation system.

FIG. 31 through FIG. 38 show several examples of embodiments of an aspect of the invention providing apparatus and method to lock a bone fragment to an IM nail in such a way as to maintain, temporarily or permanently, an open passage through the cannulation along the longitudinal centerline of the nail.

Figure 31:
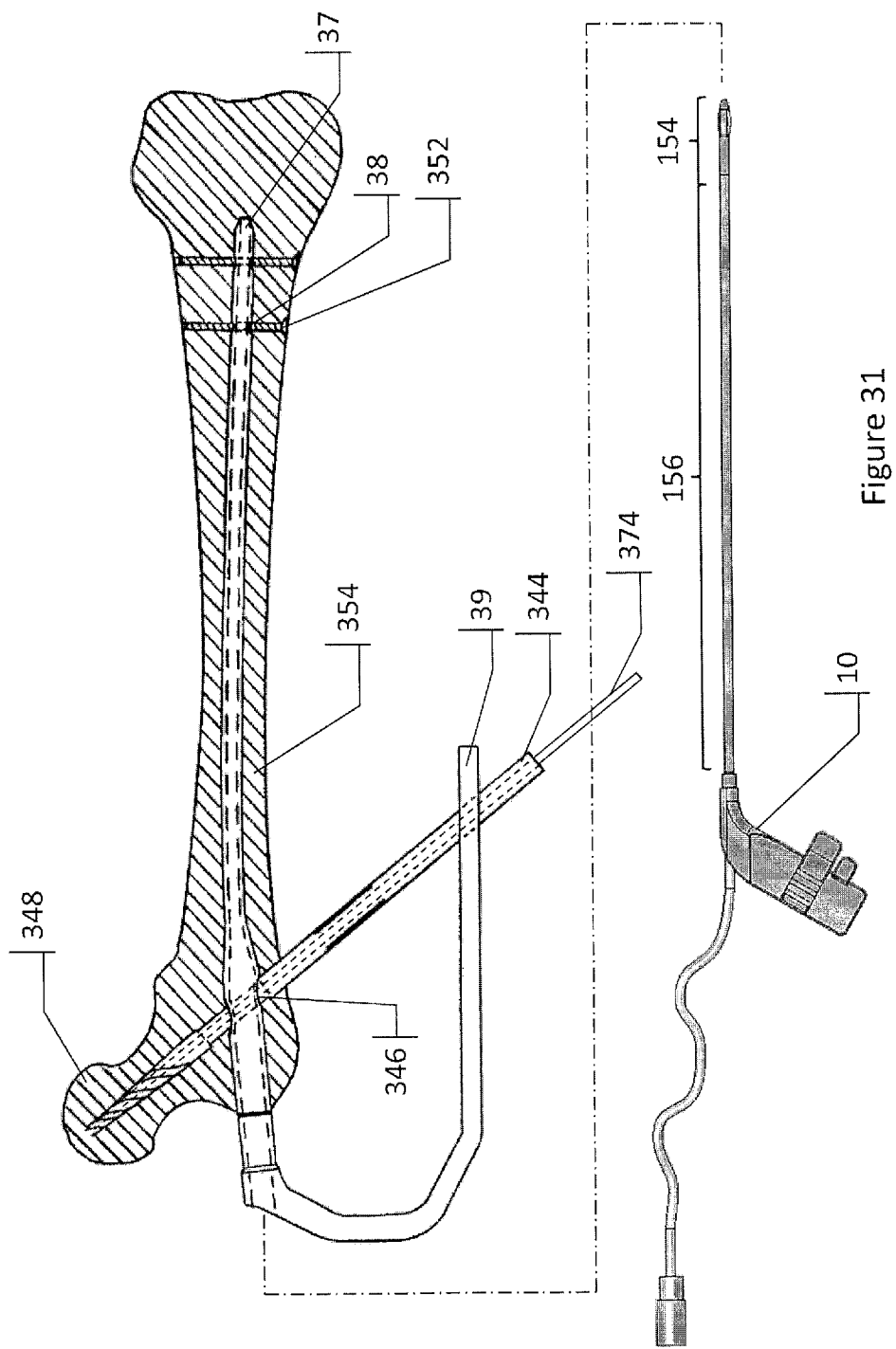
FIG. 31 shows an IM nail implanted in a femur, with the femur shown in section, with a fenestrated drill bit passing through the femoral neck and into the femoral head, and a sensor tool, in accordance with one embodiment of an aspect of the invention.

With reference to FIG. 31, in accordance with the exemplary embodiment of the invention, sensor tool 10 having shaft portion 156 and tip portion 154 fits inside IM nail 37 which is implanted in femur 354. Insertion tool 39 is temporarily bolted to nail 37 during the insertion and positioning of nail 37 in femur 354. Insertion tool 39 also has a guide hole to align proximal locking drill bit 344 with proximal locking hole 346. Proximal locking drill bit 344 passes through proximal locking hole 346 of nail 37 and extends up into femoral head 348 over guide wire 374 to prepare a hole for a permanent locking element (not shown) to be installed at a later stage in the procedure. Tip portion 154 contains a sensor element as described above in FIG. 1a through FIG. 6 and is used as described above to locate distal locking hole 38 of nail 37, in particular to guide a drill in drilling through femur 354 in line with distal locking hole 38 for installation of distal locking screw 352.

Figure 32:
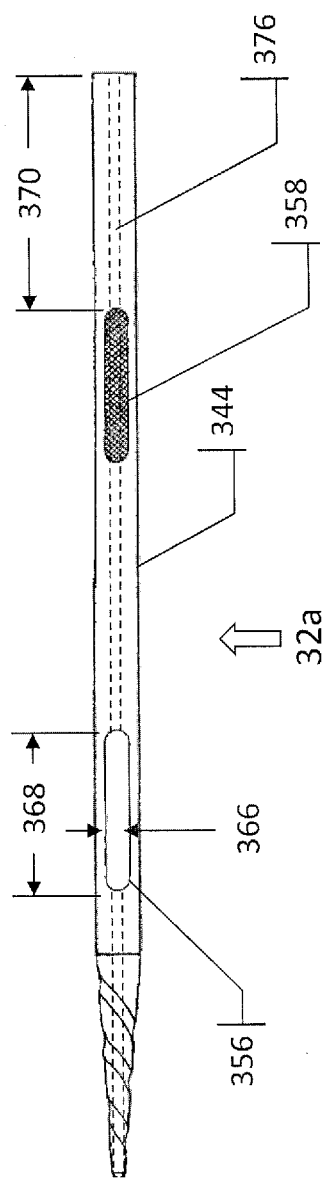
FIG. 32 shows the fenestrated drill bit, looking along the axis of the slotted hole.

With reference to FIG. 32, in accordance with the exemplary embodiment of the invention, proximal locking drill bit 344 is shown having cannulation 376, slotted hole 356 having width 366 and length 368, and marking 358 aligned with slotted hole 356. Marking 358 is the same size and shape as slotted hole 356, located a selected distance 370 along drill bit 344 to be visible outside of the patient's body when drill bit 344 is passed to the desired maximum depth into femur 354 (seen in FIG. 31) and is duplicated on the opposite side of drill bit 344 so that the user can see the orientation of slotted hole 356 at one hundred and eighty degree intervals in the rotation of drill bit 344. One ordinarily skilled in the art will recognize that marking 358 may alternately be any suitable indicator indicating the rotational orientation of slotted hole 356 (for example an arrow, hole, groove, or slot) located at a known fixed rotational orientation about the longitudinal axis of drill bit 344 relative to slotted hole 356, and that a single marking 358 may be used.

Figure 33:
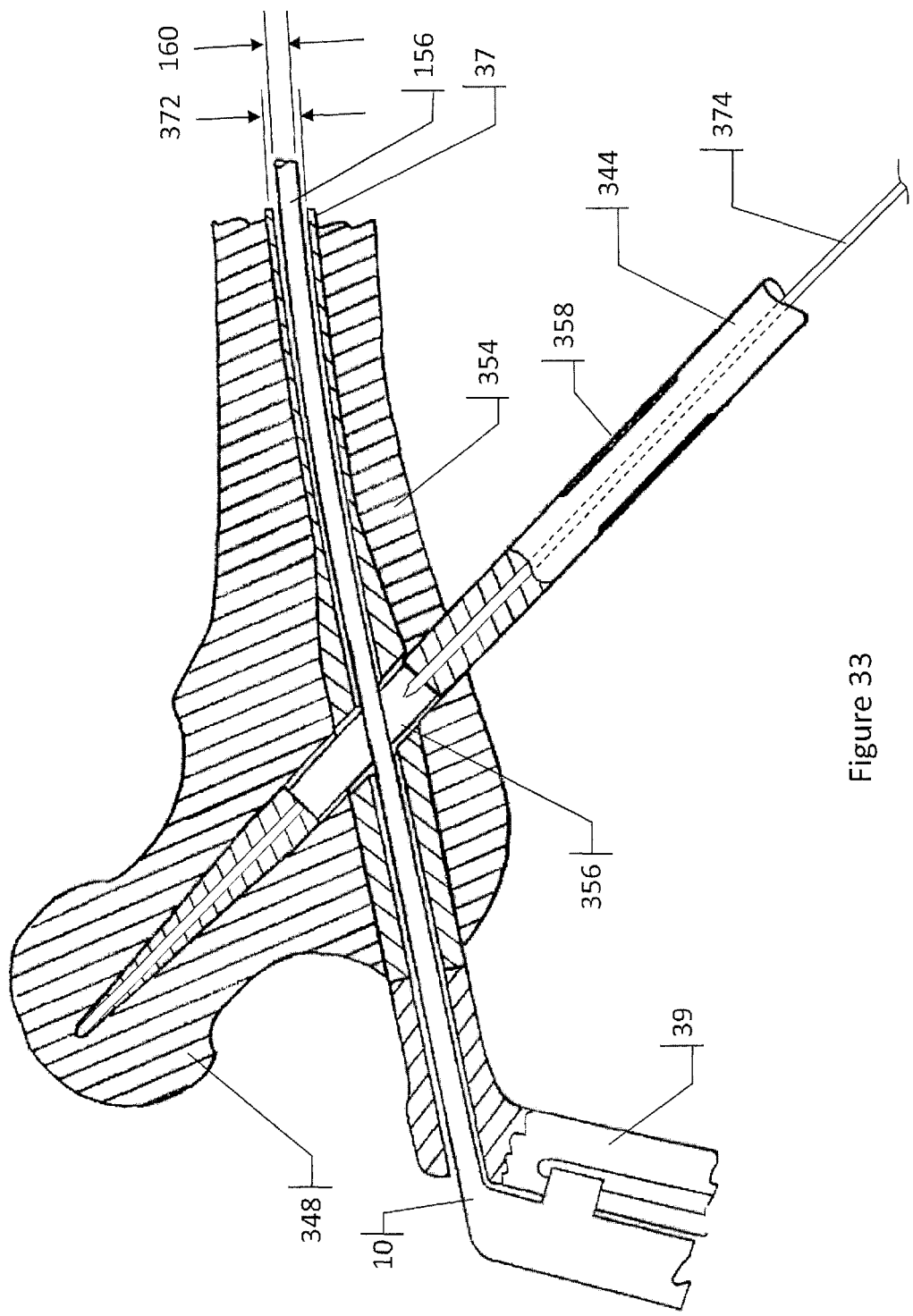
FIG. 33 shows a section view through the femur and the IM nail with the fenestrated drill bit in place and a sensor tool installed.

Referring to FIG. 31, FIG. 32 and FIG. 33, diameter 360 of drill bit 344 is selected to suit the permanent locking element that will be installed through proximal locking hole 346, slotted hole width 366 is selected to be similar to nail cannulation diameter 372 and large enough for tip portion 154 of sensor tool 10 to pass through, and slotted hole length 368 is selected to encompass the range of distances between nail 37 and femoral head 348 encountered among patients of different sizes. A suitable diameter 360 for drill bit 344 is eleven millimeters, a suitable width 366 of slotted hole 356 is six millimeters, and a suitable length 368 of slotted hole 356 is twenty millimeters. Cannulation 376 has a diameter selected to slide over guide wire 374. Examples of suitable diameters are 3.2 millimeters for guide wire 374 and 3.4 millimeters for cannulation 376. One ordinarily skilled in the art will recognize that slotted hole 356 may alternately be a variety of shapes, for example an oval, elliptical, or a cylindrical hole may be used. One ordinarily skilled in the art will also recognize that depending on the size and flexibility of sensor tool 10, slotted hole 356 could be offset from the centerline of nail 37, need not be symmetrical about the centerline of nail 37, and could have the form of a notch or recess instead of a fenestration.

Figure 32A:
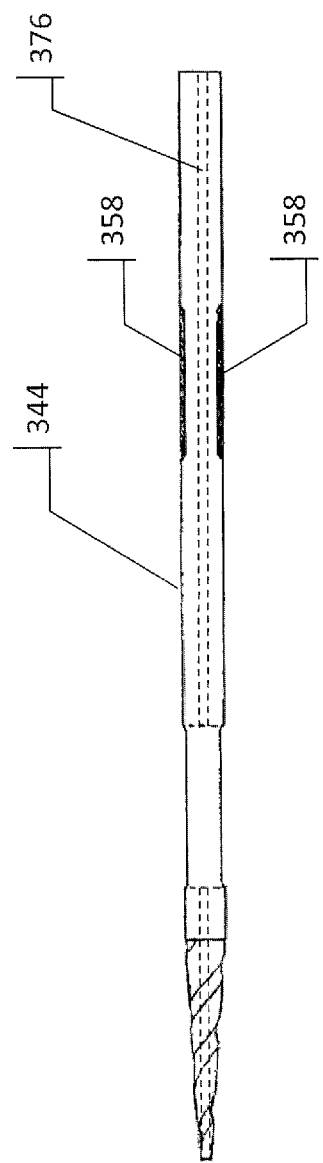
FIG. 32a shows the fenestrated drill bit, looking normal to the axis of the slotted hole.

With reference to FIG. 32a, in accordance with the exemplary embodiment of the invention, a side view of proximal locking drill bit 344 is shown with cannulation 376 and with markings 358 visible.

With reference to FIG. 3, in accordance with the exemplary embodiment of the invention, a section view taken in a frontal plane through the midline of femur 354 is shown, in the area of the proximal femur only. Shaft portion 156 of sensor tool 10 has shaft diameter 160, suitable diameters being in the range of three to four millimeters, and nail 37 has a cannulation along its axis having diameter 372, typically in the range of four to five millimeters. Drill bit 344 is shown having been drilled to the appropriate depth into femoral head 348 as determined by the surgeon over guide wire 374, and guide wire 374 has been pulled out laterally enough to clear the cannulation diameter 372 in nail 37, and could optionally be withdrawn completely. Slotted hole 356 in bit 344 is approximately aligned with the cannulation in nail 37 by visually aligning markings 358 with the patient's limb, such that the tip portion 154 (seen in FIG. 31) and shaft portion 156 of sensor tool 10 may pass through slotted hole 356 as sensor tool 10 is installed in nail 37.

With reference to FIG. 31, FIG. 32, and FIG. 33, an exemplary method of use of an aspect of the invention is as follows: IM nail 37 is inserted in femur 354 with insertion tool 39 attached. The fragments of femur 354 are positioned and the position of nail 37 in femur 354 is set, and drill bit 344 is passed through proximal locking hole 346 and into femoral head 348 over guide wire 374 to the appropriate depth. Drill bit 344 is then rotated to a position where markings 358 are in proximal and distal facing positions relative to femur 354. Guide wire 374 is then drawn back out of the femur with drill bit 344 left in place to hold the proximal fragments of femur 354 in place. Sensor tool 10 is then inserted into nail 37 to facilitate installation of distal locking screw 352. When distal locking is complete sensor tool 10 is removed, guide wire 374 may be reinserted if desired, drill bit 344 is withdrawn, and the permanent proximal locking element (not shown) is installed through proximal locking hole 346 and into femoral head 348.

Figure 34:
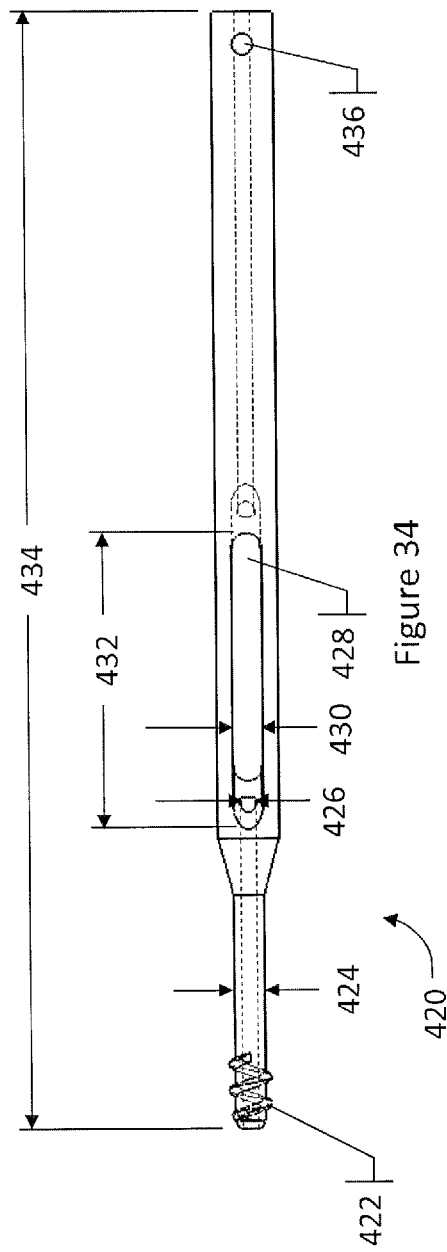
FIG. 34 shows a top view of a cannulated and fenestrated stud, according to an alternate embodiment of an aspect of the invention.
Figure 35:
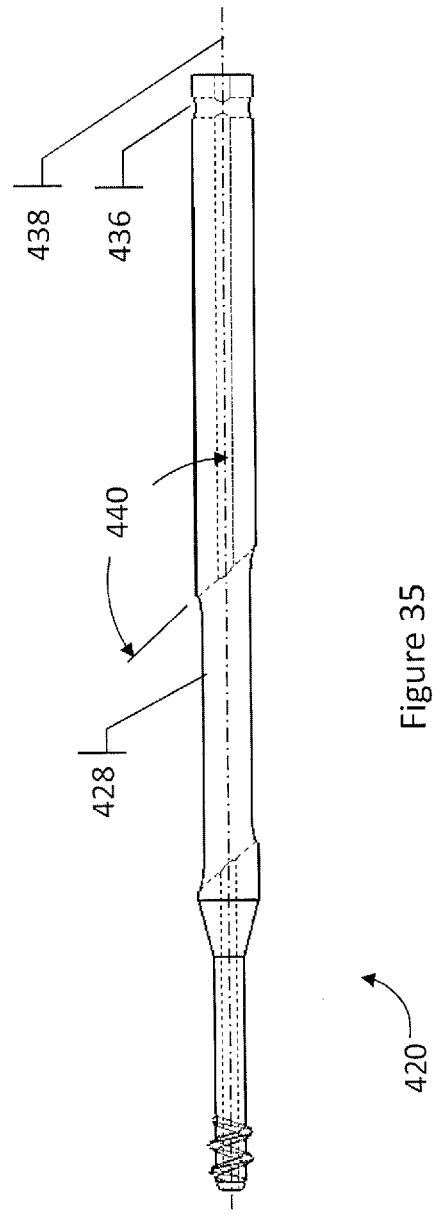
FIG. 35 is a front view on the alternate embodiment of the invention shown in FIG. 34.
Figure 36:
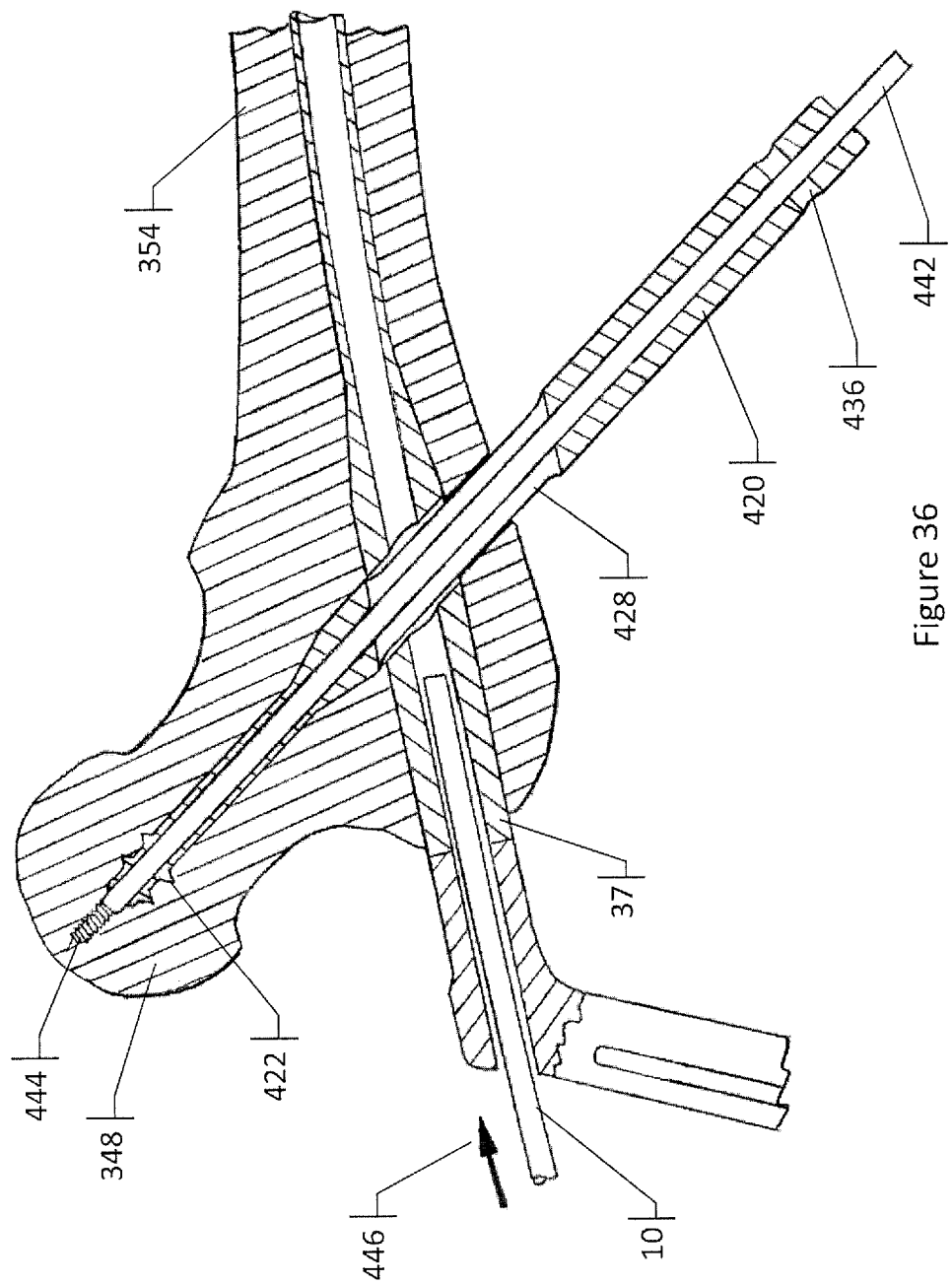
FIG. 36 shows a section view through a femur and IM nail showing the cannulated and fenestrated stud of FIG. 34 and a guide wire in place, before retraction of the guide wire.

Referring to FIGS. 31 through 33, one skilled in the art will recognize that other embodiments are possible in which, in place of drill bit 344, a temporary stud or guide wire having a slotted hole similar to slotted hole 356 may be used (one such exemplary alternate embodiment is shown in FIGS. 34, 35, and 36 below). One skilled in the art will also recognize that a slotted hole similar to slotted hole 356 may be placed directly in the permanent locking element.

With reference to FIG. 34, in accordance with an alternate embodiment of the invention, a top view of temporary locking stud 420 is shown. One end of stud 420 is screwed into the femoral head during use, with threads 422 engaging the femoral head fragment. Outer diameter 424 in this area may be, for example, 5.4 millimeters. Stud 420 is cannulated along its entire length, the cannulation having diameter 426 selected to be suitable to slide over a guide wire (see FIG. 36). Slotted hole 428 has width 430 approximately equal to, or greater than, the cannulation diameter 372 of IM nail 37 (seen in FIG. 33), and has length 432. Length 432 is chosen to allow for a range of distances along the axis of stud 420 from the centerline of nail 37 up into the femoral head 348 to the tip of stud 420, such that the centerline of nail 37 lies within length 432 when stud 420 is installed. To accommodate the range of femoral neck lengths encountered across the patient population, a set of studs 420 having different slotted hole lengths 432 and overall lengths 434 may be provided. Indicator hole 436 is aligned with slotted hole 428, and also has a diameter suitable for insertion of a pin wrench or a rod to allow easier turning of stud 420, for insertion and removal. For example a suitable diameter for indicator hole 436 is 4.4 millimeters.

With reference to FIG. 35, a front view of the alternate embodiment of the invention shown in FIG. 34 is shown. Temporary locking stud 420 of the alternate embodiment is shown. Stud 420 has longitudinal axis 438. Slotted hole 428 is oriented at angle 440 which is chosen to match typical femoral neck to shaft angles. A suitable value for angle 440 is one hundred and thirty degrees. Indicator hole 436 is also shown.

With reference to FIG. 36, in accordance with the alternate embodiment of the invention shown in FIG. 34, a section view taken in a frontal plane through the midline of femur 354 is shown, in the area of the proximal femur only. Guide wire 442 having threads 444 at one end is shown inserted into femoral head 348 with threads 444 engaged in the cortical bone near the outer surface of femoral head 348. Stud 420 is shown in position over guide wire 442 with threads 422 engaging femoral head 348 lateral to guide wire threads 444. Slotted hole 428 in stud 420 is approximately aligned with the cannulation in nail 37 by visually aligning indicator hole 436 with the patient's limb, such that guide wire 442 may be temporarily withdrawn without losing stabilization of femoral head 348, and then sensor tool 10 (see also FIG. 31) may pass through slotted hole 428 as sensor tool 10 is installed in direction 446 into the cannulation of nail 37. After distal locking is completed and sensor tool 10 is removed, guide wire 442 may be re-inserted and threaded back into femoral head 348, stud 420 removed, and the permanent locking element installed over guide wire 442.

With reference to FIG. 31 and FIGS. 34 through 36, the method of use of the alternate embodiments of the invention is similar to that of the exemplary embodiment, except that only the lateral cortex of femur 354 is drilled using a drill bit, and stud 420 is used in place of drill bit 344. This method may be used when it is preferable not to drill through the femoral neck and into femoral head 348 and instead use the guide wire 442 only to stabilize femoral head 348 and to guide the installation of the permanent locking element.

Figures 37, 37A:
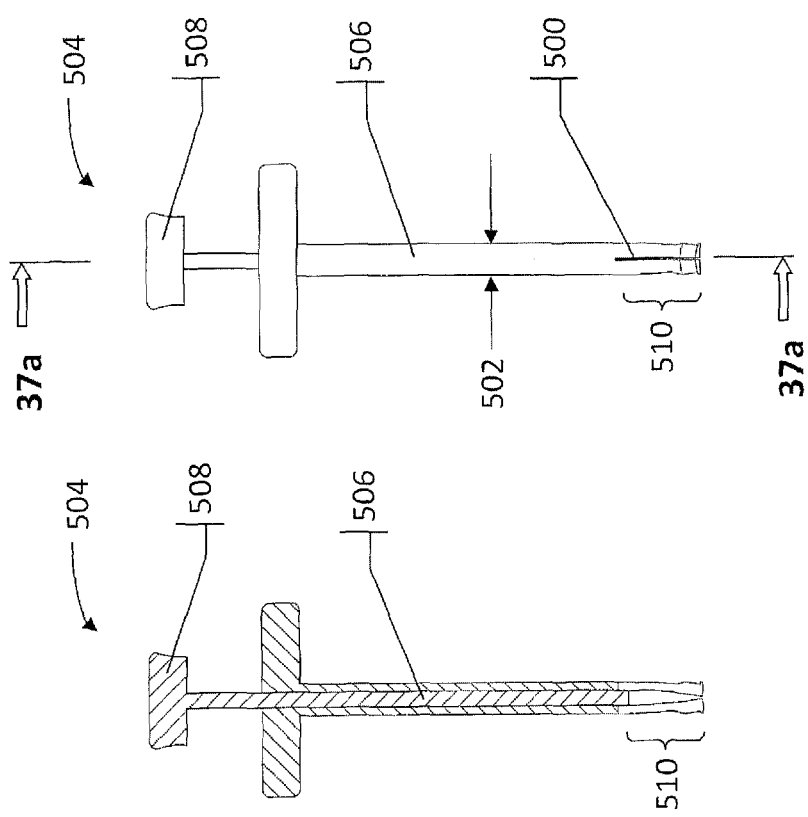
FIG. 37 shows an expanding stud which engages only one cortex of the bone and one wall of the nail, in accordance with yet another embodiment of an aspect of the invention.
FIG. 37a is a section view taken from FIG. 37 through the expanding stud.
Figure 38:
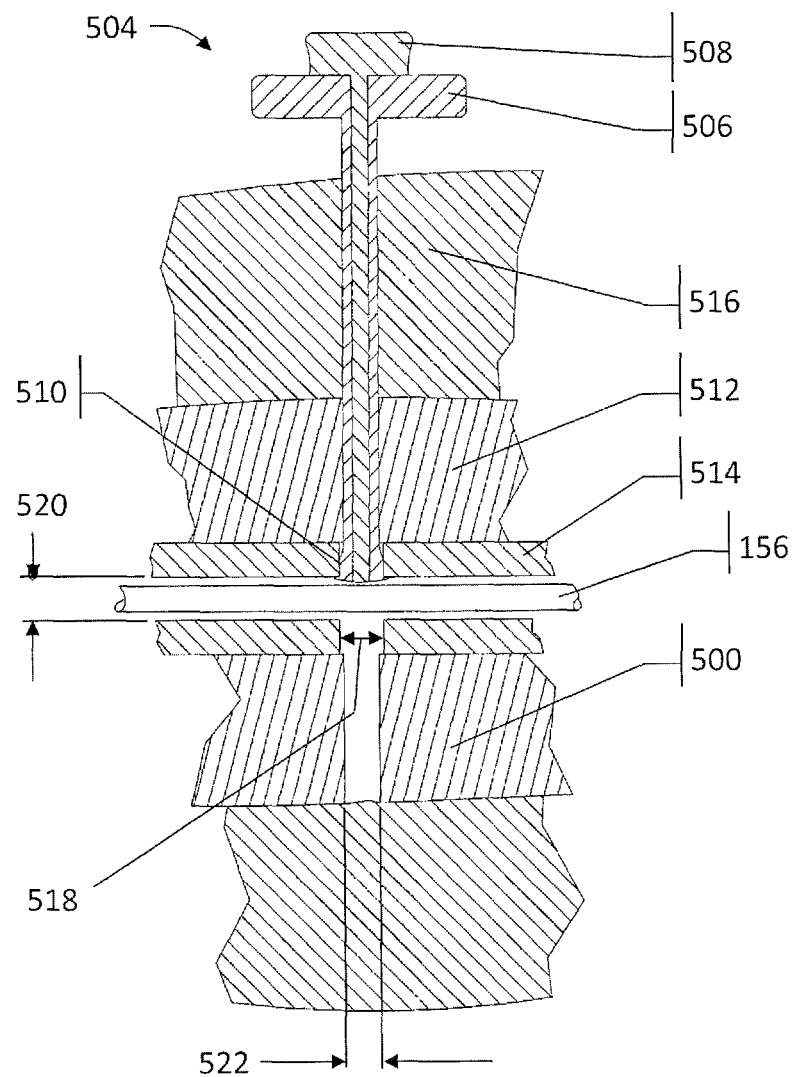
FIG. 38 is a section view of the expanding stud of FIG. 37 in use in a patient's limb.

With reference to FIG. 37, FIG. 37*a*, and FIG. 38, a second alternate embodiment of the invention is shown for applications where the locking hole diameter is similar to the cannulation diameter, in which case the drill bit used to drill the locking hole is too small to accommodate a slotted hole as shown in the exemplary embodiment. FIG. 37 shows stud 504 having an outer portion 506 and a plunger 508. Outer diameter 502 is selected to be a sliding fit in drill hole 522 (see FIG. 38) made in the bone for a locking screw. Expanding tip portion 510 has two slits 500 dividing expanding tip portion 510 into four quadrants.

FIG. 37*a* is a section through stud 504 showing plunger 508 which is a sliding fit inside outer portion 506. Stud 504 may be made of, for example, stainless steel, titanium, or of a high modulus autoclavable plastic such as PEEK or of any other material which provides sufficient resistance to deflection and shear.

FIG. 38 is a section view through bone 512 with IM nail 514 implanted and stud 504 shown engaged in only one cortex of bone 512 and one wall of nail 514. Nail 514 has cannulation of diameter 520 which is similar to locking hole diameter 518. Locking hole drill diameter 522 is slightly smaller than locking hole diameter 518. In use the locking hole drill (not shown) is passed through soft tissues 516, one cortex of bone 512, nail 514, and the opposite cortex of bone 512. Stud 504 is slid through the resulting drill hole far enough to engage one wall of nail 514 and plunger 508 is pushed down relative to outer portion 506, expanding tip portion 510 (see FIGS. 37 and 37*a*) out to an interference fit with locking hole 518. Sensor tool shaft portion 156 may be passed through the cannulation in nail 514 after drilling, and either before or after installation of stud 504. Stud 504 thereby holds nail 514 in place relative to bone 512 while sensor tool 10 (see FIG. 31) is in use. When sensor tool 10 is no longer required it is removed, stud 504 is removed, and the permanent locking element (such as a locking screw, not shown) is installed through bone 512 and nail 514.

Some embodiments of the invention comprise kits made up of one or more of the tools and devices described herein. For example, a kit may comprise one or more sensor tools as described herein and one or more implants or other components with which those sensor tools may be used. Such a kit may further comprise one or more. insertion tools attachable to the implants or other components. The sensor tools and insertion tools may be configured with features permitting the sensor tools to be detachably coupled to the insertion tools. Such a kit may also comprise a registration tool for registering a tool with an implant or other component. Another example of a kit comprises a tool and one or more of a field generator attachable to the tool, a display attachable to the tool and a navigation unit attachable to the tool. In some embodiment the kit comprises multiple different tools and the field generator and tools are configured to allow the field generator to be coupled to any of the different tools. The navigation unit may comprise a field generator and display (which may be fixed to or detachable from the navigation unit). Such a kit may also comprise a registration tool for registering the tool with an implant or other component. Such a kit may also comprise one or more tool members such as one or more drill bits, saws, pins, milling cutters, or the like.

All publications, patents and patent applications are herein incorporated by reference to the same extent as if each individual publication or patent application was specifically and individually indicated to be incorporated by reference.

INTERPRETATION OF TERMS

Unless the context clearly requires otherwise, throughout the description and the claims:
"comprise," "comprising," and the like are to be construed in an inclusive sense, as opposed to an exclusive or exhaustive sense; that is to say, in the sense of "including, but not limited to".
"connected," "coupled," or any variant thereof, means any connection or coupling, either direct or indirect, between two or more elements; the coupling or connection between the elements can be physical, logical, or a combination thereof.
"herein," "above," "below," and words of similar import, when used to describe this specification shall refer to this specification as a whole and not to any particular portions of this specification.
"or," in reference to a list of two or more items, covers all of the following interpretations of the word: any of the items in the list, all of the items in the list, and any combination of the items in the list.
the singular forms "a", "an" and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

Data processing features of embodiments of the invention may be implemented using specifically designed hardware, configurable hardware, programmable data processors configured by the provision of software (which may optionally comprise 'firmware') capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs") and the like. Examples of configurable hardware are: one or more programmable logic devices such as programmable array logic ("PALs"), programmable logic arrays ("PLAs") and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors. Any of the methods as described above may be implemented in any of these ways. A system according to certain embodiments of the invention may be configured to perform one or more of the methods described herein. Where a system is configured to perform more than one function or method as described herein different methods or functions may be implemented using the same or different hardware. For example, a computer processor may serve to provide computation for a position sensing system and also to coordinate and/or implement one or more methods as described herein. In other embodiments different methods and/or different functions may be implemented using different hardware.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

Software and other modules may reside on servers, workstations, personal computers, tablet computers, database servers, and other devices suitable for the purposes described herein.

Some embodiments of the invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

Where a component (e.g. a coupling, sensor, field generator, display, tool, software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

Another example application of apparatus as described herein is a tool-mounted display. Such a display may be used with milling tools to monitor the cutting process, on saws to control alignment and/or depth of cut, on reamers to control acetabular cup placement, on pin insertion guides to control insertion of K-wires and the like.

Described methods may be varied. For example, while processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times. In addition, while elements are at times shown as being performed sequentially, they may instead be performed simultaneously or in different sequences.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations.

What is claimed is:

1. A hand tool comprising:
a hand-holdable body;
a tool member coupled to the body;
a field generator coupled to the body, the field generator operable to emit a field for detection by a sensor of a position-sensing system, the field permitting determination of the position of the sensor relative to the field generator; and
a correction unit configured to correct a position of the sensor based at least in part on the determined position of the sensor relative to an axis of the tool member and a fixed point on the tool member to which the field generator has a known spatial relationship;
wherein the tool member has an axis of rotation and the coupling is configured to permit rotation of the field generator about the axis of rotation of the tool member, wherein the field generator is coupled to the body by an adjustable coupling permitting the field generator to be moved relative to the body, wherein the coupling is configured to maintain a fixed radial spacing of the field generator to the axis of rotation of the tool member and the tool comprises a plurality of mounting couplings and the field generator is detachably affixable to each of the plurality of mounting couplings.

2. A hand tool according to claim 1, wherein the tool member has an axis of rotation and the plurality of mounting couplings are angularly spaced apart around the axis of rotation.

3. A hand tool according to claim 2, wherein the mounting locations are on a circle centered on the axis of rotation.

4. A hand tool according to claim 1, wherein the field generator is supported on a navigation unit that is detachably coupled to the body, the navigation unit comprises a bushing, and the tool member passes through the bushing.

5. A hand tool according to claim 4, wherein the field generator is supported on a navigation unit that is detachably coupled to the body, the navigation unit comprises a rotatable shaft coupled to be turned by the motor, and the tool member is coupled to the rotatable shaft.

6. A hand tool according to claim 5, wherein the field generator is supported on a navigation unit that is detachably coupled to the body the navigation unit comprises a drill chuck and the body comprises a drill motor attachable to drive the drill chuck.

7. A hand tool according to claim 6, further comprising a display targeting information from a navigation system, wherein the display is coupled to the body via a display coupling, the display coupling allowing for pivotal motion relative to an axis of the tool.

8. A hand tool according to claim 7, further comprising an inclinometer coupled to the display, the inclinometer providing an output signal indicating an inclination of the display.

9. A hand tool according to claim 8, wherein the inclinometer comprises an accelerometer.

10. A hand tool according to claim 8, wherein an orientation of content displayed on the display is controlled based on the on the output signal from the inclinometer.

11. A hand tool according to claim 10, further comprising an encoder configured provide an output signal indicative of an angular position of the display relative to the body.

12. A hand tool according to claim 11, wherein an orientation of content displayed on the display is controlled based on the on the output signal from the encoder.

13. A hand tool according to claim 1, further comprising a reference sensor, the reference sensor operable to receive the field emitted by the field generator and to output a signal indicative of a position of the reference sensor relative to the field generator, wherein the reference sensor is one of affixed to and housed within a housing of the field generator.

14. A hand tool according to claim 13, further comprising a plurality of reference sensors one of affixed to and housed within the tool.

15. A hand tool according to claim 1, further comprising a registration tool having a member projecting along a registration axis wherein the registration tool is adapted to be temporarily coupled to the tool member such that the registration axis is held in a predetermined spatial relationship relative to an axis of the tool member.

16. The hand tool according to claim 15, wherein the member of the registration tool is configured to be temporarily coupled to a target feature of a component such that the registration axis is held in the first predetermined spatial relationship relative to an axis of the target feature.

17. The hand tool according to claim 15, wherein the member of the registration tool comprises a tip portion that is compressible to fit snugly into target features of a plurality of different sizes.

18. The hand tool of claim 15, wherein the member of the registration tool comprises at least one resiliently elastic element.

19. The hand tool of claim 15, wherein the member of the registration tool is coaxial with the tool member when the registration tool is coupled to the tool member.

* * * * *